US012653429B2

(12) United States Patent
Ray et al.

(10) Patent No.: US 12,653,429 B2
(45) Date of Patent: *Jun. 16, 2026

(54) TRANS-ABDOMINAL FETAL PULSE OXIMETRY AND/OR UTERINE TONE DETERMINATION DEVICES AND SYSTEMS WITH ADJUSTABLE COMPONENTS AND METHODS OF USE THEREOF

(71) Applicant: Raydiant Oximetry, Inc., San Ramon, CA (US)

(72) Inventors: Neil Padharia Ray, Sacramento, CA (US); Mark Andrew Rosen, Piedmont, CA (US); Adam Jacobs, Hollis, NH (US); Nevan Hanumara, Cambridge, MA (US)

(73) Assignee: Raydiant Oximetry, Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/790,940

(22) Filed: Jul. 31, 2024

(65) Prior Publication Data

US 2025/0032012 A1     Jan. 30, 2025

Related U.S. Application Data

(63) Continuation of application No. 16/958,133, filed as application No. PCT/US2018/068049 on Dec. 28, 2018, now Pat. No. 12,076,139.

(Continued)

(51) Int. Cl.
A61B 5/1455     (2006.01)
A61B 5/00     (2006.01)
(Continued)

(52) U.S. Cl.
CPC .......... *A61B 5/14551* (2013.01); *A61B 5/004* (2013.01); *A61B 5/1075* (2013.01);
(Continued)

(58) Field of Classification Search
CPC ..... A61B 5/14551; A61B 5/004; A61B 5/055; A61B 5/1075; A61B 5/1079;
(Continued)

(56) References Cited

U.S. PATENT DOCUMENTS 4,911,167 A     3/1990   Corenman et al.
5,348,002 A     9/1994   Caro
(Continued)

FOREIGN PATENT DOCUMENTS

CN     103381094 A     11/2013
EP     1054620 B1     1/2010
(Continued)

OTHER PUBLICATIONS

Delpy, et al., "Quantification in tissue near-infrared spectroscopy," Phil. Trans. R. Soc. Lond. B, 352: 649-659, 1997.
(Continued)

*Primary Examiner* — Alexei Bykhovski
(74) *Attorney, Agent, or Firm* — Resonance IP Law, PC

(57) ABSTRACT

A system and/or device for transabdominal fetal oximetry and/or fetal pulse oximetry and/or uterine tone determination may include one or more articulating, adjustable, and/or selectable components such as a light source and/or a photodetector. In some embodiments, the positioning of a light source and/or detector may be adjustable. The articulation and/or adjustment of position of the light source and/or photodetector may be in any plane (X, Y, and/or Z) and, in some instances, may be responsive to a fetal position within a maternal abdomen. Light detected by the detectors may be used to determine a fetal hemoglobin oxygen
(Continued)

1800 saturation level and/or a muscular state (e.g., contracted or relaxed) of the pregnant mammal's uterus.

10 Claims, 45 Drawing Sheets

Related U.S. Application Data

(60) Provisional application No. 62/611,830, filed on Dec. 29, 2017.

(51) Int. Cl.

| | |
|---|---|
| *A61B 5/055* | (2006.01) |
| *A61B 5/107* | (2006.01) |
| *A61B 5/1464* | (2006.01) |
| *A61B 8/08* | (2006.01) |

(52) U.S. Cl.
CPC .......... *A61B 5/1079* (2013.01); *A61B 5/1464* (2013.01); *A61B 5/742* (2013.01); *A61B 8/0866* (2013.01); *A61B 2503/02* (2013.01)

(58) Field of Classification Search
CPC ..... A61B 5/1464; A61B 5/742; A61B 8/0866; A61B 2503/02; A61B 8/02; A61B 8/4209; A61B 5/14552; A61B 5/6835; A61B 8/4416; A61B 5/1072; A61B 5/1455
See application file for complete search history.

(56) References Cited

U.S. PATENT DOCUMENTS

| | | | |
|---|---|---|---|
| 5,807,271 | A | 9/1998 | Tayebi et al. |
| 5,835,558 | A | 11/1998 | Maschke |
| 6,498,942 | B1 | 12/2002 | Esenaliev et al. |
| 6,690,958 | B1 | 2/2004 | Walker et al. |
| 7,047,055 | B2 | 5/2006 | Boas et al. |
| 7,469,158 | B2 | 12/2008 | Cutler et al. |
| 7,515,948 | B1 | 4/2009 | Balberg et al. |
| 8,275,436 | B2 | 9/2012 | Wang et al. |
| 8,644,900 | B2 | 2/2014 | Balberg et al. |
| 9,757,058 | B2 | 9/2017 | Ray |
| 9,968,286 | B2 | 5/2018 | Ray |
| 10,362,974 | B2 | 7/2019 | Ray |
| 2003/0073910 | A1 | 4/2003 | Chance |
| 2004/0116789 | A1 | 6/2004 | Boas et al. |
| 2006/0122475 | A1 | 6/2006 | Balberg et al. |
| 2007/0078311 | A1 | 4/2007 | Al-Ali et al. |
| 2008/0208009 | A1 | 8/2008 | Shklarski |
| 2009/0281402 | A1 | 11/2009 | Chance |
| 2010/0081901 | A1 | 4/2010 | Buice et al. |
| 2011/0152688 | A1* | 6/2011 | Venugopalan ....... A61B 8/4227 |
| | | | 600/453 |
| 2011/0218413 | A1 | 9/2011 | Wang et al. |
| 2012/0190946 | A1 | 7/2012 | Bernreuter |
| 2013/0281803 | A1* | 10/2013 | Scheele .............. A61B 5/14551 |
| | | | 600/323 |
| 2013/0338460 | A1 | 12/2013 | He et al. |
| 2015/0099950 | A1 | 4/2015 | Al-Ali et al. |
| 2016/0015304 | A1 | 1/2016 | Esenaliev et al. |
| 2016/0128594 | A1 | 5/2016 | Amir et al. |
| 2017/0188920 | A1* | 7/2017 | Ray ..................... A61B 5/1482 |
| 2018/0070871 | A1 | 3/2018 | Ray |
| 2019/0076195 | A1* | 3/2019 | Shalayev .............. A61B 34/10 |
| 2019/0343437 | A1 | 11/2019 | Ray |

FOREIGN PATENT DOCUMENTS

| | | | |
|---|---|---|---|
| WO | 2004086966 | A1 | 10/2004 |
| WO | 2009032168 | A1 | 3/2009 |
| WO | 2018094391 | A3 | 7/2018 |

OTHER PUBLICATIONS

Dildy, "Fetal Pulse Oximetry," Clinical Obstetrics and Gynecology, 54(1): 66-73, Mar. 2011.
Dildy, et al., "Current status of the multicenter randomized clinical trial on fetal oxygen saturation monitoring in the United States," European Journal of Obstetrics & Gynecology and Reproductive Biology, 72, Suppl. 1, pp. S43-S50, 1997.
Dildy, et al., "Intrapartum fetal pulse oximetry: Fetal oxygen saturation trends during labor and relation to delivery outcome," Am. J. Obstet. Gynecol., 171(3): 679-684, Sep. 1994.
Dildy, et al., "Intrapartum fetal pulse oximetry: Past, present, and future," American Journal of Obstetrics & Gynecology, 175(1): 1-9, Jul. 1996.
Dildy, et al., "Management of prolonged decelerations," OBG Management, 7 pgs., Nov. 2006.
Dildy, et al., "Preliminary Experience with Intrapartum Fetal Pulse Oximetry in Humans," Obstetrics and Gynecology, 81(4): 630-635, Apr. 1993.
Diniz, In Adaptive Filtering Algorithms and Practical Implemetation, Springer, Third Edition, pp. 636, 2008.
Dong, et al., "Simultaneously Extracting Multiple Parameters Via Fitting One Single Autocorrelation Function Curve in Diffuse Correlation Spectroscopy," IEEE Transactions on Biomedical Engineering, 60(2): 361-368, Feb. 2013.
Donlon, et al., "MEG Visual Stimuli Software," MEG Setup Documentation, pp. 3.
Durduran, et al., "Diffuse correlation spectroscopy for non-invasive, micro-vascular cerebral bloodflow measurement," NeuroImage, 85: 51-63, 2014.
Durduran, et al, "Diffuse optics for tissue monitoring and tomography," Reports on Progress in Physics, 73, pp. 44, 2010.
East, et al., "A cost-effectiveness analysis of the intrapartum fetal pulse oximetry multicentre randomised controlled trial (the FOREMOST trial)," BJOG An International Journal of Obstetrics and Gynaecology, pp. 1080-1087, 2006.
East, et al., "Fetal oxygen saturation and uterine contractions during labor," Am J Perinatol, 15(6): 345-349, Jun. 1998 (Abstract Only).
East, et al., "Fetal oxygen saturation during maternal bearing down efforts in the second stage of labor," Am J. Perinatol, 15(2): 121-124, 1998 (Abstract Only).
East, et al., "Fetal Oxygen Saturation Monitoring in Labour: An Analysis of 118 Cases," Aust. and NZ Journal of Obstetrics and Gynaecology, 37(4): 397-401, 1997.
East, et al., "Fetal pulse oximetry for fetal assessment in labour (Review)," The Cochrane Collaboration, pp. 76, 2014.
East, et al., "Intrapartum fetal scalp lactate sampling for fetal assessment in the presence of a non-reassuring fetal heart rate trace (Review)," The Cochrane Database of Systematic Reviews 2015, Issue 5. Art. No. CD006174, pp. 39, 2015.
East, et al., "Intrapartum Oximetry of the Fetus," Anesthesia & Analgesia, 105(6), pp. S59-S65, Dec. 2007.
East, et al., "The effect of intrapartum fetal pulse oximetry, in the presence of a nonreassuring fetal heart rate pattern, on operative delivery rates: A multicenter, randomized, controlled trial (the FOREMOST trial)," American Journal of Obstetrics and Gynecology, 194, pp. 606.e1-606.e16, 2006.
East, et al., "Update on intrapartum fetal pulse oximetry," Aust NZ J Obstet Gynaecol, 42(2): 119-124, 2002.
Eden, et al., "Reengineering Electronic Fetal Monitoring Interpretation: Using the Fetal Reserve Index to Anticipate the Need for Emergent Operative Delivery," Reproductive Sciences, 25(4): 487-497, 2018.
Eden, et al., "The "Fetal Reserve Index": Re-Engineering the Interpretation and Responses to Fetal Heart Rate Patterns," Fetal Diagnosis and Therapy, 43: 90-104, Jun. 2017.
Emberson, et al., "Isolating the effects of surface vasculature in infant neuroimaging using short-distance optical channels: a combination of local and globaleffects," Neurophotonics, 3(3), pp. 031406-1-031406-12, Jul.-Sep. 2016.
Eunson, "The long-term health, social, and financial burden of hypoxic-ischaemic encephalopathy," Developmental Medicine & Child Neurology, 57 (Suppl. 3): 48-50, 2015.

(56)　　　　　References Cited

OTHER PUBLICATIONS

Evans, et al., "Re-engineering the interpretation of electronic fetal monitoring to identify reversible risk for cerebral palsy: a case control series," The Journal of Maternal-Fetal & Neonatal Medicine, pp. 10, 2018.

Fabbri, et al., "Optical measurements of absorption changes in two-layered diffusive media," Physics in Medicine & Biology, 49: 1183-1201, Mar. 18, 2004.

Fantini, et al., "Frequency-domain multichannel optical detector for noninvasive tissue spectroscopy and oximetry," Optical Engineering, 34(1): 32-42, Jan. 1995.

Fantini, et al., "Frequency-domain techniques for tissue spectroscopy and imaging", In Handbook of Optical Biomedical Diagnostics, Second Edition, vol. 1: Light Tissue Interaction, Chapter 7, pp. 1-52, 2002.

Farrell, et al., "Influence of layered tissue architecture on estimates of tissue optical properties obtained from spatially resolved diffuse reflectometry," Applied Optics, 37(10): 1958-1972, Apr. 1, 1998.

Farzam, "Hybrid diffuse optics for monitoring of tissue hemodynamics with applications in oncology," Doctoral Thesis in Photonics, Institute of Photonic Sciences, pp. 240, Jul. 2014.

Fatemi, et al., "Hypoxic Ischemic Encephalopathy in the Term Infant," Author manuscript; available in PMC, Dec. 1, 2010, pp. 23, 2009.

Figures of Two-minute tracing showing fetal heart rate, and Pulse oximetry tracing from 25-week gestation fetus undergoing open congenital diaphragmatic hernia repair, Anesthesia for Fetal Procedures and Surgery, pp. 280-281.

Firbank, et al., "An investigation of light transport through scattering bodies with non-scattering regions," Phys. Med. Biol., 41: 767-783, 1996.

Fong, D.D., et al., "Contextually-aware Fetal Sensing in Transabdominal Fetal Pulse Oximetry," 2020 ACM/IEEE 11th International Conference on Cyber-Physical Systems (ICCPS), Apr. 2020.

Fong, D.D., et al., "Optode Design Space Exploration for Clinically-robust Non-invasive Fetal Oximetry," ACM Transactions on Embedded Computing Systems, vol. 18, No. 5s, Article 63, Oct. 2019.

Fong, et al., "Recovering the Fetal Signal in Transabdominal Fetal Pulse Oximetry," Smart Health, 9-10: 23-26, Jul. 9, 2018.

Fong, et al., "Transabdominal Fetal Blood Oximetry," Website of the University of California, Davis, Office of Research, http://research.ucdavis.edu/u/s/ia, pp. 1, 2017.

Fong, et al., "Transabdominal Fetal Pulse Oximetry: The Case of Fetal Signal Optimization," 2017 IEEE 19th International Conference on e-Health Networking, Applications and Services (Healthcom), pp. 6, 2017.

Franceschini, et al., "Assessment of Infant Brain Development with Frequency-Domain Near-Infrared Spectroscopy," Pediatr Res., 61(5): 546-551, 2007.

Franceschini, et al., "Influence of a superficial layer in the quantitative spectroscopic study of strongly scattering media," Applied Optics, 37(31): 7447-7458, Nov. 1, 1998.

Gagnon, et al., "Further improvement in reducing superficial contamination in NIRS using doubleshort separation measurements," NeuroImage, 85: 127-135, 2014.

Gagnon, et al., "Short separation channel location impacts the performance of short channel regression in NIRS," NeuroImage, 59: 2518-2528, 2012.

Ganesan et al., "Diffuse optical spectroscopic imaging of subcutaneous adipose tissue metabolic changes during weight loss," Int J Obes (Lond). Aug. 2016 ; 40(8). Author Manuscript available in PMC Oct. 22, 2016. pp. 1292-1300, Oct. 2016.

Gardner, et al., "Enhanced Umbilical Blood Flow During Acute HypoxemiaAfter Chronic Umbilical Cord Compression, A Role for Nitric Oxide," Basic Science Reports in Circulation, pp. 331-335, Jun. 30, 2003.

Gardosi, et al., "Adaptation of pulse oximetry for fetal monitoring during labour," The Lancet, 337: 1265-1267, May 25, 1991.

Gardosi, et al., "Continuous Intrapartum Monitoring Offectal Oxygen Saturation," The Lancet, Sep. 16, 1989, pp. 692-693.

Garite, et al., "Transactions of the Twentieth Annual Meeting of the Society for Maternal-Fetal Medicine—Continued," American Journal of Obstetrics and Gynecology, 183(5): 1049-1058, Nov. 2000.

Ghiasi, et al., "Transabdominal Fetal Oximetry, Project conducted at the Laboratory for Embedded and Programmable Systems," (LEPS), pp. 1-4.

Giordano, "New ANSI guidelines remind users to take stock of industrial laser protections," Laser Focus World, 50(10):41-43+47 • Oct. 2014.

Goodlin, "Preliminary experience with intrapartum fetal pulse oximetry in humans," Obstetrics and Gynecology, 82(2): 314-315, Jul. 31, 1993.

Graham, et al.,"A systematic review of the role of intrapartum hypoxia-ischemia in the causation of neonatal encephalopathy," American Journal of Obstetrics & Gynecology, pp. 587-595, Dec. 2008.

Greene, "Obstetricians Still Await a Deus ex Machina," The New England Journal of Medicine, 355: 2247-2248, Nov. 23, 2006.

Gregg, et al., "Brain specificity of diffuse optical imaging: improvements from superficial signal regression and tomography," Frontiers in NeuroEnergetics, 2(13), pp. 1-8, Jul. 14, 2010.

Grimes, et al., "Electronic Fetal Monitoring as a Public Health Screening Program: The Arithmetic of Failure," Obstetrics & Gynecology, 116(6): 1397-1400, Dec. 2010.

Gunn, et al., "Fetal Hypoxia Insults and Patterns of Brain Injury: Insights from Animal Models," Clin Perinatol, 36: 579-593, 2009.

Harini, et al., "Design and Implementation of a Calibration-Free Pulse Oximeter", In: Goh J. (eds) The 15th International Conference on Biomedical Engineering. IFMBE Proceedings, vol. 43, Springer, Cham, pp. 100-103, 2014.

Haydon, et al., "The effect of maternal oxygen administration on fetal pulse oximetry during labor in fetuses with nonreassuring fetal heart rate patterns," American Journal of Obstetrics and Gynecology, 195: 735-738, 2006.

Haykin, In Kalman Filtering and Neural Networks, Ed. Simon Haykin, John Wiley & Sons, Inc., New York, NY, pp. 298, 2001.

Hiraoka, et al., "A Monte Carlo investigation of optical pathlength in inhomogeneous tissue and its application to near-infrared spectroscopy," Institute of Physics and Engineering in Medicine, 38: 1859-1876, 1993.

Hyvärinen, "Fast and Robust Fixed-Point Algorithms for Independent Component Analysis," IEEE Trans. on Neural Networks, 10(3): 626-634, 1999.

International Commission on Non-Ionizing Radiation Protection (ICNIRP), "ICNIRP Guidelines on Limits of Exposure to Incoherent Visible and Infrared Radiation," Health Physics, 105(1): 74-96; 2013.

International Search Report and the Written Opinion of the International Searching Authority for International Application No. PCT/US19/40639 dated Nov. 12, 2019.

International Search Report and the Written Opinion of the International Searching Authority for International Application No. PCT/US2017/062782, dated Feb. 19, 2018.

International Search Report and Written Opinion mailed Mar. 13, 2017, from the International Searching Authority, for International Patent Application No. PCT/US2016/068994 (filed Dec. 28, 2016), 13 pages.

Jacques, "Corrigendum: Optical properties of biological tissues: a review," IOP Publishing, Phys. Med. Biol. 58: 5007-5008, Jun. 27, 2013.

Jacques, "Optical properties of biological tissues: a review," IOP Publishing, Phys. Med. Biol. 58: R37-R61, May 10, 2013.

Jezewski, et al., "Extraction of Fetal Heart-Rate Signal as the Time Event Series From Evenly Sampled Data Acquired Using Doppler Ultrasound Technique, IEEE Transactions on Biomedical Engineering," 55(2): 805-810, Feb. 2008.

Johnson et al., "Continuous fetal monitoring with a pulse oximeter: a case of cord compression," Am. J. Obstet. Gynecol., 161(5): 1295-1296, Nov. 1989 (Abstract Only).

Johnson, et al., "Continuous Intrapartum Measurement of Fetal Oxygen Saturation," The Lancet, pp. 517, Aug. 27, 1988.

Johnson, et al., "Fetal monitoring with pulse oximetry," British Journal of Obstetrics and Gynaecology, 98: 36-41, Jan. 1991.

(56)　　　　References Cited

OTHER PUBLICATIONS

Julious, "Sample size of 12 per group rule ofthumb for a pilot study," Pharmaceut. Statist., 4: 287-291, 2005.

Jumadi, et al., Development of theoretical oxygen saturation calibration curve based on optical density ratio and optical simulation approach,: AIP Conference Proceedings 1883, pp. 1-11, Sep. 14, 2017.

Jumadi, et al., "Investigating the Effect of Total Radiated Power on Fetus Using Optical Simulation Approach Based on Exposure Safety Limit for Eye and Tissue Injury," Journal of Life Sciences and Technologies, 2(1): 24-27, Jun. 2014.

Jumadi, et al., "Transabdominal Fetal Pulse Oximeter Using LEDs and Photodiode: A Design Consideration Study," 2015 2nd International Conference on Biomedical Engineering (ICoBE), pp. 1-6, Mar. 30-31, 2015.

Jurovata, et al., "Simulation of Photon Propagation in Tissue Using Matlab", Faculty of Materials Science and Technology in Trnava Slovak University of Techology in Bratislava, Research Papers (2013), 21:31-37.

Kainerstorfer, et al., "Optical oximetry of volume-oscillating vascular compartments: contributions from oscillatory blood flow," Journal of Biomedical Optics, 21(10): pp. 101408-1-101408-13, Oct. 2016.

Kelly, et al., "Dose-dependent relationship between acidosis at birth and likelihood of death or cerebral palsy," Arch Dis Child Fetal Neonatal Ed 2017, pp. F1-F6, 2017.

Kim, et al., "Noise reduction of PPG signal during Free Movements Using Adaptive SFLC (scaled Fourier linear combiner)," IFMBE proceedings, pp. 1083-1086, Jan. 2007.

Kirschbaum, et al., "Oxyhemoglobin dissociation characteristics of human and sheep maternal and fetal blood," Am. J. Obstetric and Gynecology, 96(5): 741-759, 1966.

Klauser, et al., "Use of fetal pulse oximetry among high-risk women in labor: A randomized clinical trial," American Journal of Obstetrics and Gynecology, 192: 1810-1817, 2005.

Kohl, et al., "Determination of the wavelength dependence of the differential pathlength factor from near-infrared pulse signals," Physics in Medicine & Biology, 43: 1771-1782, 1998.

Komalla, "A new method based on complex EMD for motion artifacts reduction in PPG signals for pulse oximeter application," Journal of Engineering Technology, Special Issue on Technology Applications and Innovations, 6: 187-200, 2017.

Konugolu Venkata Sekar, "Broadband Time-Domain Disffuse Optics for Clinical Diagnostics and Diffuse Raman Spectroscopy," Doctoral Dissertation, Politecnico de Milano, Physics Department, pp. 1-288, 2016.

Kuhnert, et al., "Intrapartum management of nonreassuring fetal heart rate patterns: A randomized controlled trial of fetal pulse oximetry," American Journal of Obstetrics and Gynecology, 191: 1989-1995, 2004.

Lakowicz, et al., "Frequency-Domain Measurements of Photon Migration in Tissues," Chemical Physics Letters, 166(3): 246-252, Feb. 23, 1990.

Laqua, et al., "A phantom with pulsating artificial vessels for non-invasive fetal pulse oximetry", Conf Proc IEEE Eng Med Biol Soc., pp. 5631-5634, 2014.

Laqua, et al., "FPGA controlled artificial vascular system," Current Directions in Biomedical Engineering, 1: 446-449, 2015.

Laqua, et al., "Improved FPGA controlled artificial vascular system for plethysmographic measurements", Current Directions in Biomedical Engineering, 2(1): 689-693, 2016.

Larosa, et al., "Understanding the full Spectrum of Organ Injury Following Intrapartum Asphixia," Frontiers in Pediatrics, 5(16): 1-11, Feb. 17, 2017.

Larsen, "Pulse Oximetry Devices Market," Meddevicetracker, Pharma Intelligence, pp. 1-58, Dec. 2017.

Lear, et al., "The peripheral chemoreflex: indefatigable guardian offetal physiological adaptation to labour," The Journal of Physiology, pp. 1-13, 2018.

Lemieux, et al., "Investigating non-Gaussian scattering processes by using nth-order intensity correlation functions," 16(7): 1651-1664, Jul. 1999.

Leszczynska-Gorzelak, et al., "Intrapartum cardiotocography and fetal pulse oximetry in assessing fetal hypoxia," International Journal of Gynecology & Obstetrics, 76: 9-14, 2002.

Louie, et al., "Four Types of Pulse Oximeters Accurately Detect Hypoxia during Low Perfusion and Motion," Anesthesiology, pp. 1-11, 2017.

Luttkus, et al., "Pulse oximetry during labour—does it give rise to hope? Value of saturation monitoring in comparison to fetal blood gas status," European Journal of Obstetrics & Gynecology and Reproductive Biology, 110, pp. S132-S138, 2003.

Mallinckrodt, Inc., "(N-400) Fetal Oxygen Saturation Monitoring System," Summary of Safety and Effectivenes Information Data, p. 31, 2000.

Mannheimer, et al., "Wavelength Selection for Low-Saturation Pulse Oximetry," IEEE Transactions on Biomedical Engineering, 44(3): 148-158, Mar. 1997.

Martinek, et al., "Non-Invasive Fetal Monitoring: A Maternal Surface ECG Electrode Placement-Based Novel Approach for Optimization of Adaptive Filter Control Parameters Using the LMS and RLS Algorithms," Sensors, 17: 1154, pp. 1-32, May 19, 2017.

Martinello, et al., "Management and investigation of neonatal-encephalopathy: 2017 update," Arch Dis Child Fetal Neonatal , 102: pp. F346-F-358, 2017.

Mawn, et al., "Trans-abdominal Monitoring of Fetal Arterial Oxygen Saturation Using Pulse Oximetry," IEEE EMBS—NEBE, 227-228, 2002.

Mcnamara, et al., "Continuous intrapartum pH, pO2, pCO2, and SpO2 monitoring," Obstet Gynecol Clin North Am, 26(4): 671-693, Dec. 1999.

Meschia, et al., "A Comparison of the Oxygen Dissociation Curves of the Bloods of Maternal, Fetal and Newborn Sheep at Various pHs," In: Oxgen Dissociation Curves in Sheep at Various pHs, pp. 95-97, Sep. 23, 1960.

Mesquita, et al., "Direct measurement of tissue blood flow and metabolism with diffuse optics," Philosophical Transactions of The Royal Society A, 369: 4390-4403, 2011.

Miller, "Raydiant Oximetry: Provides Crucial Comfort for New Mothers," MedTech Strategist, 5(4), pp. 2, Mar. 27, 2018.

Molavi, et al., "Motion Artifact Removal from Muscle NIR Spectroscopy Measurements," Conference paper in Canadian Conference on Electrical and Computer Engineering, pp. 1-5, May 2010.

Mourant, et al., "Mechanisms of light scattering from biological cells relevant to noninvasive optical-tissue diagnostics," Applied Optics, 37(15): 3586-3593, Jun. 1, 1998.

Nasiriavanaki, et al., "High-resolution photoacoustic tomography of resting-state functional connectivity in the mouse brain," PNAS, 111(1): 21-26, Jan. 7, 2014.

Nelson, et al., "Electronic fetal monitoring, cerebralpalsy, and caesarean section: assumptions versus evidence," BMJ, 355: pp. 1-3, Dec. 1, 2016.

Nioka, et al., "Fetal transabdominal pulse oximeter studies using a hypoxic sheep model," The Journal of Maternal-Fetal and Neonatal Medicine, 17(6): 393-399, Jun. 2005.

Nitzan, et al., "Calibration-Free Pulse Oximetry Based on Two Wavelengths in the Infrared—A Preliminary Study," Sensors 2014, 14: 7420-7434, Apr. 23, 2014.

Nonnenmacher, et al., "Predictive value of pulse oximetry for the development of fetal acidosis," J. Perinat. Med, 38: 83-86, 2010.

Noren, et al., "Reduced prevalence of metabolic acidosis at birth: an analysis of established STAN usage in the total population of deliveries in a Swedish district hospital," American Journal of Obstetrics & Gynecology, 202, pp. 546.e1-546.e7, Jun. 2010.

Novak, et al., "Perinatal Brain Injury Mechanisms, Prevention, and Outcomes," Clin Pernatol, 45: 357-375, 2018.

OBG Project, "Which Fetal Heart Monitoring Parameters Best Predict Fetal Acidemia?," https://www.obgproject.com/category/grandrounds/) pp. 1-2, date unknown.

Office Action mailed Feb. 1, 2018, from the Taiwan Intellectual Property Office, for Taiwan Patent Application No. 105143848, 17 pages.

(56) References Cited

OTHER PUBLICATIONS

Olutoye, et al., "Food and Drug Administration warning on anesthesia and brain development: implications for obstetric and fetal surgery," American Journal of Obstetrics & Gynecology, pp. 98-102, Jan. 2018.

Patient Safety Movement Foundation, "Actionable Patient Safety Solution (APSS) #11C: Reducing Unnecessary C-Sections," 2018 Patient Safety Movement Foundation, pp. 1-8, Aug. 15, 2018.

PCT International Search Report and the Written Opinion of the International Searching Authority for International Application No. PCT/US2018/068049 dated Apr. 26, 2019.

PCT International Search Report, International Searching Authority, for International Patent Application No. PCT/US2017/062782 filed on Nov. 21, 2017, pp. 1 to 4, Feb. 19, 2018.

PCT/US2018/068042 International Search Report and Written Opinion, Apr. 26, 2019, 16 pages.

PCT/US2018/068049 International Search Report and Written Opinion, Apr. 26, 2019, 20 pages.

Peat, et al., "Continuous intrapartum measurement of fetal oxygen saturation," The Lancet, Jul. 23, 1988, pp. 213.

Peebles, et al., "Effect of oxytocin on fetal brain oxgenation during labour," The Lancet, 338: 254-255, Jul. 27, 1991.

Peek, et al., "Fetal Pulse Oximetry and Cesarean Delivery," The New England Journal of Medicine, 356: 1377-1378, Mar. 29, 2007.

Pereira, et al., "Recognition of chronic hypoxia and pre-existing foetal injury on the cardiotocograph (CTG): Urgent need to think beyond the guidelines," Porto Biomedical Journal, 2(4): 124-129, 2017.

Peters, et al., "Beat-to-beat detection of fetal heart rate: Doppler ultrasound cardiotocography compared to direct ECG cardiotocography in time and frequency domain," Physiological Measurement, 25: 585-593, 2004.

Phelan, et al., "Fetal Heart Rate Observations in the Brain-Damaged Infant," Seminars in Perinatology, 24(3): 221-229, Jun. 2000.

Philips proprietary camera based monitoring technology is first in the world to measure absolute arterial blood oxygenation (SpO2) levels without ever touching the patient, Jun. 6, 2016, 4 pages (https://www.usa.philips.com/a-w/about/news/archive/standard/news/press/2016/20160606-philips-proprietary-camera-based-monitoring-technology-is-first-in-the-world-to-measure-absolute-arterial-blood-oxygenation-levels-without-ever-touching-the-patient.html) Jun. 6, 2016.

Pifferi, et al., "Real-time method for fitting time-resolved relectance and transmittance measurements with a Monte Carlo model," Applied Optics, 37(13): 2774-2776, May 1, 1998.

Porreco, et al., "Dystocia in nulliparous patients monitored with fetal pulse oximetry," American Journal of Obstetrics and Gynecology, 190: 113-117, 2004.

Ragozzino, et al., "Average Fetal Depth in Utero: Data for Estimation of Fetal Absorbed Radiation Dose," Radiology, 158(2): 513-515, 1986.

Ramanujam, et al., "Antepartum, Transabdominal Near Infrared Spectroscopy: Feasibility of Measuring Photon Migration Through the Fetal Head In Utero," The Journal of Maternal-Fetal Medicine, 8: 275-288, 1999.

Ramanujam, et al., "Photon migration through fetal head in utero using continuous wave, near infrared spectroscopy," Journal of Biomedical Optics, 5(2): 173-184, Apr. 2000.

Rei, et al., "Neurological damage arising from intrapartum hypoxia/acidosis," Best Practice & Research Clinical Obstetrics and Gynaecology, 30: 79-86, 2016.

Ren, et al., "Quasi-simultaneous multimodal imaging of cutaneous tissue oxygenation and perfusion," Journal of Biomedical Optics, 20(12): pp. 121307-1 thru 121307-10, Dec. 2015.

Reuss, "Factors Influencing Fetal Pulse Oximetry Performance," Journal of Clinical Monitoring and Computing, 18: 13-24, 2004.

Reuss, "Multilayer Modeling of Reflectance Pulse Oximetry," IEEE Transactions on Biomedical Engineering, 52(2): 153-159, Feb. 2005.

Reuss, et al., "The pulse in reflectance pulse oximetry: modeling and experimental studies," Journal of Clinical Monitoring and Computing, 18: 289-299, 2004.

Rivolta, et al., "Acceleration and Deceleration Capacity of Fetal Heart Rate in an In-Vivo Sheep Model," PLOS One, 98(8): 1-10, Aug. 2014.

Roche-Labarbe, et al., "Noninvasive Optical Measures of CBV, StO2, CBF Index, and rCMRO2in Human Premature Neonates' Brains in the First Six Weeks of Life," Human Brain Mapping, 31: 341-352, 2010.

Roemer, et al., "Sensitivity, specificity, receiver•-operating characteristic (ROC) curves and likelihood ratios for electronic foetal heart rate monitoring using new evaluation techniques," Z Geburtshilfe Neonatol, 214(3): 108-118, Jun. 2010 (Abstract Only).

Ross, "Labor and Fetal Heart Rate Decelerations: Relation to Fetal Metabolic Acidosis," Clinical Obstetrics and Gynecology, 54(1): 74-82, 2011.

Roth, et al., "Unequal Motherhood: Racial-Ethnic and Socioeconomic Disparities in Cesarean Sections in the United States," Social Problems, 59(2): 207-227, May 2012.

Saager, et al., "Direct characterization and removal of interfering absorption trends in two-layer turbid media," J. Opt. Soc. Am. A, 22(8): 1874-1882, Sep. 2005.

Sabiani, et al., "Intra- and interobserver agreement among obstetric experts in court regarding the review of abnormal fetal heart rate tracings and obstetrical management," American Journal of Obstetrics & Gynecology, 213(6): pp. 856.e1 thru 856.e8, Dec. 2015.

Saccone, et al., "Electrocardiogram ST Analysis During Labor A Systematic Review and Meta-analysis of Randomized Controlled Trials," Obstetrics & Gynecology, 127(1): 127-135, Jan. 2016.

Salamalekis, et al., "Computerised intrapartum diagnosis of fetal hypoxia based on fetal heart rate monitoring and fetal pulse oximetry recordings utilising wavelet analysis and neural networks," BJOG: an International Journal of Obstetrics and Gynaecology, 109: 1137-1142, Oct. 2002.

Salamalekis, et al., "Fetal pulse oximetry and wavelet analysis of the fetal heart rate in the evaluation of abnormal cardiotocography tracings," J. Obstet. Gynaecol. Res., 32(2): 135-139, Apr. 2006.

Sartwelle, et al., "A half century of electronic fetal monitoring and bioethics: silence speaks louder than words," Maternal Health, Neonatology, and Perinatology, 3:(21): 1-8, 2017.

Sartwelle, et al., "The Ethics of Teaching Physicians Electronic Fetal Monitoring: And Now for the Rest of the Story," Surg J, 3: pp. e42 thru e-47, 2017.

Sassaroli, et al., "Comment on the modified Beer-Lambert law for scattering media," Physics in Medicine & Biology, 49(14): pp. N255 thru N257, Jul. 5, 2004.

Schiermeier, et al., "Sensitivity and specificity of intrapartum computerised FIGO criteria for cardiotocography and fetal scalp pH during labour: multicentre, observational study," BJOG An International Journal of Obstetrics and Gynaecology, pp. 1557-1563, Aug. 26, 2008.

Schweiger, et al., "Near-infrared imaging: photon measurement density functions," Proc. SPIE, 2389: 366-377, May 30, 1995.

Seelbach-Göbel, et al., "The prediction of fetal acidosis by means of intrapartum fetalpulse oximetry," American Journal of Obstetrics and Gynecology, 180(1): 73-81, Jan. 1999.

Severinghaus, et al., "History of Blood Gas Analysis. VII. Pulse Oximetry," Journal of Clinical Monitoring, 3(2): 135-138, Apr. 1987.

Shang, et al., "Portable optical tissue flow oximeter based on diffuse correlation spectroscopy," Optics Letters, 34(22): 3556-3558, Nov. 15, 2009.

Siristatidis, et al., "Alterations in Doppler velocimetry indices of the umbilical artery during fetal hypoxia in labor, in relation to cardiotocography and fetal pulse oximetry findings," Arch Gynecol Obstet, 272: 191-195, 2005.

Siristatidis, et al., "Evaluation of fetal intrapartum hypoxia by middle cerebral and umbilical artery Doppler velocimetry with simultaneous cardiotocography and pulse oximetry," Arch Gynecol Obstet, 270: 265-270, 2004.

(56)         References Cited

OTHER PUBLICATIONS

Siristatidis, et al., "Intrapartum Surveillance of IUGR Fetuses with Cardiotocography and Fetal Pulse Oximetry," Biology of the Neonate, 83: 162-165, 2003.

Spector-Bagdady, et al., "Clinician Self-Interestand the Case of Electronic Fetal Monitoring," Hastings Center Report, pp. 16-24, Nov.-Dec. 2017.

Spencer, et al., "MASS Spectrometer System for Continuous Skin-Surface and Intravascular Blood Gas Measurement of Maternal-Fetal Respiration in Labour," Journal of Biomedical Engineering , 9: 161-168, Apr. 1987.

Spong, et al., "Preventing the First Cesarean Delivery: Summary of a Joint Eunice Kennedy Shriver National Institute of Child Health and Human Development, Society for Maternal-Fetal Medicine, and American College of Obstetricians and Gynecologists Workshop," American Journal of Obstetrics and Gynecology, 120(5): 1181-1193, 2012.

Steinbrink, et al., "Illuminating the BOLD signal: combined fMRI-fNIRS studies," Magnetic Resonance Imaging, 24: 495-505, 2006.

Stipcevic et al., "Characterization of a novel avalanche photodiode for single photon detection in VIS-NIR range," Optics Express, 18(16): 17448-17459, Jul. 30, 2010.

Strangman, et al., "Factors affecting the accuracy of near-infrared spectroscopy concentration calculations for focal changes in oxygenation parameters," NeuroImage, 18: 865-879, 2003.

Subramaniam, "An IR Muscle Contraction Sensor", Cornell University, student project (last modified Jun. 10, 2014), retrieved from: https://people.ece.cornell.edu/land/courses/eceprojectsland/STUDENTPROJ/2013to2014/ras578/Writeup/An%20IR%20Muscle%20Contraction%20Sensor.html, 6 pgs., Feb. 2017.

Sutin, et al., "Time-domain diffuse correlation spectroscopy," Optica, vol. 3, Issue 9, pp. 1006-1013, Sep. 2016.

Tamborini, et al., "Development and characterization of a multi distance and multi wave length diffuse correlation spectroscopy system," Neurophoton, 5(1), pp. 011015-1 thru 011015-10, Jan.-Mar. 2018.

Themelis, et al., "Near-infrared spectroscopy measurement of the pulsatile component of cerebral blood flow and volume from arterial oscillations," Journal of Biomedical Optics, 21(1), pp. 1-15, 2007.

Tomich, "Fetal heart rate monitoring," Power Point—Department of Obstetrics and Gynecology, University of Nebraska College of Medicine, (uploaded Jul. 30, 2014) 69 pages.

Torbenson, et al., "Intrapartum factors associated with neonatal hypoxic ischemic encephalopathy: a case-controlled study," BMC Pregnancy and Childbirth, 17(415): 1-7 , 2017.

Townsend, et al, "Pulse Oximetry," Medical Electronics, Michaelmas Term, 2001.

Truven Health Analytics, The cost of having a baby in the United States,: Truven Health Analytics Marketscan® Study, pp. 1 to 84, 2014.

Truven Health Analytics, The Cost of Having a Baby in the United States—Executive Summary, Truven Health Analytics Marketscan Study, pp. 5, Jan. 2013.

Tu, et al., "An Analytical Model for Optimization of Frequency-domain System," Bioengineering Conference, 2002. Proceedings of the IEEE 28th Annual Northeast, pp. 79-80, 2002.

Uchida, et al., "Reevaluation of intrapartum fetal monitoring using fetaloximetry: A review," The Journal of Obstetrics and Gynaecology Research, pp. 1-8, 2018.

Ultman, et al., "Differential Pathlength Factor for Diffuse Photon Scattering Through Tissue by a Pulse-Response Method," 107: 73-82, 1991.

Valverde, et al., "Effectiveness of pulse oximetry versus fetal electrocardiograma intrapartum evaluation of non reassuring fetal heart rate," European Journal of Obstetric and Gynecology and Reproductive Biology, 159: 333-337, 2011.

Van 'T Hooft, In "Improving evaluation of obstetric interventions," University of Amsterdam Dissertation, pp. 1-243, 2016.

Verkruysse, et al., "Calibration of Contactless Pulse Oximetry," Anesthesia & Analgesia, 124(1): 136-145, Jan. 2017.

Vidaeff, et al., "Fetal pulse oximetry: 8 vital questions," OBG Management, pp. 28-44, Mar. 2004.

Vintzileos, et al., "Transabdominal fetal pulse oximetry with near-infrared spectroscopy," American Journal of Obstetrics and Gynecology, 192: 129-133, 2005.

Vishnoi et al., "Photon migration through fetal head in utero using continuous wave, near-infrared spectroscopy: development and evaluation of experimental and numerical models", J. Biomedical Optics 5(2): 163-172, Apr. 2000.

Weyrich, et al., "Development of a Phantom to Modulate the Maternal and Fetal Pulse Curve for Pulse Oximetry Measurements," Biomed Tech 57 (Suppl. 1): 803-806, 2012.

Willmann, et al., "Small-volume frequency-domain oximetry: phantom experiments and first in vivo results," Journal of Biomedical Optics, 8(4): 618-628, Oct. 2003.

Wolfberg, "The Future of Fetal Monitoring," Reviews in Obstetrics & Gynecology, 5(3/4), pp. e132 thru e136, 2012.

Woo, et al., "Achieving higher-value obstetrical care," American Journal of Obstetrics & Gynecology, pp. 250-255 and 250.e1 thru 250.e8, Mar. 2017.

XP the Xperts in Power , 400-2500 Watts fleX, 400-2500 Watts fleXPower Series, Product information sheet, xppower.com, pp. 1 to 10, Jan. 5, 2016.

Yamaleyeva, et al., "Photoacoustic imaging for in vivo quantification of placental oxygenation in mice," The FASEB Journal, 31(12): 5520-5529, 2017.

Yamashiro, E., et al., "Fetal tolerance of maternal resuscitative endovascular balloon occlusion of the aorta in a sheep model," Am. J. Obstetrics & Genecology, Supplemental to Jan. 2020, pp. S718-S719, Jan. 2020.

Yan, et al., "Reduction of motion artifact in pulse oximetry by smoothed pseudo Wigner-Ville distribution," Journal of NeuroEngineering and Rehabilitation, 2(3), pp. 1-9, Mar. 1, 2005.

Yousefi, et al., "Adaptive Cancellation of Motion Artifact in Wearable Biosensors," 34th Annual International Conference of the IEEE EMBS, San Diego, California USA, Aug. 28-Sep. 1, 2012, pp. 5.

Yuan, et al., "Motion Artefact Minimisation from Photoplethysmography based Non-invasive Hemoglobin Sensor by the Envelope Method," Measurements, 115, pp. 1-18, Feb. 2018 (Draft Only).

Zhang, et al., "Adaptive filtering for global interference cancellation and real-time recovery of evoked brain activity: a Monte Carlo simulation study," Journal of Biomedical Optics, 12(4), pp. 044014-1 thru 044014-12, Jul./Aug. 2007.

Zhao, et al., "In vivo determination of the optical properties of infant brain using frequency-domain near-infrared spectroscopy," Journal of Biomedical Optics, 10(2), pp. 024028-1 thru 024028-7, Mar./Apr. 2005.

Zhao, et al., "Quantitative real-time pulse oximetry with ultrafast frequency frequency-domain diffuse optics and deep neural network processing," Biomedical Optics Express, 9(12): 5997-6008, 2018.

Zijistra, et al., "Absorption Spectra of Human Fetal and Adult Oxyhemoglobin, De-Oxyhemoglobin, Carboxyhemoglobin, and Methemoglobin," Clinical Chemistry, 37(9): 1633-1638, 1991.

Zourabian, et al., "Trans-abdominal monitoring of fetal arterial blood oxygenation using pulse oximetry," Journal of Biomedical Optics, 5(4): 391-405, Oct. 2000.

"Anesthesia for Fetal Procedures and Surgery," pp. 280-281.

"Assessing the Photobiological Safety of LEDs," pp. 1-8, 2012.

"Corometrics™ 250 Series Monitor Operator's Manual", GE Healthcare, Revision E (Apr. 28, 2009), 258 pgs.

"Fetal Pulse Oximetry System Clinical Use Guide", OxiFirst, Nellcor (2003), 60 pgs.

"Narrow beam LED in Dragon Dome package (850nm)", OSRAM Opto Semicondutors (Mar. 10, 2014), Version 1.3, SFH 4783, pp. 1-12.

"OSRAM Opto Semiconductors GF CSHPM1.24-3S4S-1", Mouser Electronics (accessed Dec. 2016), 2 pgs.

Aaronson, et al., "Android-Based Tocodynamometer and Fetal Heart Rate Monitor," Tocotronics (2013), 21 pgs.

Ahearne, et al., "Short and long term prognosis in perinatal asphyxia: An update," World Journal of Clinical Pediatrics, 5(1): 67-74, Feb. 8, 2016.

(56) References Cited

OTHER PUBLICATIONS

Aldrich, et al., "Late fetal heart decelerations and changes in cerebral oxygenation during the first stage of labour," British Journal of Obstetrics and Gynaecology, 102: 9-13, Jan. 1995.

Alfirevic, et al., "Continuous cardiotocography (CTG) as a form of electronicfetal monitoring (EFM) for fetal assessment during labour (Review)," Cochrane Database of Systematic Reviews 2017, Issue 2. Art. No. CD006066, pp. 1 to 56, 2017.

Amer, et al., "Xenon Combined With Hypothermia in Perinatal Hypoxic-Ischemic Encephalopathy: A Noble Gas, a Noble Mission," Pediatric Neurology, 84: 5-10, Jul. 2018.

Angelo, et al., "Review of structured light in diffuse optical imaging," Journal of Biomedical Optics 24(7), 071602 (Jul. 2019), 20 pages.

Arridge, "Inverse Problems in Optical Tomography," INI Cambridge, pp. 1-74, Aug. 24, 2011.

Arridge, "Optical tomography in medical imaging," Inverse Problems, 15: R41-R93, 1999.

Arridge, et al., "The theoretical basis for the determination of optical path lengths in tissue: temporal and frequency analysis," Physics in Medicine & Biology, 37(7): 1531-1560, 1992.

Ayres-De-Campos, "Electronic fetal monitoring orcardiotocography, 50 years later: what's in a name?," American Journal of Obstetrics & Gynecology, 218(6): 545-546, Jun. 2018.

Bansal, et al., "Wearable Organic Optoelectronic Sensors for Medicine," Advanced Materials (2014), 7 pgs.

Barry, et al., "The Pregnant Sheep as a Model for Human Pregnancy," Theriogenology, 69(1): 55-67, Jan. 1, 2008.

Bauer, et al., "Quantitative photoacoustic imaging:correcting for heterogeneous light fluence distributions using diffuse optical tomography," Journal of Biomedical Optics, 16(9): 096016-1-096016-7, Sep. 2011.

Belfort, et al., "A Randomized Trial of Intrapartum Fetal ECG ST-Segment Analysis," The New England Journal of Medicine, 373(7): 632-641, Aug. 13, 2015.

Bennet, et al., "The Cerebral Hemodynamic Response to Asphyxia and Hypoxia in the Near-term Fetal Sheep as Measured by Near Infrared Spectroscopy," Pediatric Research, 44: 951-957, Dec. 1, 1998.

Bennet, et al., "The Fetal Heart RateResponse to Hypoxia: Insights from Animal Models," Clin Perinatol, 36: 655-672, 2009.

Bevilacqua, et al., "In vivo local determination of tissue optical properties: applications to human brain," Applied Optics, 38(22): 4939-4950, 1999.

Bloom, et al., "Fetal Pulse Oximetry and Cesarean Delivery," The New England Journal of Medicine, 355: 2195-2202, Nov. 23, 2006.

Bloom, et al., "Fetal Pulse Oximetry: Duration of Desaturation and Intrapartum Outcome," Journal of Obstetrics and Gynecology, 93(6): 1036-1040, Jun. 1999.

Bloom, et al., "What We Have Learned About Intrapartum Fetal Monitoring Trials in the MFMU Network," Author Manuscript, Semin Perinatol, 40(5): 307-317, Aug. 2016.

Boas, et al., "Diffuse optical imaging of brain activation: approaches to optimizing image sensitivity, resolution, and accuracy," NeuroImage, 23: S275-S288, 2004.

Boas, et al., "Scattering and Imaging with Diffusing Temporal Fields Correlation," Physical Review Letters, 75(9): 1855-1859, Aug. 28, 1995.

Boas, et al., "Spatially varying dynamical properties of turbidmedia probed withdiffusing temporal light correlation," J. Opt. Soc. Am., 14(1): 192-215, Jan. 1997.

Bottrich, et al., "Signal Separation for Transabdominal Noninvasive Fetal Pulse Oximetry using Comb Filters," Conf Proc IEEE Eng Med Biol Soc, pp. 5870-5873, 2018.

Bozkurt, et al., "Safety assessment of near infrared light emitting diodes for diffuse optical measurements," BioMedical Engineering Online, 3(1): pp. 10, Mar. 22, 2004.

Buckley, et al., "Diffuse correlation spectroscopy formeasurement of cerebral blood flow: future prospects," Neurophotonics, 1(1), pp. 011009-1-011009-7, Jul.-Sep. 2014.

Buschmann, et al., "Fetal oxygen saturation measurement by transmission pulse oximetry," The Lancet, 339: 615, Mar. 7, 1992.

Cahill, et al., "A prospective cohort study of fetal heart rate monitoring: deceleration area is predictive of feal acidemia," American Journal of Obstetrics & Gynecology, 218(5), pp. 523.e1-523. e12, May 2018.

Caliskan, et al., "Reduction in caesarean delivery with fetal heartrate monitoring and intermittent pulse oximetryafter induction of labour with misoprostol," The Journal of Maternal-Fetal & Neonatal Medicine, 22(5): 445-451, May 2009.

Carbonne, et al, "Fetal pulse oximetry: correlation between changes in oxygen saturation and neonatal outcome. Preliminary report on 39 cases," European Journal of Obstetrics & Gynecology and Reproductive Biology, 57: 73-77, 1994.

Carbonne, et al., "Multicenter oximetry study on the clinical value of fetal pulse oximetry," Am J Obstet Gynecol, 177(3): 593-598, 1997.

Carter, et al., "Calibration of a Reflectance Pulse Oximeter in Fetal Lambs for Arterial Oxygen Saturations Below 70%," J Soc Gynecol Invest, 5(5): 255-259, Sep.-Oct. 1998.

Cerebral Palsy Guidance, Cerebral Palsy, Cerebral Palsy Guidance Website, pp. 1 to 14, 2018.

Chan, et al., "Effects of Compression on Soft Tissue Optical Properties," IEEE Journal of Selected Topics in Quantum Electronics, 2(4): 943-950, Dec. 1996.

Chandraharan, "Fetal scalp blood sampling during labour: is it auseful diagnostic test or a historical test that nolonger has a place in modern clinical obstetrics?" Royal College of Obstetricians and Gynaecologists, www.bjog.org, pp. 1056-1062, Mar. 6, 2014.

Cheung, et al., "In vivo cerebrovascular measurement combining diffuse near-infrared absorption and correlation spectroscopies," Physics in Medicine & Biology, 46: 2053-2065, 2001.

Choe, "Diffuse Optical Tomography and Spectroscopy of Breast Cancer and Fetal Brain," Pub'd, Sep. 29, 2005, A Dissertation in Physics and Astronomy, Faculties of the University of Pennsylvania.

Choe, et al., "Transabdominal near infrared oximetry of hypoxic stress in fetal sheep brain in utero," PNAS, 100(22): 12950-12954, Oct. 28, 2003.

Clark, et al., "Intrapartum management of category II fetal heart rate tracings: towards standardization of care," American Journal of Obstetrics & Gynecology, pp. 89-97, Aug. 2013.

Clark, et al., "The limits of electronic fetal heart rate monitoring in the prevention of neonatal metabolic acidemia," American Journal of Obstetrics & Gynecology, 216, pp. 163.e1-163.e6, Feb. 2017.

Colditz, et al., "Fetal pulse oximetry: Instrumentation and Recent Clinical Experience," Clinics in Perinatology, 26(4): 869-880, Dec. 1999.

Dassel, et al., "Reflectance Pulse Oximetry in Fetal Lambs," Pediatric Research, 31(3): 266-269, 1992.

De Blasi, et al., "Noninvasive measurement of human forearm oxygen consumption by near infrared spectroscopy," European Journal of Applied Physiology, 67: 20-25, 1993.

Delpy, et al., "Estimation of optical pathlength through tissue from direct time of flight measurement," Physics in Medicine & Biology, 33(12): 1433-1442, 1988.

* cited by examiner

100

100

101

103

103

100

125

125

201

300

300

400A

400B

400C

400D

400E

400F

600

601

700A

700B

700C

700D

700E

701

801

1115A    1105

1115A

802

1115C

820

1115A   1115A

803

804

1001

<table>
<tr><td>*</td><td>*</td><td>*</td><td>*</td><td>*</td><td>*</td><td>*</td><td>*</td></tr>
<tr><td>*</td><td>*</td><td>*</td><td>*</td><td>*</td><td>*</td><td>*</td><td>*</td></tr>
<tr><td>*</td><td>*</td><td>*</td><td>*</td><td>*</td><td>*</td><td>*</td><td>*</td></tr>
</table>

•   = light emitting systems 801,
802, 803, or 804

1002

•   = light emitting systems 801,
802, 803, or 804

1003

• = light emitting systems 801, 802, 803, or 804

1004

1303

• = light emitting systems 801, 802, 803, or 804

1005

• = light emitting systems 801,
802, 803, or 804

1100

1101

1111        1105

1201

• = light emitting systems 801, 802, 803, or 804

1202

• = light emitting systems 801, 802, 803, or 804

1203

• = light emitting systems 801, 802, 803, or 804

1204

•  = light emitting systems 801,
802, 803, or 804

1205

• = light emitting systems 801,
802, 803, or 804

1300

1400

1500

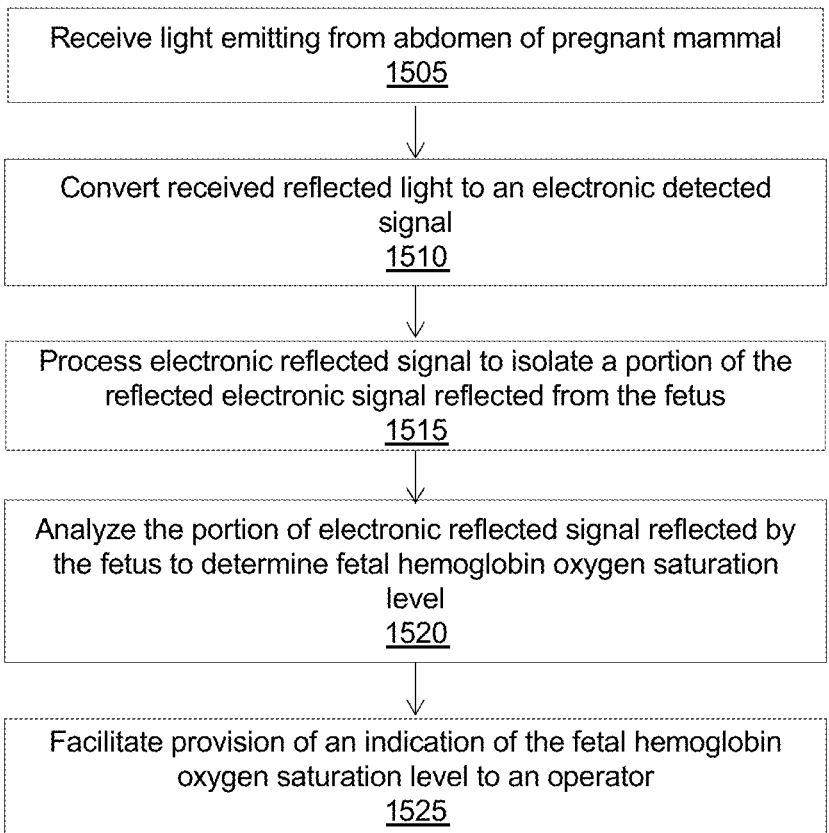

Receive light emitting from abdomen of pregnant mammal
1505

Convert received reflected light to an electronic detected
signal
1510

Process electronic reflected signal to isolate a portion of the
reflected electronic signal reflected from the fetus
1515

Analyze the portion of electronic reflected signal reflected by
the fetus to determine fetal hemoglobin oxygen saturation
level
1520

Facilitate provision of an indication of the fetal hemoglobin
oxygen saturation level to an operator
1525

Receive a signal that corresponds to an optical signal reflected from the abdomen of a pregnant mammal from a detector
1505

Isolate a portion of the received signal reflected from the pregnant mammal's uterus
1610

Perform spectroscopy analysis on the received signal
1615

Determine uterine tone
1620

Facilitate provision of an indication of uterine tone to an operator
1625

1601

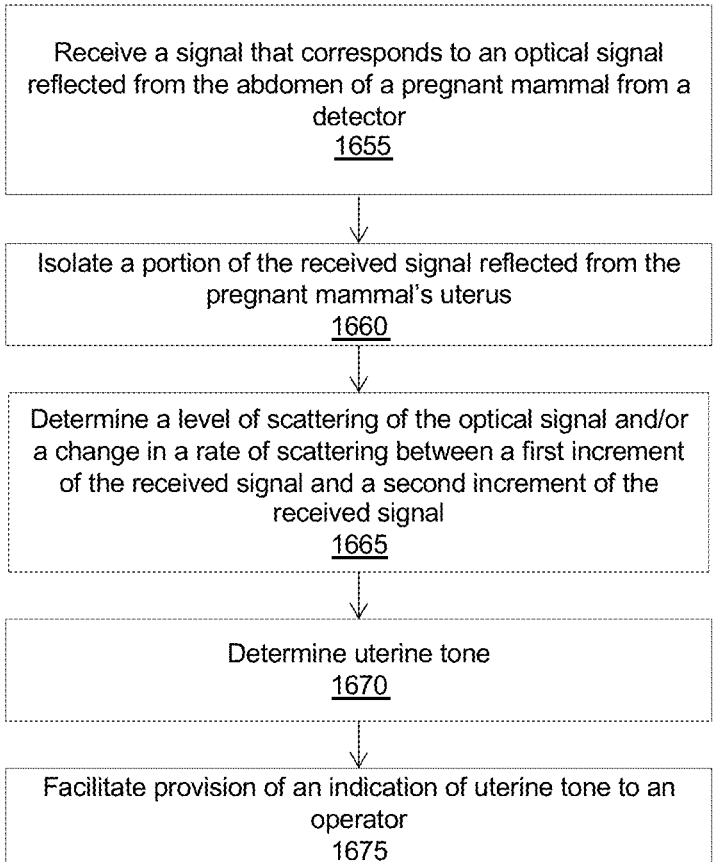

Receive a signal that corresponds to an optical signal
reflected from the abdomen of a pregnant mammal from a
detector
1655

Isolate a portion of the received signal reflected from the
pregnant mammal's uterus
1660

Determine a level of scattering of the optical signal and/or
a change in a rate of scattering between a first increment
of the received signal and a second increment of the
received signal
1665

Determine uterine tone
1670

Facilitate provision of an indication of uterine tone to an
operator
1675

Receive a signal that corresponds to an electrical current passed through the abdomen of a pregnant mammal
1705

Analyze the received signal
1710

Determine uterine tone
1715

Facilitate provision of an indication of uterine tone to an operator
1720

1800

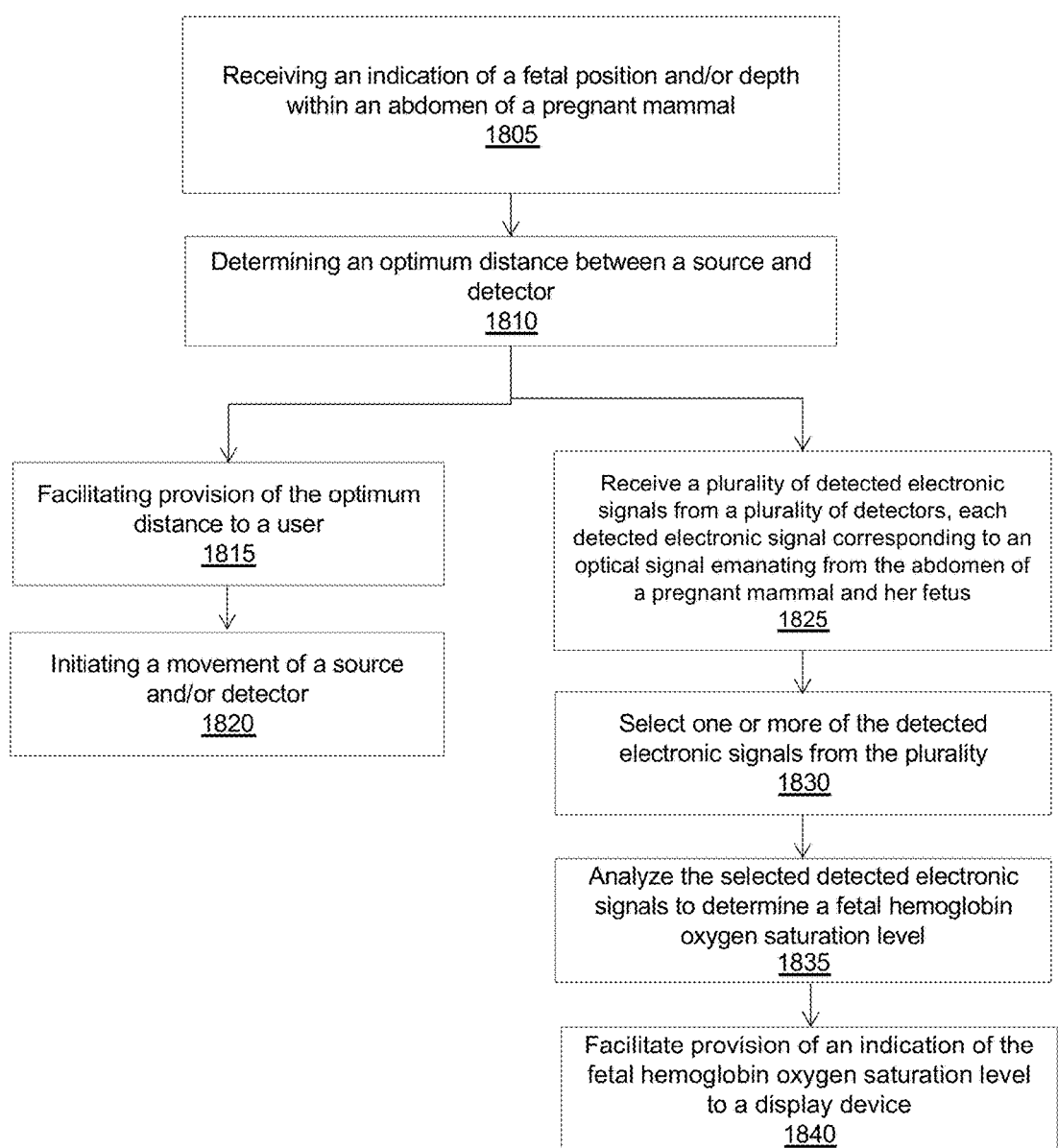

Receiving an indication of a fetal position and/or depth within an abdomen of a pregnant mammal
1805

Determining an optimum distance between a source and detector
1810

Facilitating provision of the optimum distance to a user
1815

Initiating a movement of a source and/or detector
1820

Receive a plurality of detected electronic signals from a plurality of detectors, each detected electronic signal corresponding to an optical signal emanating from the abdomen of a pregnant mammal and her fetus
1825

Select one or more of the detected electronic signals from the plurality
1830

Analyze the selected detected electronic signals to determine a fetal hemoglobin oxygen saturation level
1835

Facilitate provision of an indication of the fetal hemoglobin oxygen saturation level to a display device
1840

Figure 18

1900
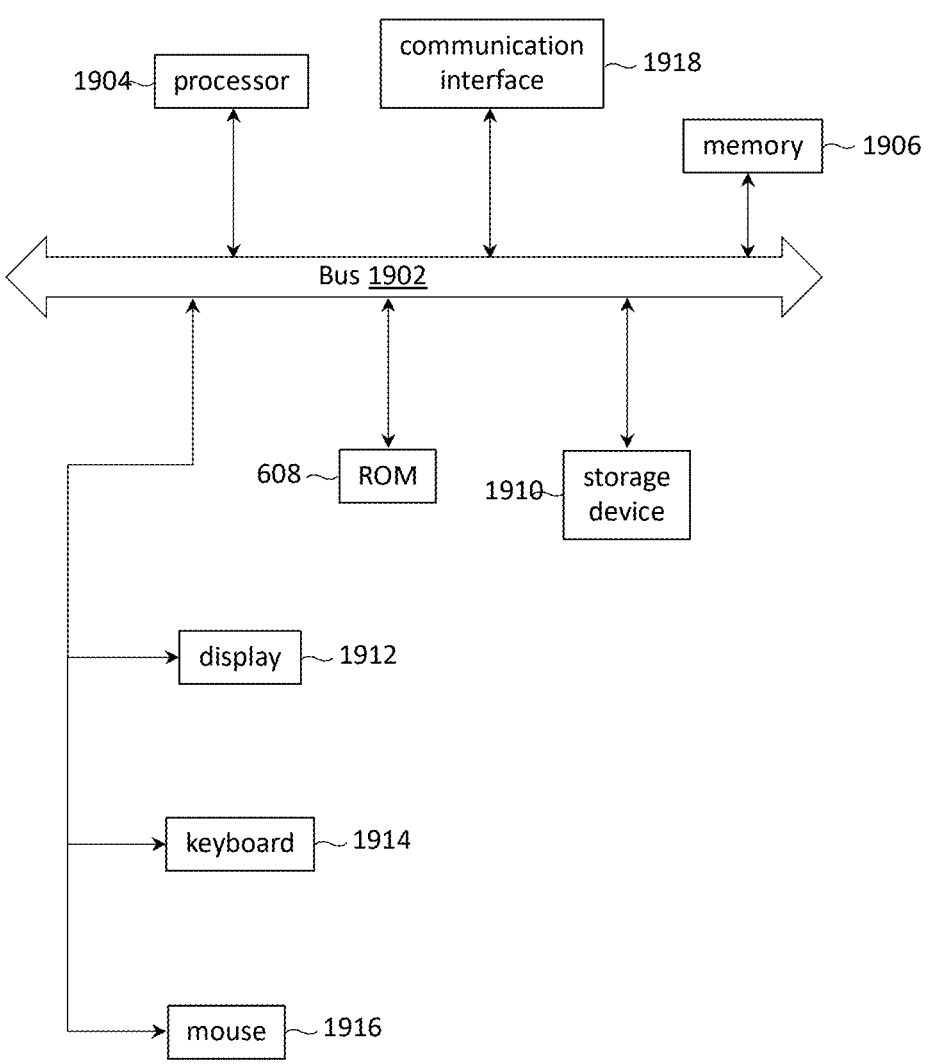
Fig. 19

TRANS-ABDOMINAL FETAL PULSE OXIMETRY AND/OR UTERINE TONE DETERMINATION DEVICES AND SYSTEMS WITH ADJUSTABLE COMPONENTS AND METHODS OF USE THEREOF

RELATED APPLICATION

This application is a Continuation of U.S. application Ser. No. 16/958,133 entitled "TRANS-ABDOMINAL FETAL PULSE OXIMETRY AND/OR UTERINE TONE DETERMINATION DEVICES AND SYSTEMS WITH ADJUSTABLE COMPONENTS AND METHODS OF USE THEREOF" filed Jun. 25, 2020, which is a U.S. National Phase Application of PCT/US2018/068049 entitled "TRANS-ABDOMINAL FETAL PULSE OXIMETRY AND/OR UTERINE TONE DETERMINATION DEVICES AND SYSTEMS WITH ADJUSTABLE COMPONENTS AND METHODS OF USE THEREOF" filed Dec. 28, 2018, which is a non-provisional of, and claims priority to, U.S. Provisional Patent Application No. 62/611,830 entitled "TRANS-ABDOMINAL FETAL PULSE OXIMETRY AND/OR UTERINE TONE DETERMINATION DEVICES AND SYSTEMS WITH ARTICULATING LIGHT SOURCE AND/OR LIGHT DETECTOR AND METHODS OF USE THEREOF" filed Dec. 29, 2017, which is incorporated by reference, in its entirety, herein.

FIELD OF INVENTION

The present invention is in the field of medical devices and, more particularly, in the field of trans-abdominal fetal oximetry, trans-abdominal fetal pulse oximetry, and optical uterine tone determination.

BACKGROUND

Oximetry is a method for determining the oxygen saturation of hemoglobin in a mammal's blood. Typically, 90% (or higher) of an adult human's hemoglobin is saturated with (i.e., bonded to) oxygen while only 30-60% of a fetus's blood is saturated with oxygen. Pulse oximetry is a type of oximetry that uses changes in blood volume through a heartbeat cycle to internally calibrate hemoglobin oxygen saturation measurements of the arterial blood.

Current methods of monitoring fetal health, such as monitoring fetal heart rate, are inefficient at determining levels of fetal distress and, at times, provide false positive results indicating fetal distress that may result in the unnecessary performance of a Cesarean section.

SUMMARY

Systems, devices, and methods for transabdominal fetal oximetry and/or fetal pulse oximetry and/or uterine tone determination are herein described. Some of the systems and devices disclosed herein have one or more articulating, adjustable, and/or selectable components. A system and/or device for transabdominal fetal oximetry and/or fetal pulse oximetry and/or uterine tone determination may include one or more articulating, adjustable, and/or selectable components such as a light source and/or a photodetector. In some embodiments, the positioning of a light source and/or detector may be adjustable. The articulation and/or adjustment of position of the light source and/or photodetector may be in any plane (X, Y, and/or Z) and, in some instances, may be responsive to a fetal position within a maternal abdomen.

Light detected by the detectors may be used to determine a fetal hemoglobin oxygen saturation level and/or a muscular state (e.g., contracted or relaxed) of the pregnant mammal's uterus.

In one exemplary system or device, a light source may be configured to project light into the abdomen of a pregnant mammal toward a fetus contained therein. The light source may be coupled to a first end of a first arm that includes a first end and a second end. The first end of the first arm may be coupled to the light source and the second end of the first arm may be coupled to a housing. In some embodiments, the light source may include a plurality of light producing elements. At times, the light producing elements may produce light of two or more different wavelengths or ranges of wavelengths. In some embodiments, the system may include a plurality of light sources that may be configured to articulate or move separately and/or as a unit. The plurality of light sources may be coupled to the housing via separate arms and/or may be joined together so that they are coupled to the housing via the same arm.

The system may also include a detector configured to detect light emanating from the pregnant mammal's abdomen responsively to light projected thereon by the light source. The detector may be a photodetector configured to convert the detected light into a detected signal. The detector may be coupled to a first end of a second arm. The second arm may include a first end and a second end, the first end of the second arm may be coupled to the detector and the second end of the second arm may be coupled to the housing. The housing may be configured to couple with the second end of the first arm and the second end of the second arm.

The first arm and/or the second arm may be configured to articulate relative to the housing. In some embodiments, housing, first arm, and/or second arm may be configured so that the articulation may place at the least one light source and detector proximate to of the pregnant mammal's abdomen. Additionally, or alternatively, housing, first arm, and/or second arm may be configured so that the articulation may adapt to a surface curvature of the pregnant mammal's abdomen. Additionally, or alternatively, housing, first arm, and/or second arm may be configured so that the articulation is responsive to a position of the fetus within the pregnant mammal's abdomen.

The articulation may be, for example, rotational around the housing. Additionally, or alternatively, the articulation of the first arm and/or the second arm may be pivotal rotation around the respective second end of the first arm and/or the second end of the second arm. Additionally, or alternatively, the articulation may be an extension or contraction of the first and/or second arm(s). Additionally, or alternatively, the articulation may be pivotal and/or rotational around an attachment mechanism coupling the light source to the first arm and/or an attachment mechanism coupling the detector to the second arm.

In some instances, a distance between the housing and the first and/or second arms may be adjustable. Additionally, or alternatively, a distance between the housing and the first and/or second arms may be adjustable via extension and contraction of the at least one first and second arm.

In some embodiments, the system may further include a fetal ultrasound device configured to determine and/or provide an indication of, for example, a position of the fetus and/or a distance between an epidermis of the pregnant mammal's abdomen and the fetus contained therein. In some cases, the articulation may be responsive to a distance between a surface of the pregnant mammal's abdomen and the fetus contained therein. In some instances, a distance between the source and the detector may be responsive to a distance between a surface of the pregnant mammal's abdomen and the fetus contained therein and/or a position of the fetus within the pregnant mammal's abdomen.

In some embodiments, the system may further include a transceiver configured to receive the detected signal from the detector and communicate the detected signal to a processor. The processor may be housed within the housing and/or external to the housing.

Additionally, or alternatively, the system may further include a processor configured to receive the detected signal from the detector and isolate a portion of the reflected electronic signal that corresponds to light incident upon the fetus, analyze the isolated portion of the detected signal to determine a fetal hemoglobin oxygen saturation level of the fetus, and provide an indication of the fetal hemoglobin oxygen saturation level of the fetus to a display device.

In some embodiments, the housing may further include a motor configured to facilitate articulation of at least one of the first arm and the second arm, a temperature probe configured to measure a temperature of at least one of the detector, the light source, the housing, and/or the pregnant mammal, a heat sink configured to transfer heat away from the detector, the light source, the housing, and/or the pregnant mammal, a controller configured to control the operations of one or more components of the system, and a display device configured to display information in, for example, a text, image, and/or graph format.

In some embodiments, the system may further include an additional light source configured to project light into the abdomen of a pregnant mammal toward the fetus contained. The additional light source may be coupled to, for example, the light source, detector, and/or a first end of a third arm. The third arm may include a first end and a second end, the first end of the third arm may be coupled to the additional light source and the second end of the third arm may be coupled to the housing.

When the system includes a processor, the processor may be configured to receive an indication of a distance between an epidermis of pregnant mammal's abdomen and a fetus contained therein, determine an optimum distance between a light source and a detector for the transmission of light to the fetus and detecting light emanating from the pregnant mammal's abdomen that has been incident upon the fetus responsively to the distance between an epidermis of pregnant mammal's abdomen and a fetus contained therein, and facilitate an indication of the optimum distance between the light source and a detector responsively to the determination. At times, a motor may be communicatively coupled to the processor. The motor may be configured to move the first and/or the second arms responsively to an instruction from the processor. In some embodiments, this instruction may be responsive to an optimum distance between the light source and detector.

BRIEF DESCRIPTION OF THE FIGURES

The present invention is illustrated by way of example, and not limitation, in the figures of the accompanying drawings in which:

FIG. 15 provides a flowchart illustrating a process for determining a fetal hemoglobin oxygen saturation level, consistent with some embodiments of the present invention;

FIG. 16B provides a flowchart illustrating a process for determining a state of uterine muscle tone, consistent with some embodiments of the present invention;

7

Figure 1A:
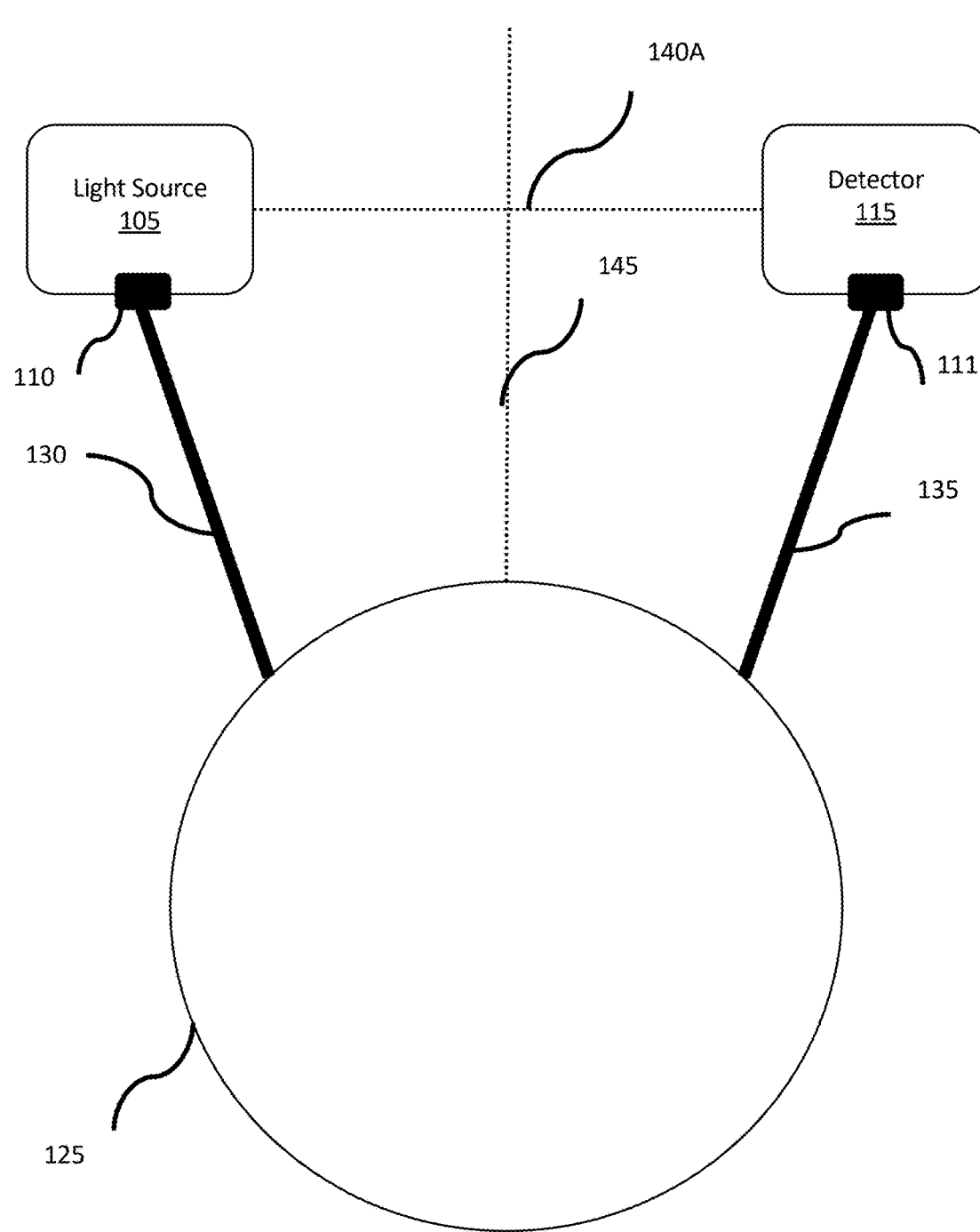
FIG. 1A provides a block diagram of an exemplary system for obtaining trans-abdominal fetal oximetry and/or trans-abdominal fetal pulse oximetry information with articulating components positioned in a first arrangement, in accordance with some embodiments of the present invention.

FIG. 18 provides a flowchart illustrating a process for determining fetal hemoglobin oxygen saturation level, consistent with some embodiments of the present invention; and FIG. 19 provides a diagram of an exemplary computing/processing device that may be used to execute one or more processes described herein, consistent with some embodiments of the present invention.

Throughout the drawings, the same reference numerals and characters, unless otherwise stated, are used to denote like features, elements, components, or portions of the illustrated embodiments. Moreover, while the subject invention will now be described in detail with reference to the drawings, the description is done in connection with the illustrative embodiments. It is intended that changes and modifications can be made to the described embodiments without departing from the true scope and spirit of the subject invention as defined by the appended claims.

DESCRIPTION

Described herein are systems, devices, and methods for conducting fetal oximetry and/or fetal pulse oximetry transabdominally. Additionally, or alternatively, the systems, devices, and methods described herein may be used to determine uterine tone of a pregnant mammal so as to, for example, monitor uterine contractions for the pregnant mammal during a labor and delivery process.

A key output of fetal oximetry and/or fetal pulse oximetry is the oxygen saturation of the fetal hemoglobin (also referred to herein as "fetal hemoglobin oxygen saturation level" and "oxygen saturation level"), which may also be understood as the percentage of hemoglobin present in the fetal blood that is bound to oxygen. The oxygen saturation level of fetal blood may be used by trained medical professionals to assess the health of a fetus as well as a level of hypoxic stress it may be experiencing during, for example, a labor and delivery process. Typically values of oxygen saturation for fetal blood fall within the range of 30-60% with anything lower than 30% indicating that the fetus may be at risk for hypoxic injury.

For the purposes of the following discussion, the terms "pregnant mammal" or "maternal," or "mother" are used to refer to female human being or animal (e.g., horse or cow) pregnant with a fetus. In most embodiments, the pregnant individual will be a human being, but this need not be the case as the invention may be used for nearly any pregnant mammal. Whether, or not, the pregnant mammal is the biological mother of the fetus (i.e., source of the egg from which the fetus grows) is not relevant to this invention. What is relevant is that the woman is pregnant with the fetus.

Typically, fetal wellbeing is assessed during labor and delivery by looking at the absolute fetal heart rate as measured in beats per minute and observing how fetal heart rate changes, or reacts to, changes in uterine tone (i.e., uterine contractions). It is generally accepted that a fetal heart rate within the range of 120-160 beats per minute is normal and does not indicate fetal compromise. However, sudden changes in fetal heart rate as well as fetal heart rates that are too high (e.g., 180 beats per minute) or too low (e.g., 100 or 80 beats per minute) are cause for concern, especially if these changes occur for a prolonged duration.

For example, as the uterus contracts to expel the baby out of the birth canal, the contracting uterus constricts the blood vessels and hence blood flow to and from the placenta, which supplies oxygen to the fetus. It is expected that restricted oxygen delivery to the fetus may result in a slowing of the fetal heart rate. However, a decrease in fetal heart rate from 150 to 120 after every uterine contraction may be an indication of fetal hypoxic compromise and may prompt intervention (e.g., a C-section, drug administration, etc.) by a physician or other clinician during the birthing process.

However, in some instances, this intervention may not be necessary because not all such decreases in fetal heart rate are caused by fetal hypoxia. In fact, the fetus is frequently just fine when its heart rate changes, but the physician has no further information to assist in determining whether the change in fetal heart rate is normal or pathological. Thus, an indication of the oxygen saturation level of the fetal hemoglobin would be a useful additional indication of fetal well-being when, for example, determining whether to intervene in the labor and delivery process with surgery or other treatment administration. For example, an indication that the fetal hemoglobin oxygen saturation level is constant and in the normal range provides an indication to the physician that the fetus is in good health even when the heart rate of the fetus decreases or changes. Conversely, a decrease in the fetal hemoglobin oxygen saturation level following uterine contractions coupled with a decreasing heart rate would be a cause for concern and may indicate to the physician that an intervention, like a C-section, is necessary.

Currently, many C-sections are performed solely because of variations in, or decreases of fetal heart rate, which are seen by physicians as a sign of fetal hypoxic compromise. 2 million C-sections are performed annually in the United States and, in some regions of the United States, C-sections are performed in nearly half (50%) of all births. In many instances, these C-sections may not be necessary because the fetus is actually not at risk of hypoxic injury. However, without further information (as may be provided via fetal pulse oximetry), physicians over-prescribe C-sections and other interventions out of an abundance of caution.

The present invention provides a more complete picture of fetal health during the labor and delivery process (and at other times during a pregnancy) and may thereby reduce the number of unnecessarily performed C-sections when the decision to perform a C-section is based on changes in fetal heart rate alone. It is expected that reducing the number of unnecessarily performed C-sections will reduce the overall cost of health care for pregnant women and newborns and reduce the number of complications that result from C-sections, which can be very significant. For example, 1 in 1000 C-sections will result in a major complication such as a blood clot, requirement of a blood transfusion, or surgical wound infection and 1 in 10,000 C-sections will result in death of the mother.

Fetal hemoglobin has a structure that is slightly different from the structure hemoglobin of adult hemoglobin. More specifically, adult hemoglobin has 2 alpha and 2 beta polypeptide chains and fetal hemoglobin has 2 alpha and 2 gamma polypeptide chains. Additionally, fetal hemoglobin has a stronger affinity for oxygen than adult hemoglobin. Because of these factors, fetal hemoglobin absorbs light differently than maternal hemoglobin.

Additionally, fetal hemoglobin has a conformation when bound to oxygen that is different from the conformation of the fetal hemoglobin when unbound to oxygen. These different conformations of the hemoglobin absorb light at different amounts and hence reflect light at different amounts. Using these differences, hemoglobin oxygen saturation of the fetal arterial blood can be measured.

Disclosed herein are systems, devices, and methods for performing non-invasive in-utero (i.e., trans-abdominal) fetal oximetry using, for example, near infrared spectroscopy (NIRS) to determine the oxygen saturation level of arterial and/or venous fetal hemoglobin. The determined oxygen saturation level of arterial and/or venous fetal hemoglobin may then be used by, for example, a physician or other caregiver to ascertain information regarding fetal health and/or compromise. In some embodiments, the systems, devices, and methods may employ a non-invasive monitor that can be placed on a pregnant mammal's abdomen to monitor fetal oxygen saturation levels.

Because fetal hemoglobin is microscopic, it cannot be observed directly. However, reflections of near infrared light from the fetal hemoglobin may be observed. Furthermore, different intensities for different wavelengths of light that are reflected by the fetal hemoglobin may also be observed. Additionally, different intensities for light that is reflected by fetal oxyhemoglobin when compared to fetal de-oxyhemoglobin may also be observed. Processing of this observed reflected light might yield a determination of a fetal oxygen saturation level.

FIGS. 1A-1K provide illustrations of an exemplary system 100 and/or components thereof for obtaining trans-abdominal fetal oximetry and/or trans-abdominal fetal pulse oximetry information regarding a fetus located in the uterus/abdomen of a pregnant mammal. System 100 may have one or more articulating and/or adjustable components. More specifically, system 100 may be used to obtain one or more optical signals emanating (via, for example, reflection, back scattering, and/or transmission) from the abdomen of a pregnant mammal. These optical signals may be introduced into the pregnant mammal's abdomen via a one or more light sources and/or light producing devices housed within a light source and may be detected by one or more photodetectors.

As shown in FIG. 1A, system 100 includes a light source 105, a detector 115, a housing 125, a first arm 130, and a second arm 135. First arm 130 may have a first end coupled to light source 105 and a second end coupled to housing 135. The coupling of first and/or second ends of first arm 130 may be achieved by any appropriate means (e.g., screw, hinge, ball bearings, ball joint, etc.). Optionally, light source 105 may be coupled to the first end of first arm 130 via a first attachment mechanism 110. In some embodiments, first attachment mechanism 110 may facilitate rotation or articulation of light source 105 relative to first arm 130 and/or housing 125.

Second arm 135 may have a first end coupled to detector 115 and a second end coupled to housing 125. The coupling of first and/or second ends of second arm 135 may be achieved by any appropriate means (e.g., screw, hinge, ball joint, ball bearings, etc.). Optionally, detector 115 may be coupled to the first end of second arm 135 via a second attachment mechanism 111. In some embodiments, second attachment mechanism 111 may facilitate rotation or articulation of detector 115 relative to second arm 135 and/or housing 125.

In some instances, first and second attachment mechanisms 110 and 111 may be of similar construction and operate similarly and, in other instances, first attachment mechanism 110 may have a first configuration specific to, for example, first arm 130 and/or light source 105 and second attachment mechanism 111 may have a second configuration specific to, for example, second arm 135 and/or detector 115. In some embodiments, housing 125 may house one or more of, for example, an optional ultrasound device and/or fetal heart rate monitor 180, an optional motor 120, an optional transceiver 122, an optional fan 132, an optional controller 137, a power source 195, a processor 185, a display 190, and/or an optional temperature probe 142 as shown in, for example, FIG. 1K.

Light source 105 may include one or more light producing elements (which may be collectively referred to herein as light source 105) configured to emit light of one or more frequencies and/or wavelengths. Exemplary light sources 105 and/or light producing elements include LEDs, light bulbs, LASERs, and the like. The light emitted by light source 105 may be directed into the pregnant mammal's abdomen toward the fetus. Typically, light emitted by light source 105 will be focused, or emitted, as a narrow beam to, for example, reduce spreading of the light upon entry into the pregnant mammal's abdomen and/or spreading of light emanating from the pregnant mammal's abdomen and/or fetus.

In some embodiments, system 100 may include a plurality, or array, of light sources 105 (not shown) and each light source 105 of the plurality may be adapted to direct light into the pregnant mammal's abdomen. In some instances, the plurality of light sources 105 may be adapted to be able to articulate or move separately and/or as a unit. Further details regarding the articulation of light source 105 are provided below.

An exemplary light source 105 is one with a relatively small form factor and high efficiency so as to limit heat emitted by the light source 105. In one embodiment, light source 105 and/or a light producing element included within light source 105 may be configured to emit light at 850 nm an example of which is the LED in Dragon Dome Package that Emits Light of 850 nm manufactured by OSRAM Opto Semiconductors (model number SFH 4783), which has a length of 7.080 mm and a width of 6.080 mm. Another exemplary light source 105 is a LED configured to emit light of 730 nm, such as the GF CSHPM1.24-3S4S-1 manufactured by OSRAM Opto Semiconductors, which has a height of 1.58 mm and a length of 3.1 mm. Exemplary flux ratios for light source 105 include but are not limited to a luminous flux/radiant flux of 175-260 mW, a total radiant flux of 300-550 mW and a power rating of 0.6 W-3.5 W. Often times, light source 105 includes at least two light producing elements and each light producing element may be configured to emit light of a different wavelength (e.g., 850 nm and 730 nm) so that pulse oximetry calculations may be performed.

In some embodiments, light source 105 and/or light producing elements contained therein may be a fiber optic cable transmitting light produced by another source (e.g., a LASER or tunable light bulb or tunable LED) that may not resident within housing 125 and/or light source 105. In some instances, the light source 105 may be tunable or otherwise user configurable while, in other instances, one or more of the light sources may be configured to emit light within a pre-defined range of wavelengths. Additionally, or alternatively, one or more filters (not shown) and/or polarizers may filter/polarize the light emitted by light source 105 to be of one or more preferred wavelengths. These filters/polarizers may also be tunable or user configurable. The tuning, filtering, and/or polarizing of a light source 105 may be executed by, for example, controller 137 and/or a component (e.g., lenses, filters, a motor, robotics, etc.) resident in light source 105 (not shown) responsively to, for example, instructions received via transceiver 122 and/or direct input from a user provided by, for example, buttons or other user interfaces provided by light source 105 and/or housing 125.

Tuning the frequency/wavelength and/or intensity of light emitted by light source 105 may be helpful in achieving a return/reflected signal of sufficient strength or clarity in a variety of circumstances (e.g., fetus position, fetus size, the amount of melanin in the skin of the pregnant mammal and/or fetus, the size and/or shape of the pregnant mammal, etc.). For example, light of a relatively higher intensity may be desired when the pregnant mammal has a relatively high body mass index (BMI) or body fat positioned in such a way as to inhibit the strength of a signal reflected from the fetus (i.e., return signal). In another example, a fetus may be positioned against the internal organs of the pregnant mammal (i.e., away from the skin of the abdomen) and light of relatively higher intensity and/or different wavelengths may be desired so that the light reaches the fetus with a sufficiently strong signal so that a return signal may be detected by, for example, detector 115.

In some embodiments, light source 105 may emit NIR light of a plurality (e.g., 7, 6, 5, 4, 3, 2) of wavelengths. In one embodiment, five different wavelengths are used wherein a first wavelength is used to measure an oxygen saturation level of adult oxyhemoglobin, a second wavelength is used to measure an oxygen saturation level of adult de-oxyhemoglobin, a third wavelength is used to measure an oxygen saturation level of fetal oxyhemoglobin, and a fourth wavelength is used to measure an oxygen saturation level of fetal de-oxyhemoglobin. The fifth wavelength may be used to clean up/improve the signal by assisting in the detection of portions of the reflected signal that may be caused and/or distorted by substances other than the pregnant mammal's and/or the fetal hemoglobin. For example, melanin and bilirubin are known to absorb infrared light. Thus, in instances where the fetus and/or pregnant mammal has a darker pigment or when either or both are jaundiced, the associated melanin and/or bilirubin may distort the fetal oximetry information readings, which may result in incorrectly calculating the oxygen saturation of the fetal and/or pregnant mammal's hemoglobin. The fifth wavelength may act to test for these distortions so that they may be removed from the received signal and accurate oxygen saturation levels may be determined.

Detector 115 may be configured to receive, or otherwise detect, light/photons emanating from the pregnant mammal's abdomen (and the fetus contained therein) and convert the detected light/photons into an electronic signal, which may be referred to herein as a detected electronic signal. Exemplary detectors 115 include, but are not limited to, cameras, traditional photomultiplier tubes (PMTs), silicon PMTs, avalanche photodiodes, and silicon photodiodes. In some embodiments, the detectors will have a relatively low cost (e.g., $50 or below), a low voltage requirement (e.g., less than 100 volts), and non-glass (e.g., polymeric material) form factor. In other embodiments, (e.g., contactless pulse oximetry) an extremely sensitive camera may be deployed to receive light reflected by the pregnant mammal's abdomen.

In some embodiments, detector 115 may be a sensitive camera adapted to capture small changes in fetal skin tone caused by changes in cardiovascular pressure as the fetal heart beats. In these embodiments, detector 115 may be in contact with the pregnant mammal's abdomen, or not, as this embodiment may be used to perform so-called contactless pulse oximetry. In these embodiments, light source 105 may be adapted to provide light (e.g., in the visible spectrum, near-infrared, etc.) directed toward the pregnant mammal's abdomen so that the detector 115 is able to receive light emanating from the pregnant mammal's abdomen and fetus. When detector 115 is a camera, the signal produced the detector 115 may be referred to as a detected electronic signal and/or an image signal.

First and second arms 130 and 135 may be adapted to articulate and/or move in the X-, Y-, and/or Z-planes via, for example, circumferential movement around housing 125, extension and/or contraction of first and/or second arms 130 and/or 135 in the X-, Y-, and/or Z-plane(s) (i.e., moving light source 105 or detector 115 closer or further away from housing 125), and/or movement of first and/or second arms 130 and/or 135 up or down relative to housing 125. Articulation of first and/or second arms 130 and/or 135 may be performed in order to, for example, position first and/or second arms 130 and/or 135 so as to be coincident with the pregnant mammal's abdomen and/or optimize a signal strength of the reflected signal. Once articulated into a position/configuration first and/or second arms 130 and/or 135, may maintain that position/configuration until moved or repositioned by, for example, a user, a motor like motor 120, and/or attachment mechanism 110 and/or 111. In some instances, first and/or second arms 130 and/or 135 and/or attachment mechanisms 110 and/or 111 may include a locking mechanism that maintains a position/orientation of light source 105 and/or detector 115 and/or releases light source 105 and/or detector 115 from a particular position/orientation so that it may be moved.

In some embodiments, first and/or second attachment mechanisms 110 and/or 111 may be an articulating joint (e.g., a ball joint, a pin joint, a bolted joint, and/or a hinge) that facilitates a range of motion (e.g., 90°, 180° or 360°) for the light source 105 and/or detector 115, respectively. In some instances, first and/or second attachment mechanisms 110 and/or 111 may be motorized to facilitate the automatic movement and/or articulation of light source 105 and/or detector 115 responsively to, for example, receipt of instructions for directing the movement of a motor (not shown) within first and/or second attachment mechanisms 110 and/or 111. In some embodiments, the instructions may be received from, for example, controller 137, transceiver 122, and/or a system like system 300 discussed below with regard to FIG. 3 via, for example, a transceiver positioned within light source 105, first attachment mechanism 110, detector 115 and/or second attachment mechanism 111.

Additionally, or alternatively, articulation of one or more components of system 100 may be facilitated by, for example, an articulating joint (e.g., a ball joint, a pin joint, a bolted joint, and/or a hinge) positioned between and/or coupling the second end of first arm 130 and housing 125 and/or second end of second arm 135 and housing 125. In some instances, the joint may articulate 3600, or some portion thereof, about the X-, Y-, and/or Z-axis. Additionally, or alternatively, articulation of one or more components of system 100 may be facilitated by a flexible, or bendable, material as may be the case when first arm 130 and/or second arm 135 is made from a flexible material, such as a cable or articulating metal and/or plastic arm so that first and/or second arms 130 and/or 135 may be bent in a non-linear fashion.

In some circumstances, articulation of a component of system 100 may be independent from other components of system 100 as may be the case when light source 105 is adapted to articulate (via, for example, first attachment mechanism 110) around first arm 130, which may be static (i.e., not articulating) and/or detector 115 is adapted to articulate (via, for example, second attachment mechanism 111) around second arm 135, which may be static (i.e., not articulating) In other circumstances, articulation of one component of system 100 may cause articulation of another component of system 100. For example, if second arm 135 is moved (i.e., articulated) then detector 115 and/or second attachment mechanism 111 may be adapted to articulate with no further external application of force of so as to, for example, maintain contact with the pregnant mammal's abdomen.

The articulation of light source 105, detector 115, first and/or second arms 130 and 135 may be facilitated by, for example, articulating joints, springs, flexible material, expanding material, and the like. In some instances, articulation of light source 105, detector 115, first and/or second arms 130 and 135 may be facilitated by motor 120, which may act to move, for example, first and/or second arms 130 and 135 responsively to instructions received from, for example, controller 137 and/or transceiver 122.

Also, it should be noted that although first and second arms 130 and 135 are shown in FIGS. 1A and 1D-1J as straight lines, they may, in some cases, be configured to bend or curve (e.g., via a spring or flexible material) so as to, for example, increase the flexibility of placement of light source 105 and/or detector 115. In some embodiments, first and second arms 130 and/or 135 may be made from the same or a similar material and/or be of the same design. In other embodiments, one or more aspects (e.g., material, design, etc.) of first arm 130 may differ from those of second arm 135.

Figure 1B:
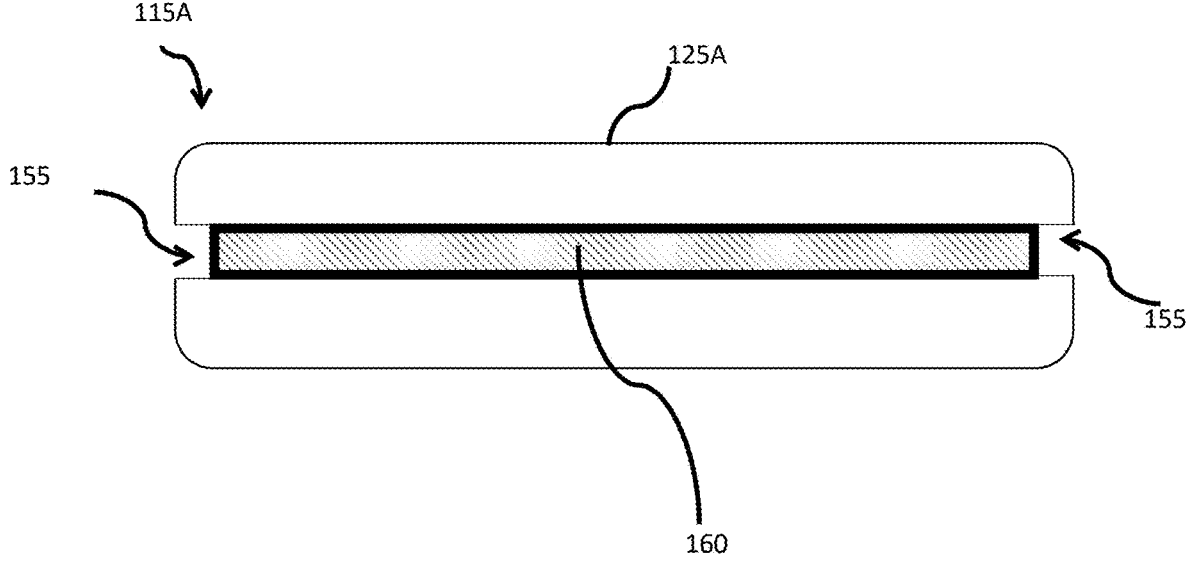
FIG. 1B provides a side plan view of a first exemplary housing for use with the system of FIG. 1A, in accordance with some embodiments of the present invention.

In some embodiments, first and/or second arms 130 and 135 may articulate by moving around housing 125 and/or changing their position and/or orientation relative to housing 125. In some cases, this articulation may be facilitated by a track 160 positioned circumferentially around a portion of housing 125 as may be seen in FIG. 1B, which shows a side plan view of housing 125. Track 160 may be any mechanism or combination of mechanisms (e.g., track, ball bearings, joints, etc.) that enables first and/or second arms 130 and 135 to move circumferentially around housing 125. In the embodiment of FIG. 1B, track 160 is recessed into the body of housing 125 within an optional open space 155 that circumferentially surrounds a portion of housing 125.

Figure 1C:
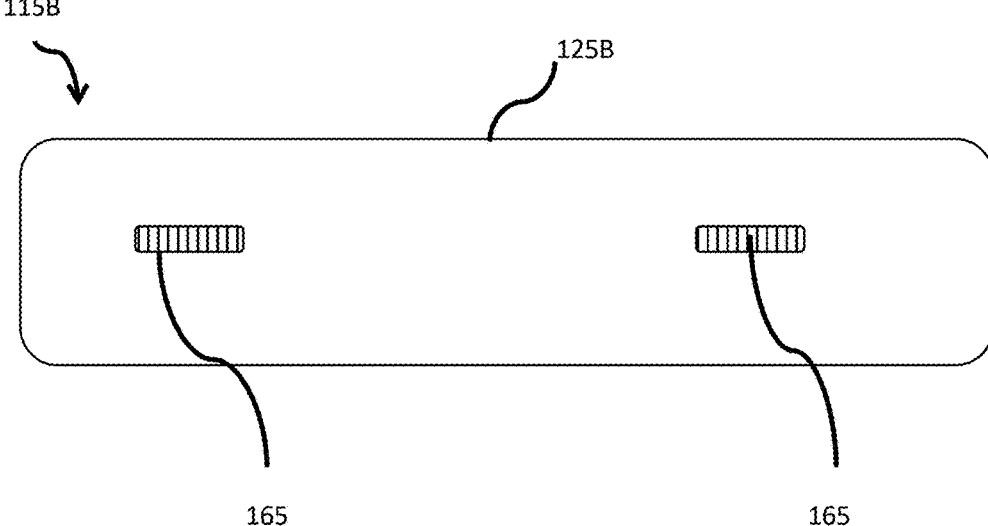
FIG. 1C provides a side plan view of a second exemplary housing for use with the system of FIG. 1A, in accordance with some embodiments of the present invention.

Additionally, or alternatively, first and second arms 130 and 135 may be attached to housing 125 via an attachment mechanism 165 as shown in FIG. 1C. Attachment mechanisms 165 may facilitate the permanent (i.e., not removable) or non-permanent (i.e., removable) attachment of the second ends of first and/or second arms 130 and/or 135 to housing 125. Exemplary attachment mechanisms 165 include a joint, a coupling, a hinge and/or a clamp. In some embodiments, second ends of first arm 130 and/or second arm 135 may include a cooperating portion (not shown) of attachment mechanism 165 (e.g., clip, hole, etc.) adapted to cooperate with attachment mechanism 165 and couple first arm 130 and/or second arm 135 thereto. In these embodiments, attachment of first arm 130 and/or second arm 135 to housing 125 may be facilitated by attaching the cooperating portion of the second end of first arm 130 and/or second arm 135 to one of attachment mechanisms 165.

In some embodiments, a preferred magnitude of the distance between light source 105 and detector 115 may be responsive to a depth of the fetus within the abdomen that may be determined by, for example, ultrasound device/fetal heart rate monitor 180 or another device. For example, if a fetus is determined to be 2 cm below the skin of the maternal abdomen, then a magnitude of a distance between light source 105 and detector 115 may be a multiplicative factor of 2 cm (e.g., 2×3, 2×4, 2×1.870 etc.). Additionally, or alternatively, a position of light source 105 relative to detector 115 may be responsive to a depth, position, and/or orientation (as may be determined by ultrasound device/fetal heart rate monitor 180 or another device) of the fetus within the pregnant mammal's abdomen.

FIGS. 1A-1D provide four exemplary arrangements of light source 105, detector 115, first arm 130, and second arm 135 that are adjusted based on, for example, fetal depth and position. To facilitate discussion of the relative position of light source 105 and detector 115, the illustrations of FIGS. 1A and 1D-1F provide a first reference line 140 that represents a distance between a center point of right side of light source 105 and a center point of the left side of detector 115, and a second reference line 145 that bisects first reference line 140 and is oriented along the Y-axis (i.e., straight up and down) midway through housing 125. First and second reference lines 140 and 145 are superimposed onto the illustrations of system 100 to assist with explanation of positions and orientations of various components of system 100 and are not tangible parts of system 100.

In FIG. 1A, a first exemplary arrangement of light source 105 and detector 115 relative to housing 125 with reference line 140A representing the distance therebetween. Light source 105 and detector 115 are arranged so that they are the same distance away from housing 125 and an angle (e.g., −20°) of first arm 130 relative to second reference line 145 is substantially the same in magnitude (although reverse in direction) as an angle (e.g., 20°) of second arm 135 relative to second reference line 145.

Figure 1D:
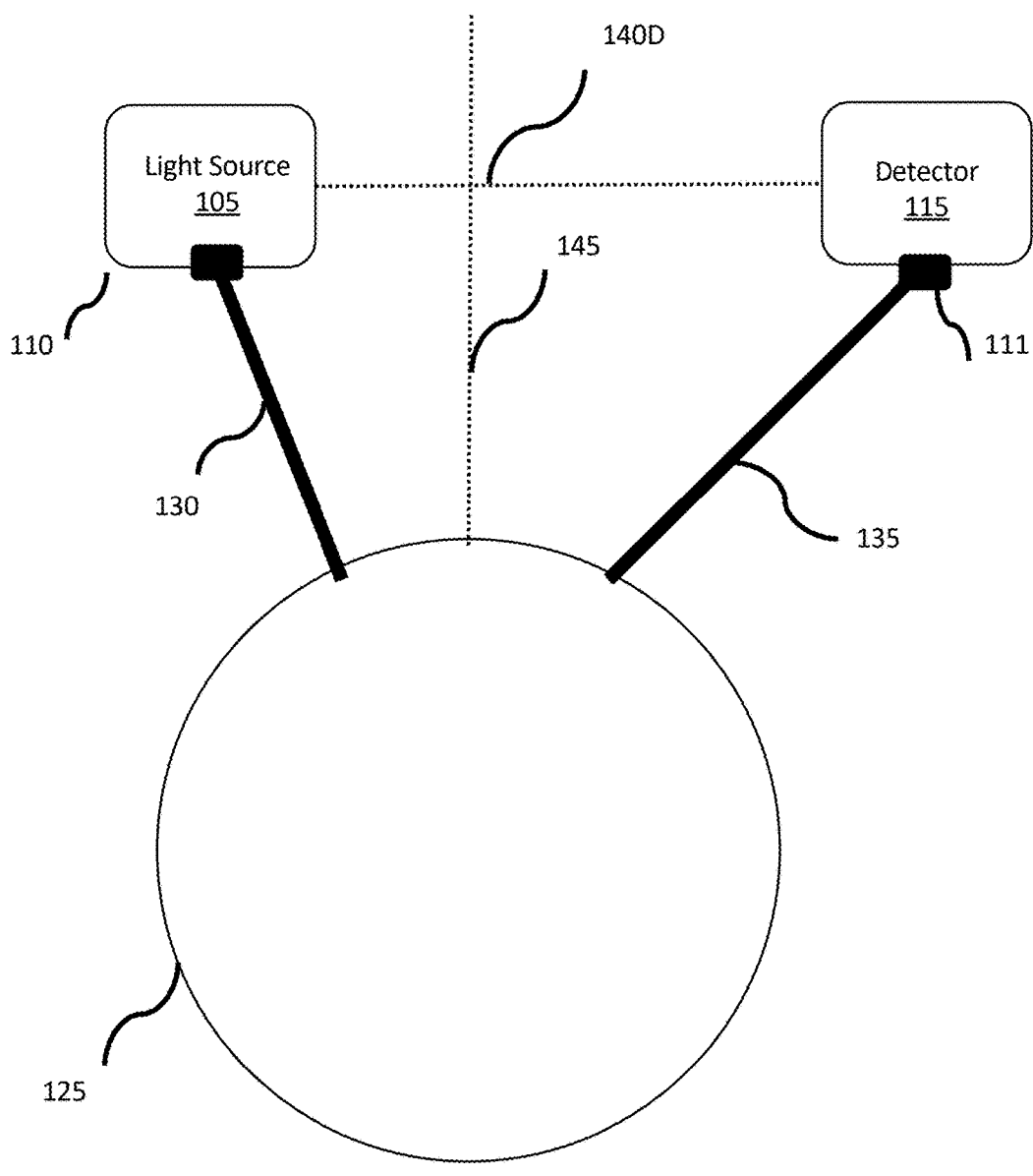
FIG. 1D provides a block diagram of the exemplary system of FIG. 1A with articulating components positioned in a second arrangement, in accordance with some embodiments of the present invention.

In another example, FIG. 1D provides a second exemplary arrangement of light source 105 and detector 115 relative to housing 125 and shows light source 105 and detector 115 aligned so that reference line 140D is perpendicular to reference line 145 by the angle of first arm 130 relative to second reference line 145 is not of the same magnitude as the angle of second arm 135 relative to second reference line 145. First arm 130 is also shorter than second arm 135. This may be achieved by, for example, compressing first arm 130 and/or extending second arm 135. The length of reference line 140D is shorter than the length of reference line 140A, indicating that a distance between source 105 and 115 is greater for FIG. 1D than for FIG. 1A. This arrangement may be advantageous when, for example, the fetus is not as deep within the abdomen than the depth of the fetus of FIG. 1A.

Figure 1E:
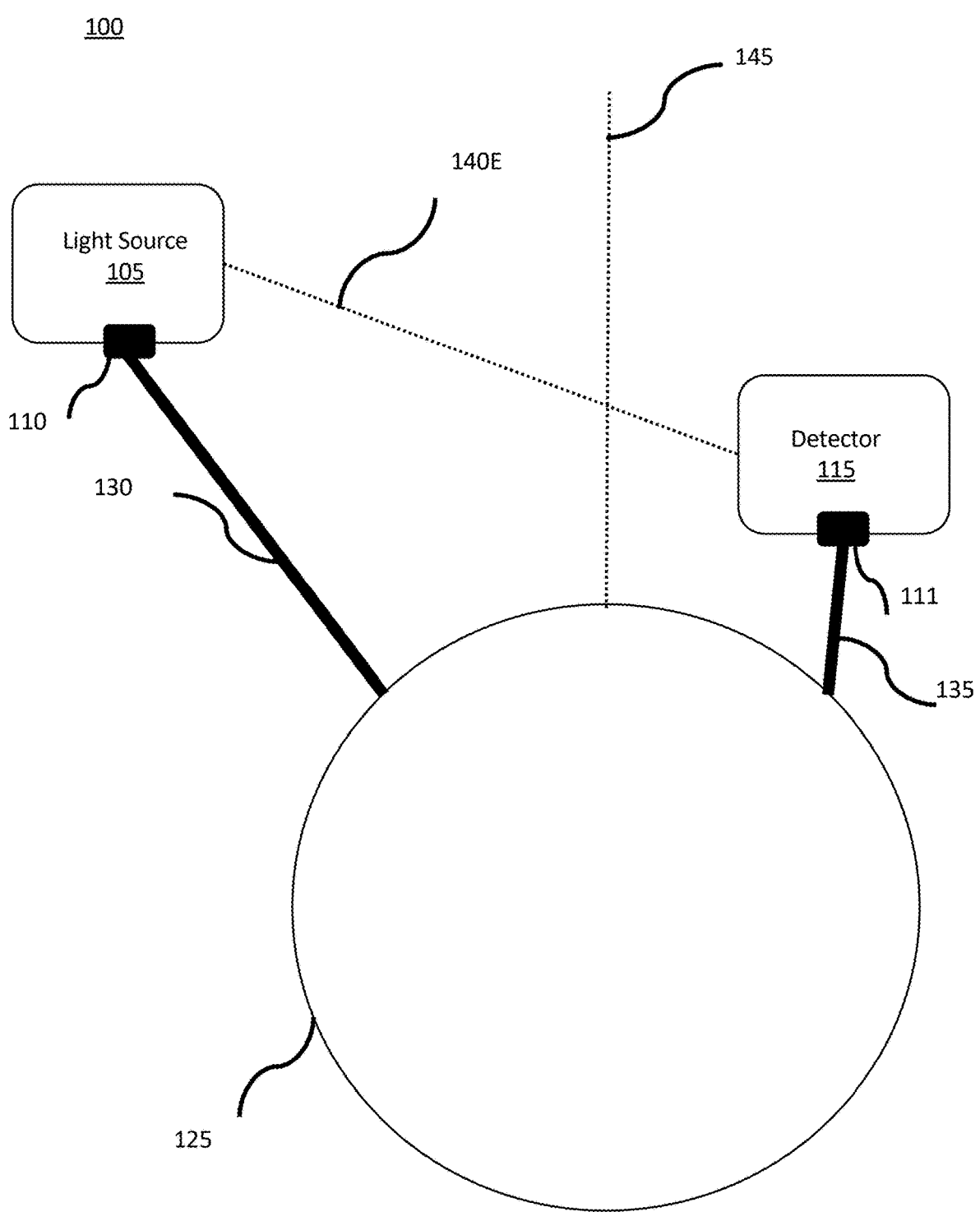
FIG. 1E provides a block diagram of the exemplary system of FIG. 1A with articulating components positioned in a third arrangement, in accordance with some embodiments of the present invention.

FIG. 1E provides a third exemplary arrangement of light source 105 and detector 115 relative to housing 125 wherein the length of first arm 130 is longer than second arm 135 so that detector 115 is closer to housing 125 than light source 105. In the arrangement of FIG. 1E, reference line 140E is not perpendicular to second reference line 145. Also, the angle between first arm 130 and second reference line 145 is greater in magnitude than the angle between second arm 135 and second reference line 145.

Figure 1F:
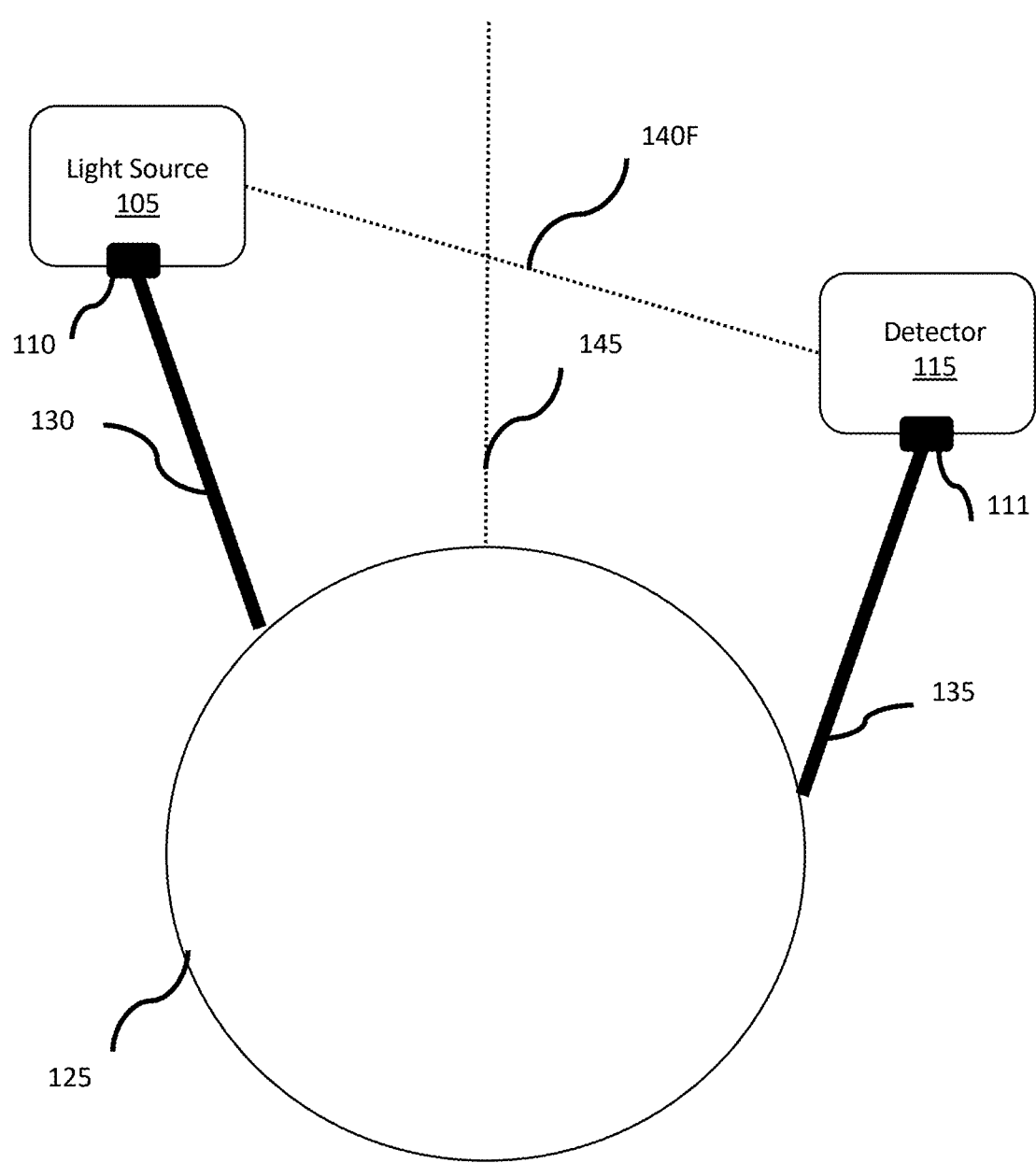
FIG. 1F provides a block diagram of the exemplary system of FIG. 1A with articulating components positioned in a fourth arrangement, in accordance with some embodiments of the present invention.

FIG. 1F provides a fourth exemplary arrangement of light source 105 and detector 115 relative to housing 125 wherein the end of second arm 135 that is coupled to housing 125 is positioned further away from second reference line 145 (i.e., lower on housing) than is shown in FIGS. 1A, 1D, and 1E. Positioning of detector 115 as shown in FIG. 1F may be achieved by moving second arm 135 along track 160 as explained above with regard to FIG. 1E and/or articulating second arm 135 using attachment mechanism 165. In the arrangement of FIG. 1D, reference line 140F is not perpendicular to second reference line 145 with detector 115 being positioned lower than light source 105. Additionally, a magnitude of the angle between first arm 130 and second reference line 145 is less than a magnitude of the angle between second arm 135 and second reference line 145 in the exemplary arrangement of FIG. 1F.

Figure 1G:
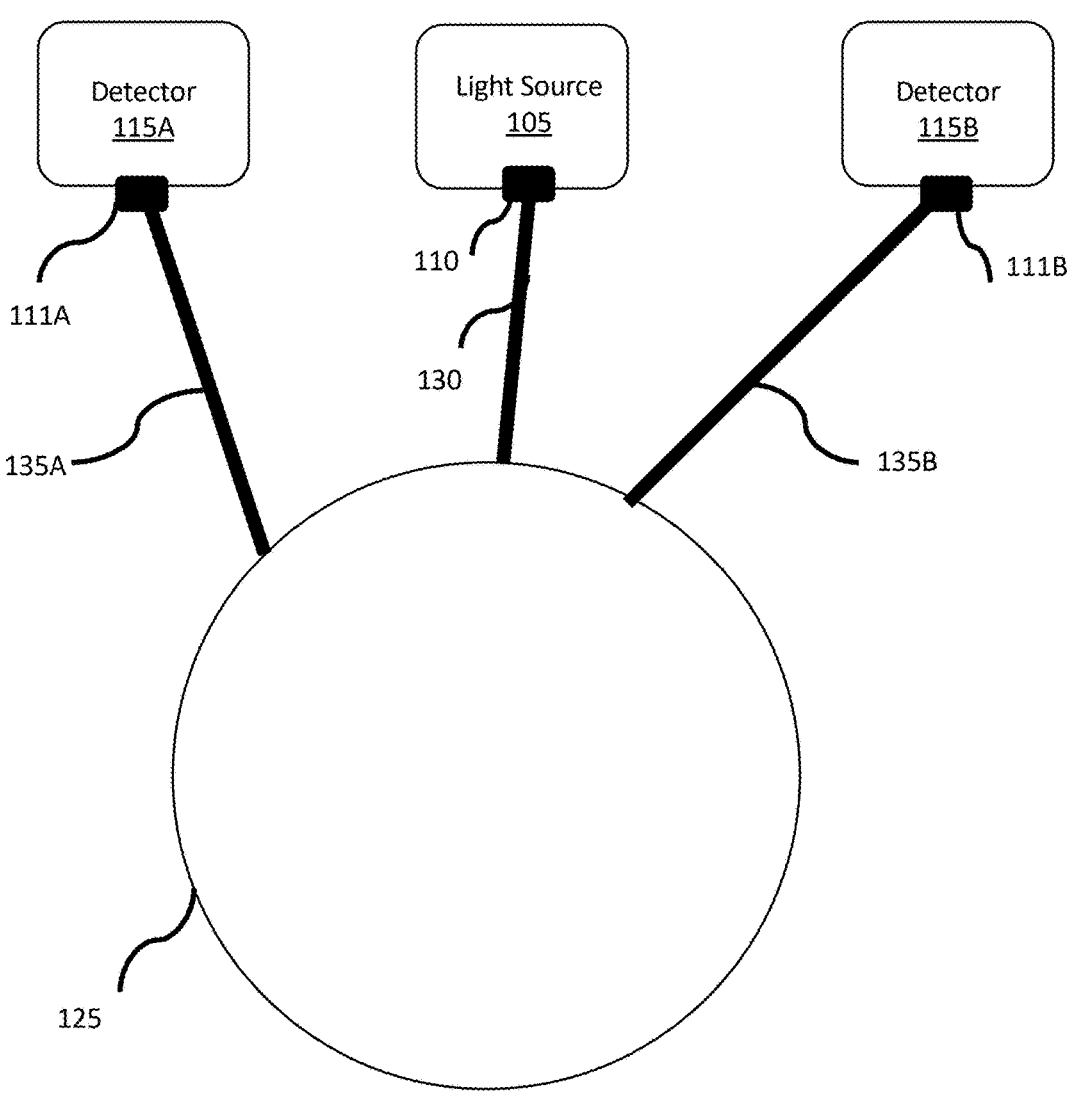
FIG. 1G provides a block diagram of another exemplary system for obtaining trans-abdominal fetal oximetry and/or trans-abdominal fetal pulse oximetry information with articulating components, in accordance with some embodiments of the present invention.

FIG. 1G provides an illustration of an exemplary system 101 for obtaining trans-abdominal fetal oximetry information regarding a fetus located in the uterus/abdomen of a pregnant mammal. System 101 is similar to system 100 except that system 101 includes a second detector. More particularly, the components of system 101 are housing 125, light source 105, first arm 130, a first detector 115A, a first instance of second arm 135A, a second detector 115B, a second instance of second arm 135B, a first instance of second attachment mechanism 111A, and a second instance of second attachment mechanism 111B. First and second detectors 115A and 115B are positioned on either side of light source 105 and may be moved, or otherwise articulated, to detect light emanating from the abdomen of a pregnant mammal that was projected into the maternal abdomen by light source 105.

Figure 1H:
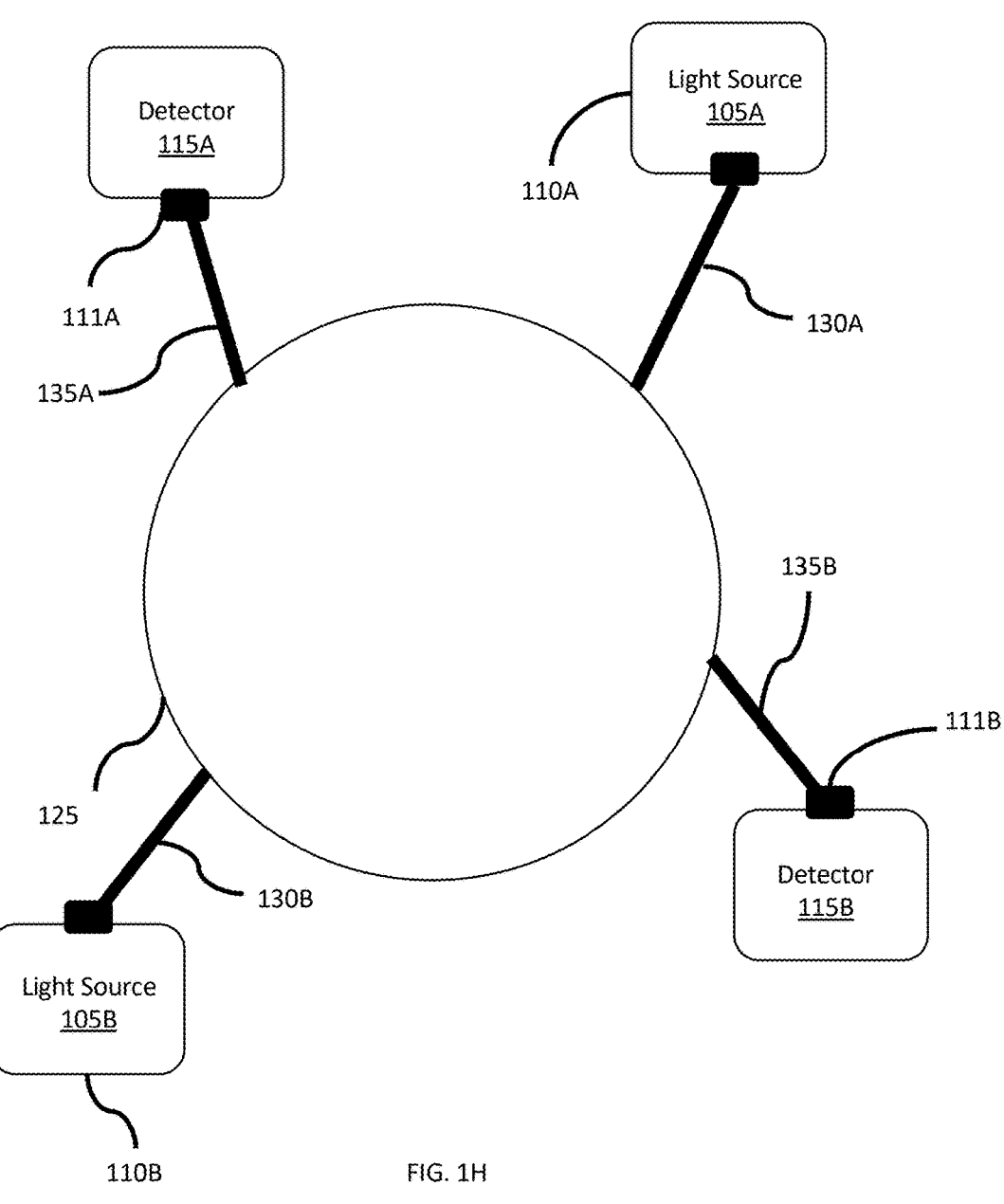
FIG. 1H provides a block diagram of another exemplary system for obtaining trans-abdominal fetal oximetry and/or trans-abdominal fetal pulse oximetry information with articulating components, in accordance with some embodiments of the present invention.

FIG. 1H provides an illustration of an exemplary system 102 for obtaining trans-abdominal fetal oximetry information regarding a fetus located in the uterus/abdomen of a pregnant mammal. System 102 is similar to system 101 except that system 102 includes a second light source. More particularly, the components of system 101 are housing 125, a first light source 105A, a first instance of first arm 130A, a second light source 105B, a second instance of first arm 130B, first detector 115A, first instance of second arm 135A, second detector 115B, second instance of second arm 135B, a first instance of second attachment mechanism 111A, and a second instance of second attachment mechanism 111B. As shown in FIG. 1H, first light source 105A and second light source 105B are positioned between first and second detectors 115A and 115B. Other arrangements are also contemplated such as having first and second light sources 105A and 105B next to one another (i.e., without a detector positioned between them). First and second light sources 105A and 105B may be articulated to illuminate areas of the maternal abdomen of interest (typically where the fetus is located) and first and second detectors 115A and 115B may be articulated to detect light resulting from the illumination provided by first and/or second light sources 105A and/or 105B.

Figure 1I:
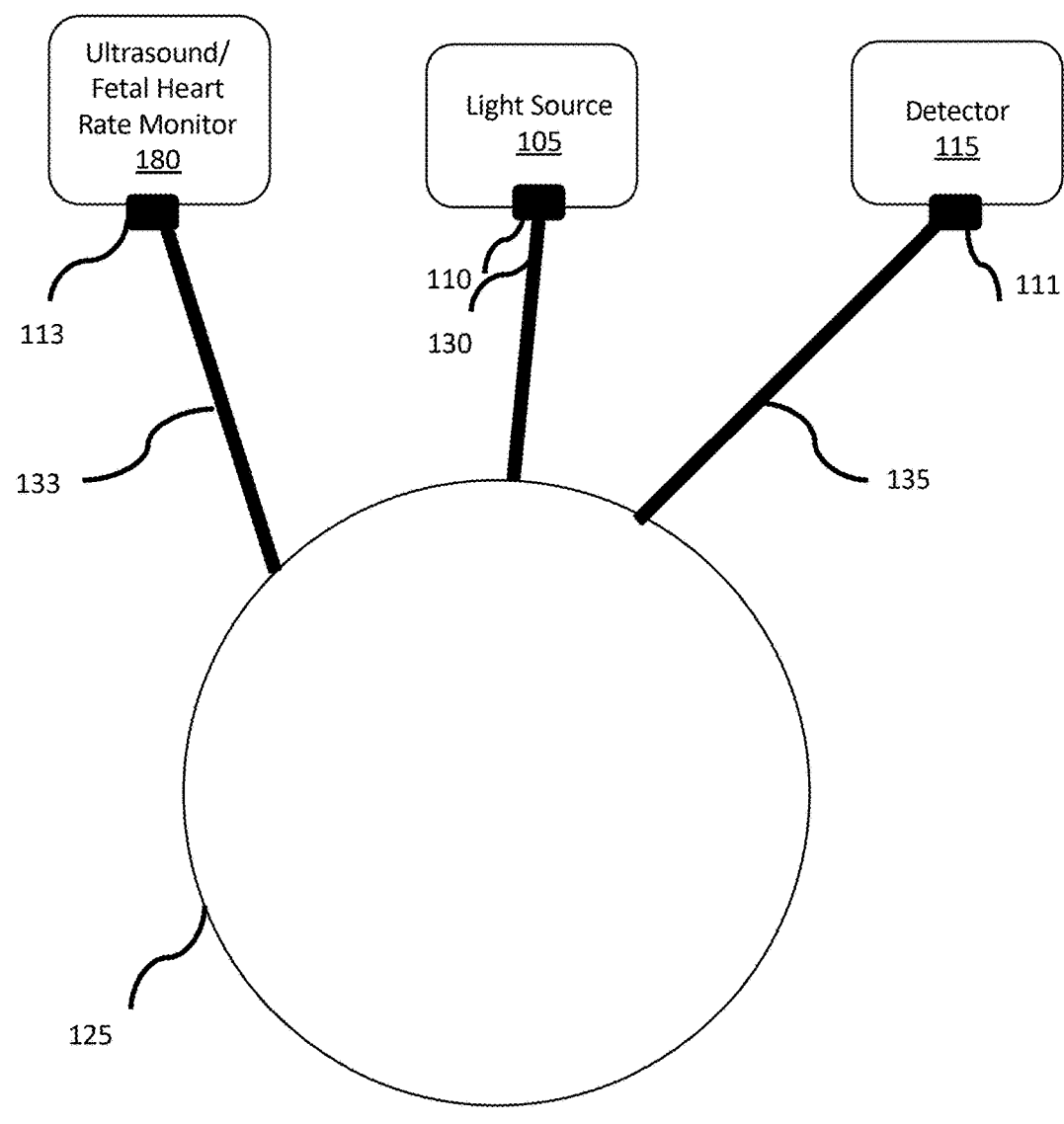
FIG. 1I provides a block diagram of another exemplary system for obtaining trans-abdominal fetal oximetry and/or trans-abdominal fetal pulse oximetry information with articulating components, in accordance with some embodiments of the present invention.

FIG. 1I provides an illustration of an exemplary system 103 for obtaining trans-abdominal fetal oximetry information regarding a fetus located in the uterus/abdomen of a pregnant mammal. System 103 is similar to system 100 with the exception that system 103 includes an ultrasound/fetal heartrate monitor 180 that is coupled to a third arm 133 via an attachment mechanism 113. The functioning of ultrasound/fetal heartrate monitor 180 is described below with regard to the discussion of FIG. 1K. Ultrasound/fetal heartrate monitor 180 may articulate relative to housing 125 and/or light source 105 and/or detector 115 in order to, for example, locate a fetus and/or a body part of a fetus (e.g., head or back).

Figure 1J:
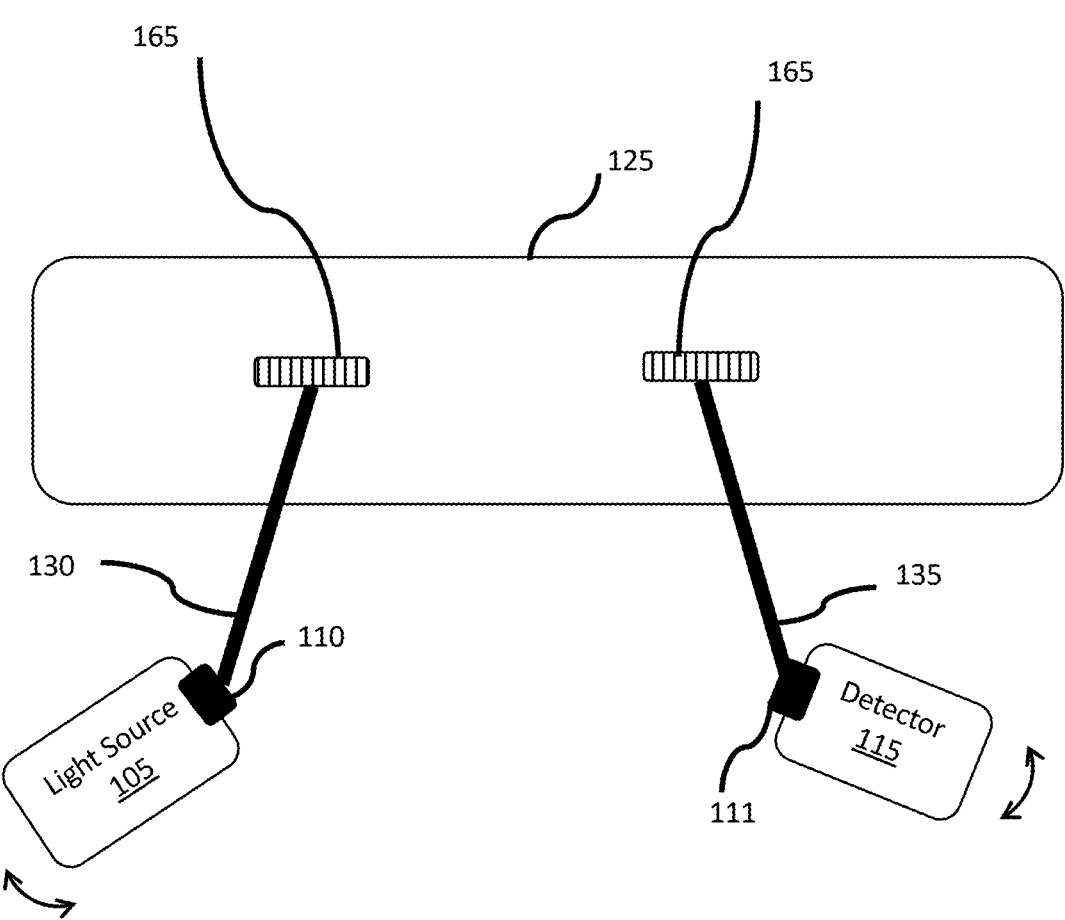
FIG. 1J provides a side plan view of the exemplary system of FIG. 1A, in accordance with some embodiments of the present invention FIG. 1K provides a block diagram of exemplary components housed within a housing for the system of FIG. 1A, in accordance with some embodiments of the present invention.

FIG. 1J provides a side view of an exemplary embodiment of system 100 with both light source 105 and detector 115 positioned below housing 125 as may be advantageous when, for example, housing 125 is positioned on an apex of the pregnant mammal's abdomen. In the embodiment of FIG. 1J, light source 105 and detector 115 are coupled to first arm 130 and second arm 135, respectively, via an exemplary first and second attachment mechanism 110 and 111, respectively, that has 360° freedom. In the example of FIG. 1J, light source 105 is oriented at an angle (i.e., not parallel) to first arm 130 and detector 115 is oriented at an angle (i.e., not parallel) to second arm 135. Articulation of light source 105 and/or detector 115 via their respective first and second attachment mechanism 110 and 111 may facilitate positioning of light source 105 and/or detector 115 coincident to the pregnant mammal's abdomen and/or the fetus included therein so that, for example, the reflected signal received by detector 115 may be optimized.

The different positions of light source 105 and detector 115 shown in the first, second, third and/or fourth exemplary arrangements of FIGS. 1A and 1D-1F may be facilitated by, for example, rotating first and/or second arms 130 and/or 135 around track 160, moving first and/or second arms 130 and/or 135 via attachment mechanism 165 and/or moving light source 105 and/or detector 115 via first and/or second attachment mechanisms 110 and/or 111 and/or via motor 120.

Figure 1K:
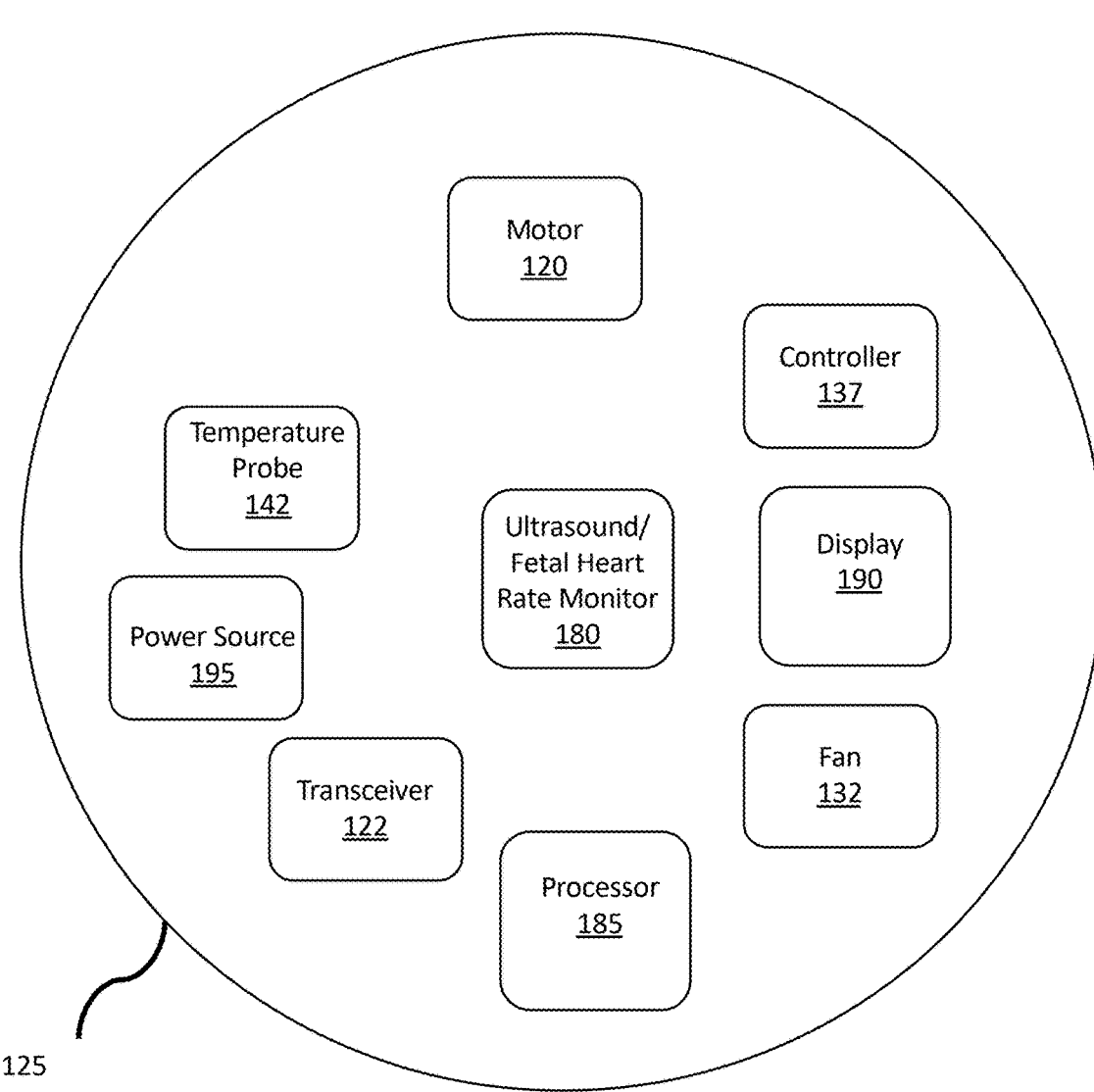

FIG. 1K illustrates a plurality of optional components that may be housed in housing 125. More specifically, FIG. 1K shows ultrasound device/fetal heart rate monitor 180, motor 120, transceiver 122, fan 132, controller 137, temperature probe 142, a processor 185, a display 190, and a power source 195. In some embodiments, housing 125 may also house a uterine contraction measurement device (not shown). Power source 195 may be, for example, an on-board power supply (e.g., a battery) and/or a coupling to an external electrical power source (e.g., electrical main). Power source 195 may supply power to one or more components of system 100.

The components of system 100 and/or components included within housing 125 may be communicatively coupled together via wired and/or wireless communication links. At times, communication between components of system 100 may be facilitated by transceiver 122, which may transmit information received from and/or communication instructions to, for example, ultrasound device/fetal heart rate monitor 180, detector 115, light source 105, first and/or second attachment mechanisms 110 and/or 111, motor 120, fan 132, and/or temperature probe 142. Processor 185 may be communicatively coupled to some, or all, components of system 100 and/or components housed in housing 125. Processor 185 may be configured to perform one or more methods disclosed herein.

In some embodiments, information received by transceiver 122 (from, for example, processor 185) may be communicated to an external device, such as a computer, as will be discussed below with regard to FIG. 3. In some instances, wireless communication of one or more components of system 100 may be enabled using short-range wireless communication protocols designed to communicate over relatively short distances (e.g., BLUETOOTH® near field communication (NFC), radio-frequency identification (RFID), and Wi-Fi) with, for example, a computer or personal electronic device as described below. In some embodiments, one or more components of system 100 may include one or more devices configured to communicate via one or more short-range communication protocols (e.g., near field communication (NFC), BLUETOOTH®, radio-frequency identification (RFID), and Wi-Fi).

Ultrasound device/fetal heart rate monitor 180 may be a device configured to determine a heart rate of a fetus positioned in the pregnant mammal's abdomen and/or image the maternal abdomen so that, for example, a fetal depth may be determined. In some cases, fetal heart rate monitor 180 may also be adapted to determine a depth, orientation, and/or position of a fetus, or a particular portion thereof (e.g., head or cheek), within the pregnant mammal's abdomen. Exemplary ultrasound devices/fetal heart rate monitors include, but are not limited to, ultrasound, Doppler, and/or ECG devices.

In some instances, detector 115 and/or fetal heart rate monitor 180 may include one or more ultrasonic detectors (not shown) that may be employed in embodiments where detector 115 and/or fetal heart rate monitor 180 is/are configured to perform optoacoustic/photoacoustic and/or thermoacoustic imaging by way of directing a light or radio frequency pulse from light source 105 into the pregnant mammal's abdomen. A portion of the incident light may be absorbed by the fetus and pregnant mammal and converted into heat, which leads to transient thermoelastic expansion, which causes an ultrasonic emission from the fetus and pregnant mammal. This ultrasonic emission may be detected by the ultrasonic detector and analyzed to determine a level of oxygen saturation for the fetal and/or pregnant mammal's blood.

Temperature probe 142 may be configured to monitor the temperature of system 100, the pregnant mammal, and/or the skin of the pregnant mammal near where system 100 is located. If temperature probe 142 indicates (as may be determined by, for example, controller) that system 100 and/or the pregnant mammal is too hot, then fan 132 may be activated to cool down the components of system 100, the components included in housing 125, and/or the pregnant mammal. At times, the decision to turn on a fan responsively to a temperature being above a threshold (e.g., 100 degrees F.), may be made by processor 185 responsively to receiving temperature data. In some embodiments, processor 185 may provide information to display so that an indication of the temperature from temperature probe 142 may be displayed to a user.

System 100, housing 125, light source 105 and/or detector 115 may be affixed to the pregnant mammal's abdomen in any acceptable fashion including, but not limited to, an adhesive, a strap, a harness, and a component of a garment. In some cases, housing 125 may be affixed to the pregnant mammal's abdomen so that light source 105 and detector 115 are free to articulate.

Figure 2A:
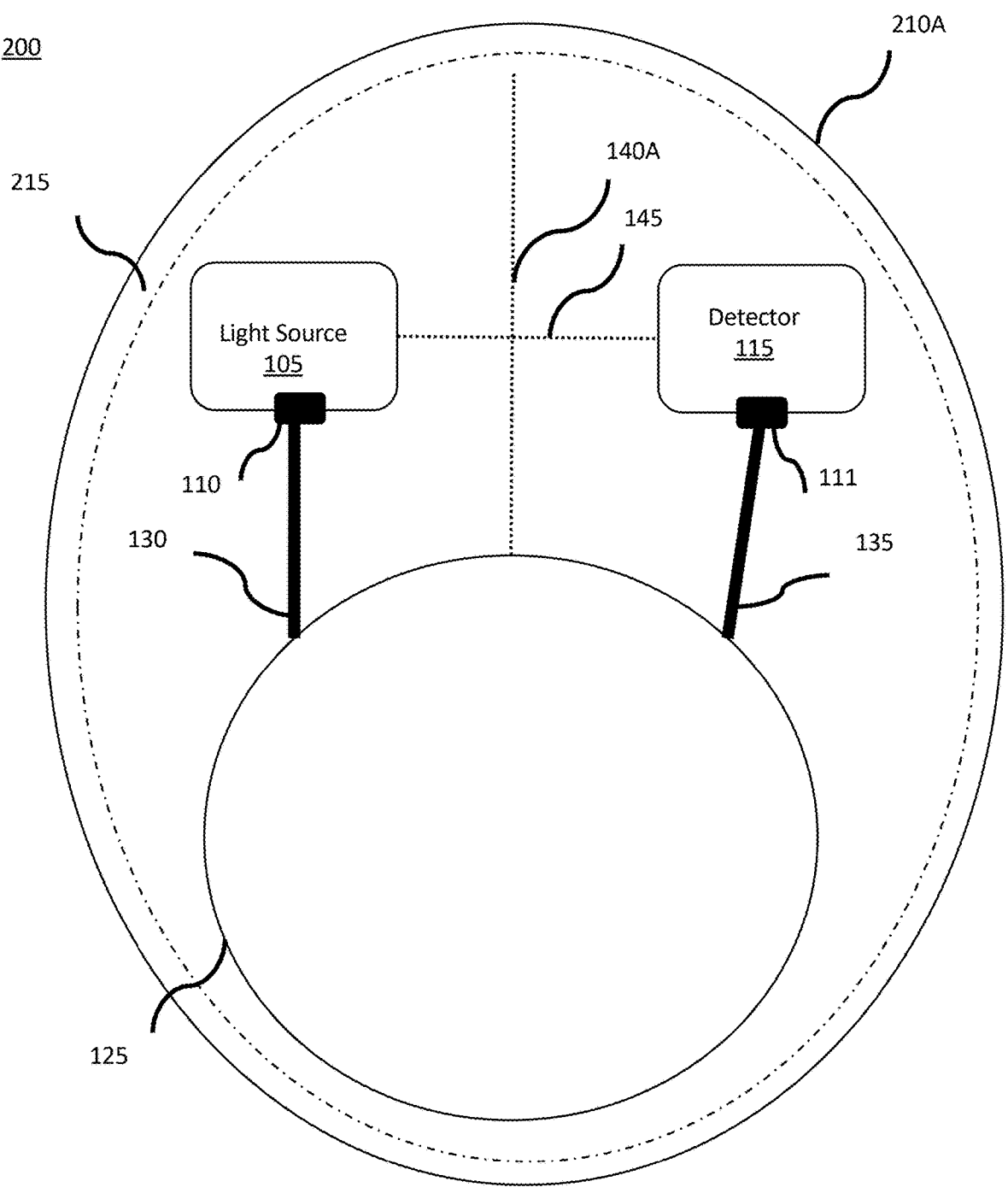
FIG. 2A provides a block diagram of an obtaining trans-abdominal fetal oximetry and/or trans-abdominal fetal pulse oximetry information that includes a covering member that covers all components of the system, in accordance with some embodiments of the present invention.
Figure 2B:
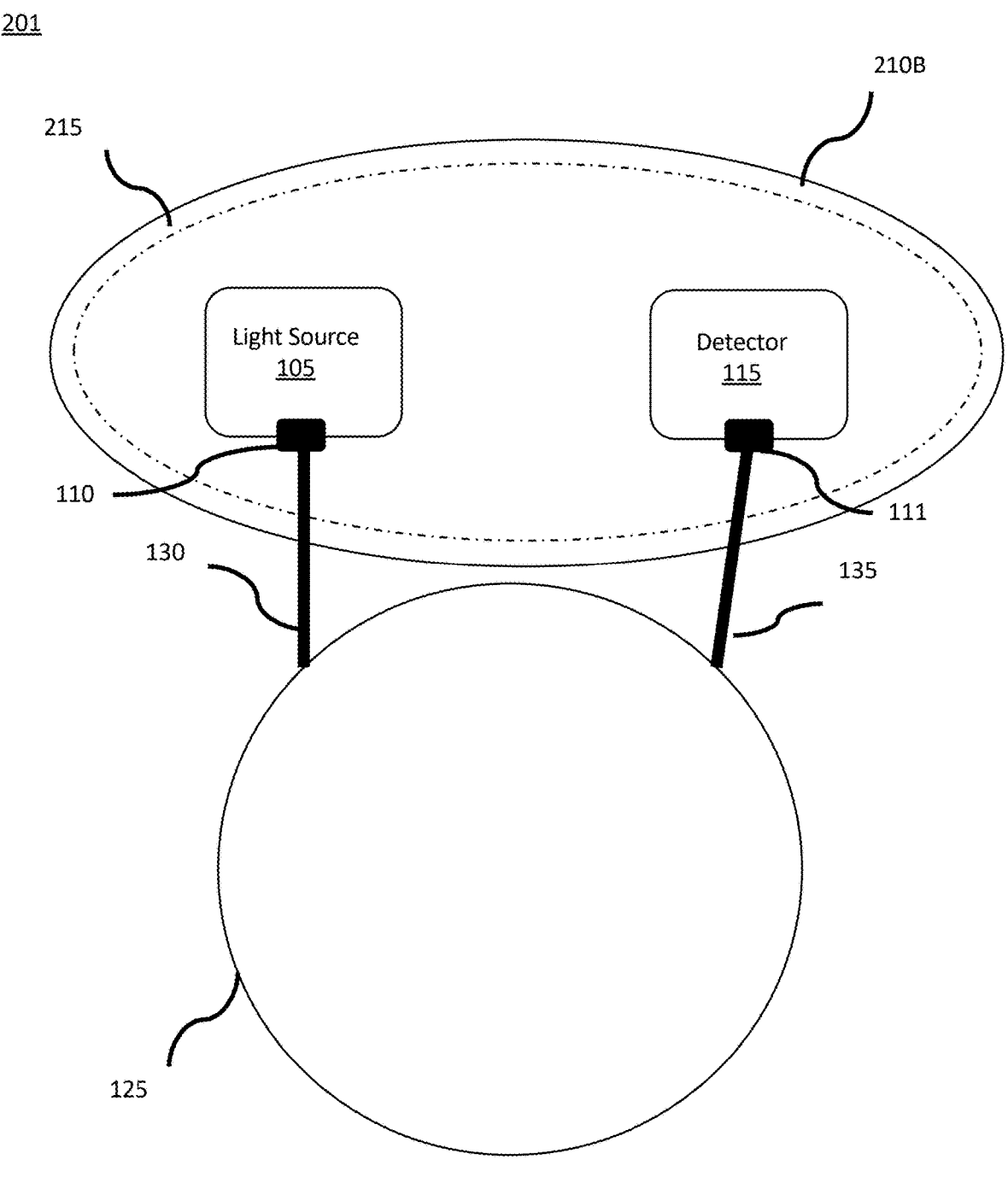
FIG. 2B provides a block diagram of an obtaining trans-abdominal fetal oximetry and/or trans-abdominal fetal pulse oximetry information that includes a covering member that covers some components of the system, in accordance with some embodiments of the present invention.
Figure 2C:
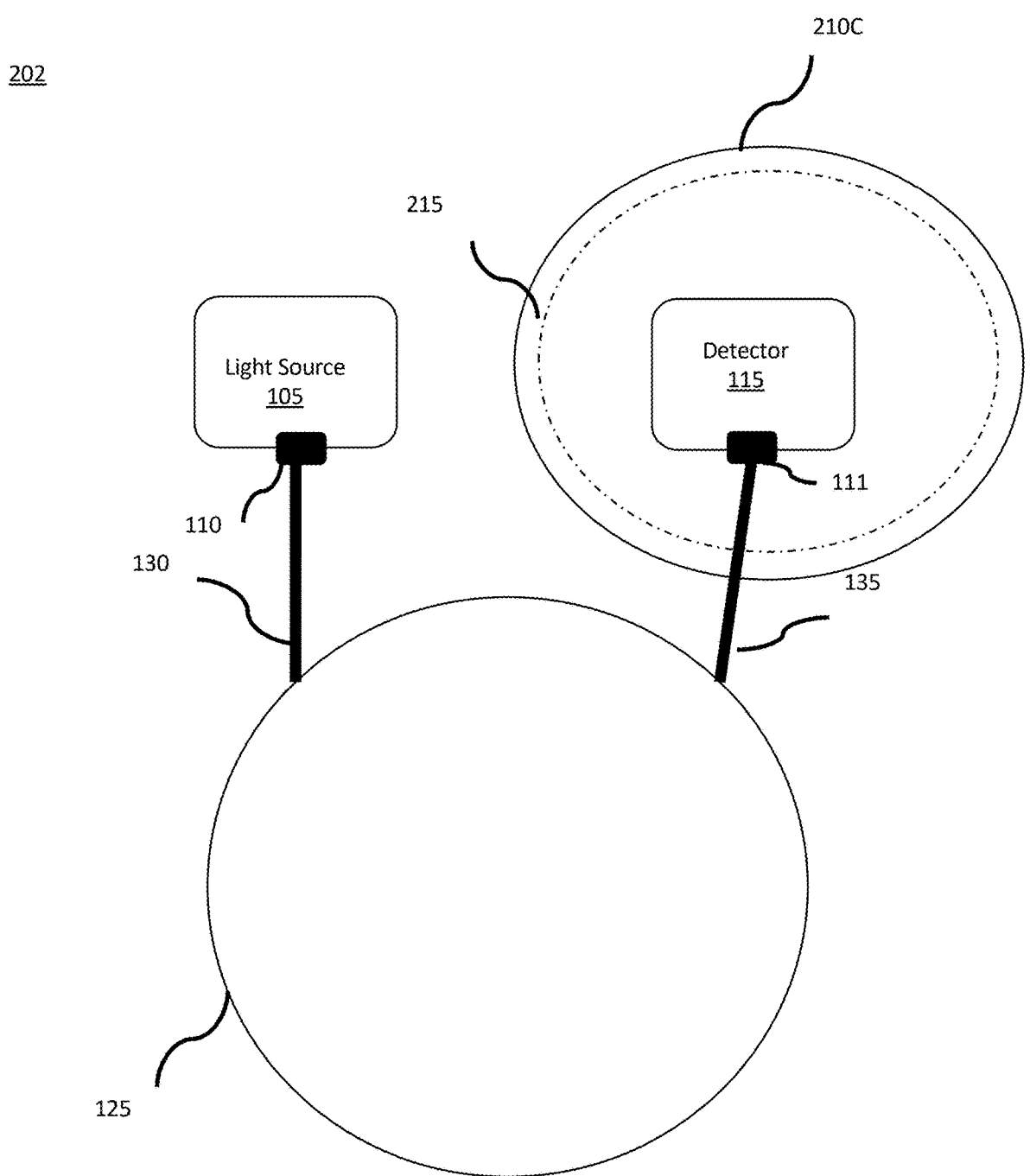
FIG. 2C provides a block diagram of an obtaining trans-abdominal fetal oximetry and/or trans-abdominal fetal pulse oximetry information that includes a covering member that covers some components of the system, in accordance with some embodiments of the present invention.

FIG. 2A illustrates an exemplary system 200 that includes the components of system 100 and a covering member 210A that covers all components of system 100. FIG. 2B illustrates an exemplary system 201 that includes the components of system 100 and a covering member 210B that covers light source 105, detector 115, and portions first and second arms 130 and 135. FIG. 2C illustrates an exemplary system 202 that includes the components of system 100 and a covering member 210C that covers detector 115 and a portion of second arm 135. Covering member(s) 210A, 210B, and 210C may be opaque or semi-opaque and may be adapted to shield the respective components of system 100 from, for example, ambient light that may be present in, for example, a room in which the pregnant mammal is residing. In some embodiments, covering member(s) 210A, 210B, and/or 210C may be transparent until an electrical current is applied. In some embodiments, covering member(s) 210A, 210B, and/or 210C may be opaque to certain wavelengths of light (e.g., red and/or infrared) but otherwise transparent.

Exemplary form factors for covering member(s) 210A, 210B, and/or 210C include, but are not limited to, a planar (i.e., flat) configuration that would act as a shade from ambient light coming from above, a curved configuration that would block ambient light coming from above and a portion of ambient light coming from a side of covering member 210A, 210B, and/or 210C, and a dome-like configuration configured so that a lower edge of covering member 210A, 210B, and/or 210C is adapted to be coincident with the skin of the pregnant mammal's abdomen when used and may thereby block nearly all ambient light from system 100 or components thereof.

In embodiments where covering member 210A, 210B, and/or 210C has a dome-like configuration, covering member(s) 210A, 210B, and/or 210C may further include an optional lip 215 by which to be coincident with the pregnant mammal's abdomen so as to facilitate, for example, blockage of nearly all ambient light from system 100 and/or components thereof and/or adhesion of system 200, 201, and/or 202 to the pregnant mammal's abdomen and/or attachment of system 200, 201, and/or 202 to the pregnant mammal's abdomen. Although the embodiments of system 200, 201, and 202, show lip 215 encircling the entirety of a lower edge of covering member 210A, 210B, and 210C, this need not always be the case as lip 215 may cover only a portion of the lower edge of covering member 210A, 210B, and 210C. In some instances, lip 215 may be configured so that an interface material (e.g., gel, alcohol, adhesive) may be applied thereto in order to affix lip 215 to the pregnant mammal's skin and/or form a seal between lip 215 and the pregnant mammal's skin. The interface material (not shown) may act to further block ambient light.

In some embodiments, covering member 210A, 210B, and/or 210C may be sized and/or positioned to accommodate the range(s) of motion of light source 105 and/or detector 115. In some instances, covering member 210A, 210B, and/or 210C may be articulated separately from system 100 or components thereof via, for example, a flexible or articulating member extending from housing 125, light source 105, detector 115, first arm 130, and/or second arm 135 (not shown). In these embodiments, movement of housing 125, light source 105, detector 115, first arm 130, and/or second arm 135 may result in a corresponding movement of covering member 210A, 210B, and 210C.

Additionally, or alternatively, covering member 210A, 210B, and/or 210C may be retractable from system 100 and/or components thereof so that the system 100 components may be articulated into a preferred position and then covering member 210A, 210B, and/or 210C may be positioned on top of them.

In some embodiments, covering member 210A, 210B, and/or 210C may be repositioned/re-oriented based on articulation of one or more components of system 100. This repositioning/re-orientation may be accomplished manually (e.g., via moving covering member 210A, 210B, and 210C by a user) and/or via a motor or other component (not shown).

Figure 3A:
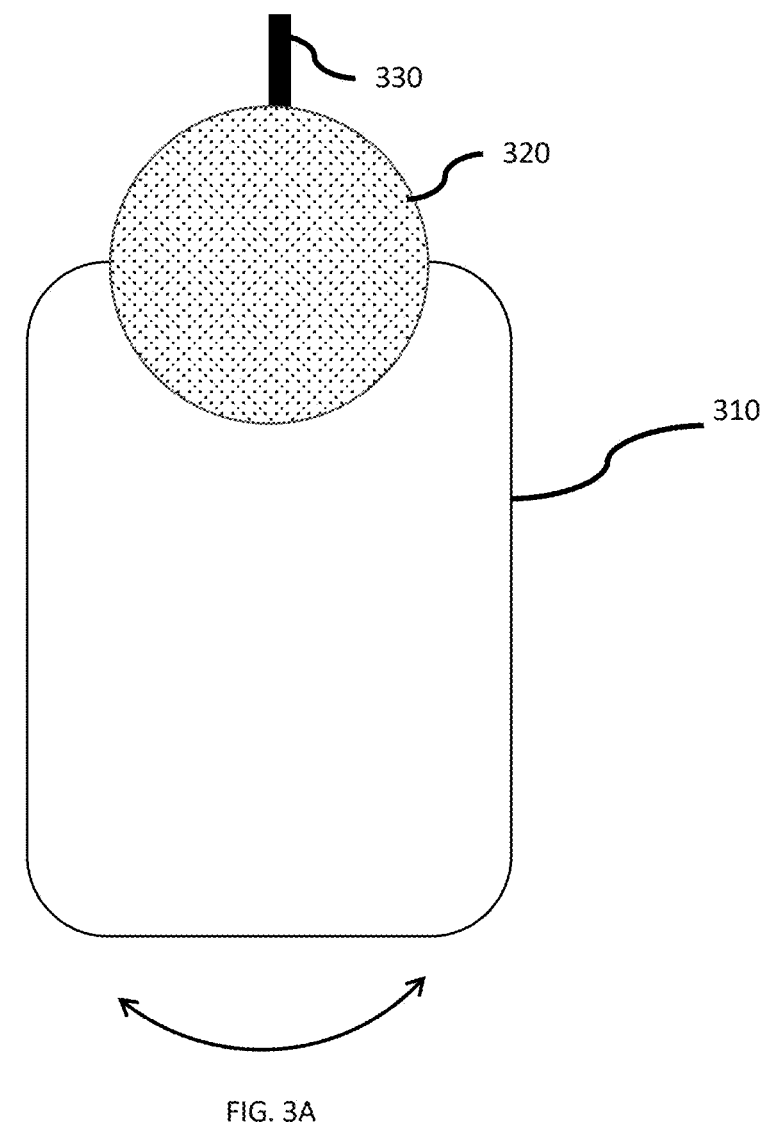
FIG. 3A illustrates an exemplary articulating fetal hemoglobin probe with a housing that rotates around a rotation member, in accordance with some embodiments of the present invention.
Figure 3B:
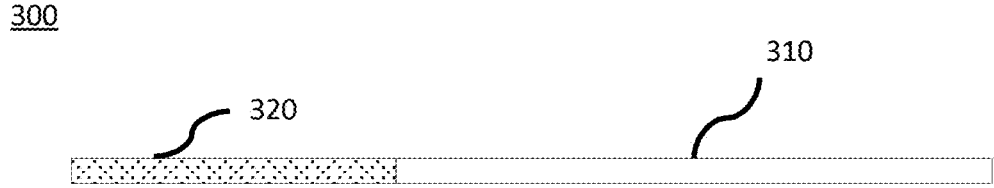
FIG. 3B illustrates a side view the exemplary articulating fetal hemoglobin probe of FIG. 3A, in accordance with some embodiments of the present invention.

FIGS. 3A and 3B show an exemplary articulating fetal hemoglobin probe 300 with a housing 310 that rotates around a rotation member 320. Fetal hemoglobin probe 300 also includes an optional cord 330 via which information may be communicated to and/or received from fetal hemoglobin probe 300 and/or power may be supplied to fetal hemoglobin probe 300. In some instances, rotation member 320 and/or housing 310 may include/house one or more of motor 120, controller 137, fan 132, transceiver 122, temperature probe 142, and/or fetal heart rate monitor 180 (not shown). Housing may rotate 360°, or some portion (e.g., 90°, 180°, 270°) thereof, around rotation member 320. In many embodiments, rotation member 320 and housing 310 will be aligned so that both are coincident with the skin of the pregnant mammal when deployed to monitor a fetus as shown in FIG. 3B. Fetal hemoglobin probe 300 may, in some instances, be flexible in the X, Y, and/or Z directions so that it may bend to be coincident with the abdomen of a pregnant mammal when placed thereon. In some embodiments, rotation member 320 may include an adhesive or other mechanism (e.g., suction cup) by which to attach to/stay on the skin of the pregnant mammal's abdomen. Housing 310 may be similar to, and/or include one or more components of, housings 410A-410F, as discussed below with regard to FIGS. 4A-4F.

System(s) 100, 200, 201, 202, and/or 300 and/or components included therein may be powered by, for example, an on-board power source (e.g., battery) present in, for example, housing 125 (not shown) and/or an electrical connection. In some embodiments, housing 125 and/or system(s) 100, 200, 201, 202, and/or 300 may be adapted to be worn by the pregnant mammal via, for example, elastic straps or a harness attached thereto.

In some instances, a position of a fetus within a pregnant woman's abdomen may be difficult to determine or discern and this may limit the ability of a health care provider to obtain fetal oximetry information and/or a detected electronic signal of sufficient strength and/or clarity. Moreover, a fetus may move while in the pregnant mammal's abdomen and such movement may necessitate repositioning of one or more components of system(s) 100, 200, 201, 202, and/or 300 so as to obtain a clearer and/or detected electronic signal that represents light that has been incident upon the fetus. In some embodiments of the present system, movement of one or more components of system(s) 100, 200, 201, 202, and/or 300 may be responsive to fetal movement and/or movement of the pregnant mammal. For example, when readings from fetal heart rate monitor 180 indicate that a fetus is at a first depth at a first time (i.e., T1) and at a second depth at a second time (i.e., T2), then controller 137 may instruct motor 120 to move light source 105 and/or detector 115 from their first position at T1 to a more advantageous second position at T2. Additionally, or alternatively, when an indication that a fetus has changed its orientation (not necessarily its depth), then controller 137 may communicate instructions to first and/or second arms 130 and/or 135 first and/or second attachment mechanism 110 and/or 111 to change the orientation and/or positioning of light source 105 and/or detector 115.

Articulation of components of system(s) 100, 200, 201, 202, and/or 300 responsively to movement by the fetus and/or pregnant mammal may be caused by, for example, manual manipulation (e.g., by an operator, technician, or physician) of first and/or second member(s) 130 and/or 135, first and/or second attachment mechanisms 110 and/or 111, housing 125, light source 105, and/or detector 115. Additionally, or alternatively, in some embodiments, the articulation may be facilitated by motor 120 and/or or other component capable of effecting movement that may be resident in first and/or second member(s) 130 and/or 135, first and/or second attachment mechanisms 110 and/or 111, housing 125, light source 105, and/or detector.

In some instances, the articulation of light source 105, detector 115, housing 125, first and/or second member(s) 130 and/or 135, and/or first and/or second attachment mechanisms 110 and/or 111 may be responsive to movement of a fetus and/or pregnant mammal and may be made automatically in response to information received by, for example, controller 137, fetal heart rate monitor 180, and/or detector 115. Additionally, or alternatively, the articulation may be responsive to information and/or instructions received by transceiver 122 from, for example, a computer coupled thereto.

In some embodiments, system(s) 100, 200, 201, 202, and/or 300 may be adapted to automatically track the movement of a fetus within the abdomen of a pregnant mammal and then automatically move components of the system so as to optimize the strength and/or clarity of the reflected signal.

FIGS. 4A-4F provide illustrations of additional exemplary fetal hemoglobin probes 400A-400F, respectively. In some embodiments, fetal hemoglobin probes 400A-400F, or a portion thereof, may be adapted to articulate in a manner similar to system(s) 100, 200, 201, 202, and/or 300. For example, one or more hemoglobin probes 400A-400F may be adapted to reside in and/or be fetal hemoglobin probe housing 310 shown in FIGS. 3A and 3B. Fetal hemoglobin probes 400A-400F are shown in FIGS. 4A-4F, as may be viewed from the outside (i.e., the patient facing side) of the housing without showing components (e.g., transceiver 107, controller 112, power supply 160, temperature probe 165, adjustment mechanism 122). Fetal hemoglobin probe(s) 115F-1151 may include an optional cable 420 through which power may be provided to fetal hemoglobin probe 400A-1151 and/or information may be communicated to, and/or received from, fetal hemoglobin probe 400A-1151 via, for example, coupling cable 420 to a computer like computer 150. Fetal hemoglobin probe(s) 115F-1151 include a plurality of light sources 105. In many instances one or more of these light sources 105 is configured to emit light in at least two distinct frequencies.

Figure 4A:
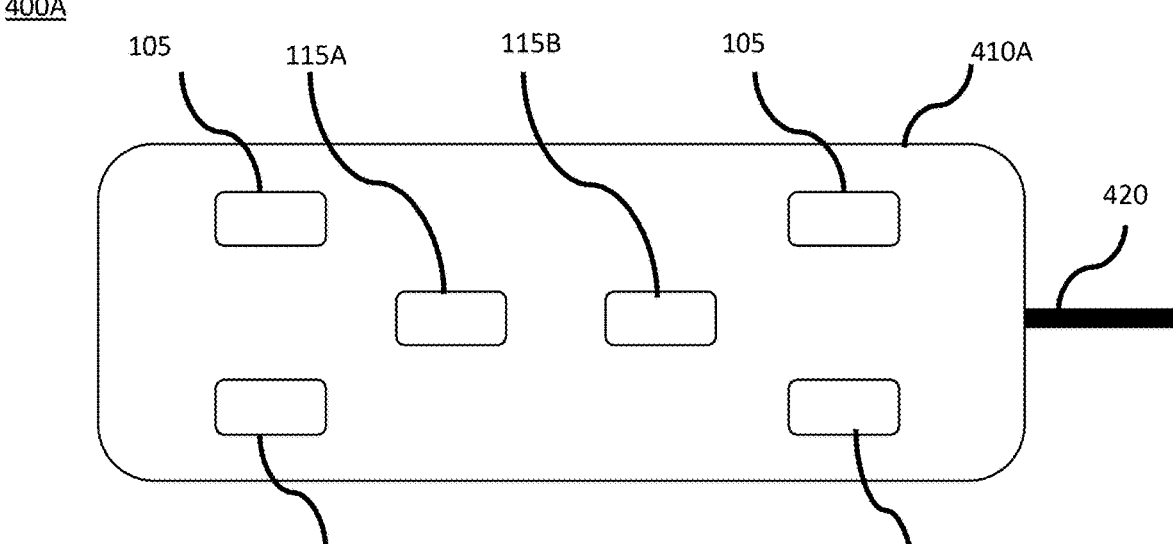
FIG. 4A illustrates an illustration of an exemplary fetal hemoglobin probe that includes two detectors and four light sources positioned within a housing, in accordance with some embodiments of the present invention.

FIG. 4A provides an illustration of an exemplary fetal hemoglobin probe 400A that includes two detectors 115A and 115B and four light sources 105 positioned within housing 410A. Each of the light sources 105 are positioned in a square-like configuration with each light source 105 being positioned near a corner of housing 410A. Detectors 115A and 115B are positioned in the center of housing 410A as shown.

Figure 4B:
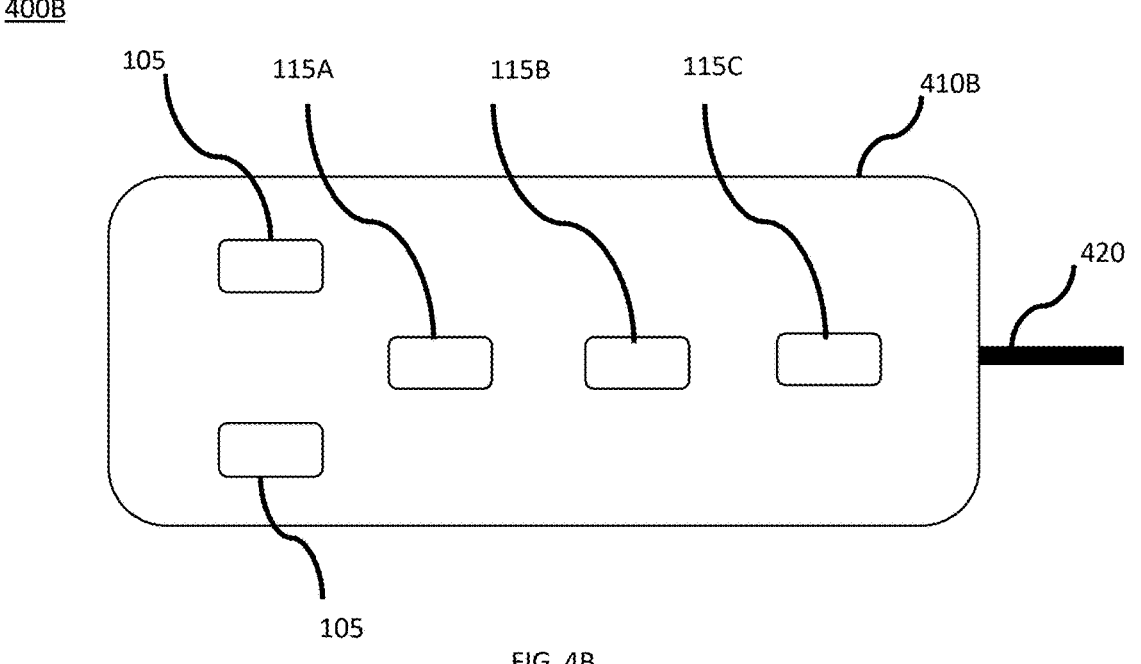
FIG. 4B illustrates an illustration of an exemplary fetal hemoglobin probe that includes three detectors and two light sources positioned within a housing, in accordance with some embodiments of the present invention.

FIG. 4B provides an illustration of an exemplary fetal hemoglobin probe 400B that includes three detectors 115A, 115B, and 115C and two light sources 105 positioned within housing 410B. The light sources 105 are vertically aligned with one another and positioned on the left side of housing 410B and the three light sources 115 are horizontally aligned with one another and extend across housing 410B so that a horizontal distance between first and second light sources 105 and first detector 115A is substantially equivalent to a horizontal distance between first detector 115A and second detector 115B, and a horizontal distance between second detector 115B and third detector 115C.

The amount of light detected by detector 115C may be less than the amount received by detector 115A. However, placing the detectors 115 progressively further away from the light sources 105 as shown in FIG. 4B serves to capture the reflected signal from different locations on the pregnant mammal's abdomen, which may later facilitate analysis of the received signals to, for example, isolate a portion of the detected electronic signal that corresponds to light that has been incident on the fetus from light that has only been incident on the pregnant mammal and/or is noise (e.g., ambient light, motion artifacts, etc.).

Figure 4C:
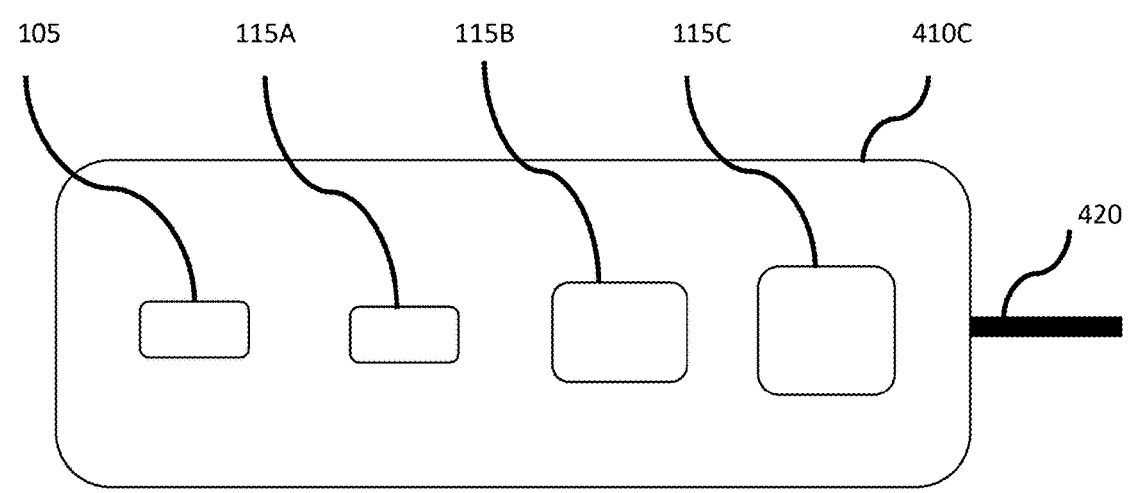
FIG. 4C illustrates an exemplary fetal hemoglobin probe that includes a light source and three detectors housed within a housing, in accordance with some embodiments of the present invention.

In some instances, it may be advantageous to increase the size and/or sensitivity (e.g., gain) of detectors 115 that are positioned further away from a light source 105 so as to, for example, capture fainter and/or more diffuse reflected signals. For example, FIG. 4C shows an exemplary fetal hemoglobin probe 400C that includes a light source 105, a first detector 115A, a second detector 115B, and a third detector 115C housed within housing 410C. In this arrangement, first detector 115A is smaller and/or less sensitive and third detector 115C is larger and/or more sensitive so that it may capture what is expected to be a fainter signal than the signal that may be detected by first detector 115A. The second detector 115B may have a size and/or sensitivity that falls between the size and/or sensitivities of first detector 115A and third detector 115C or is the same as the size or sensitivities of first detector 115A or third detector 115C.

Figure 4D:
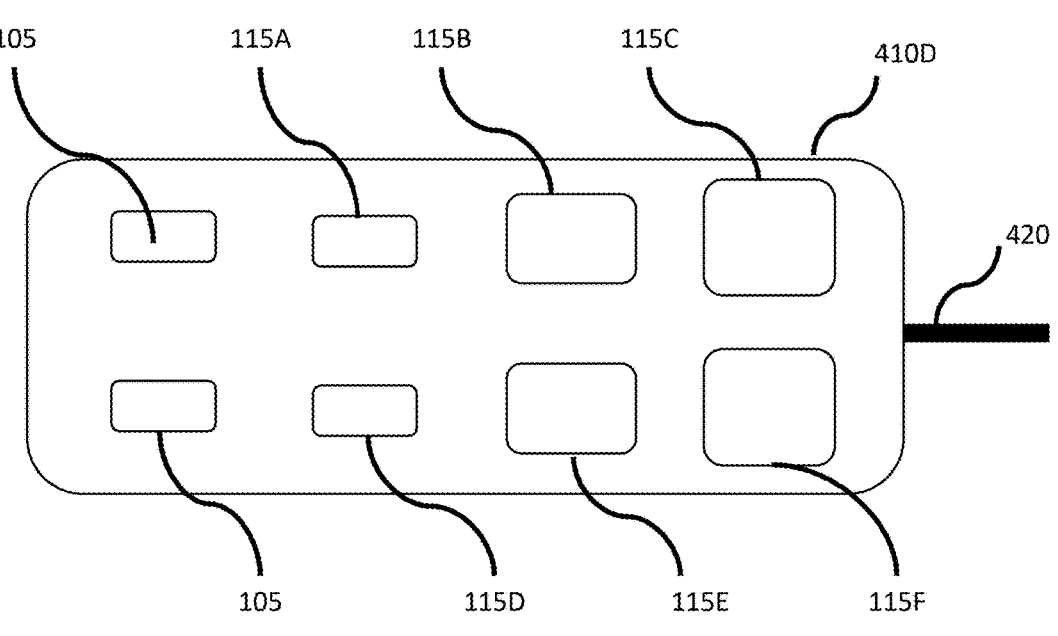
FIG. 4D illustrates an exemplary fetal hemoglobin probe that includes two light sources, a first set of two detectors, a second set of two detectors, and a third set of two detectors housed within a housing, in accordance with some embodiments of the present invention.
Figure 4E:
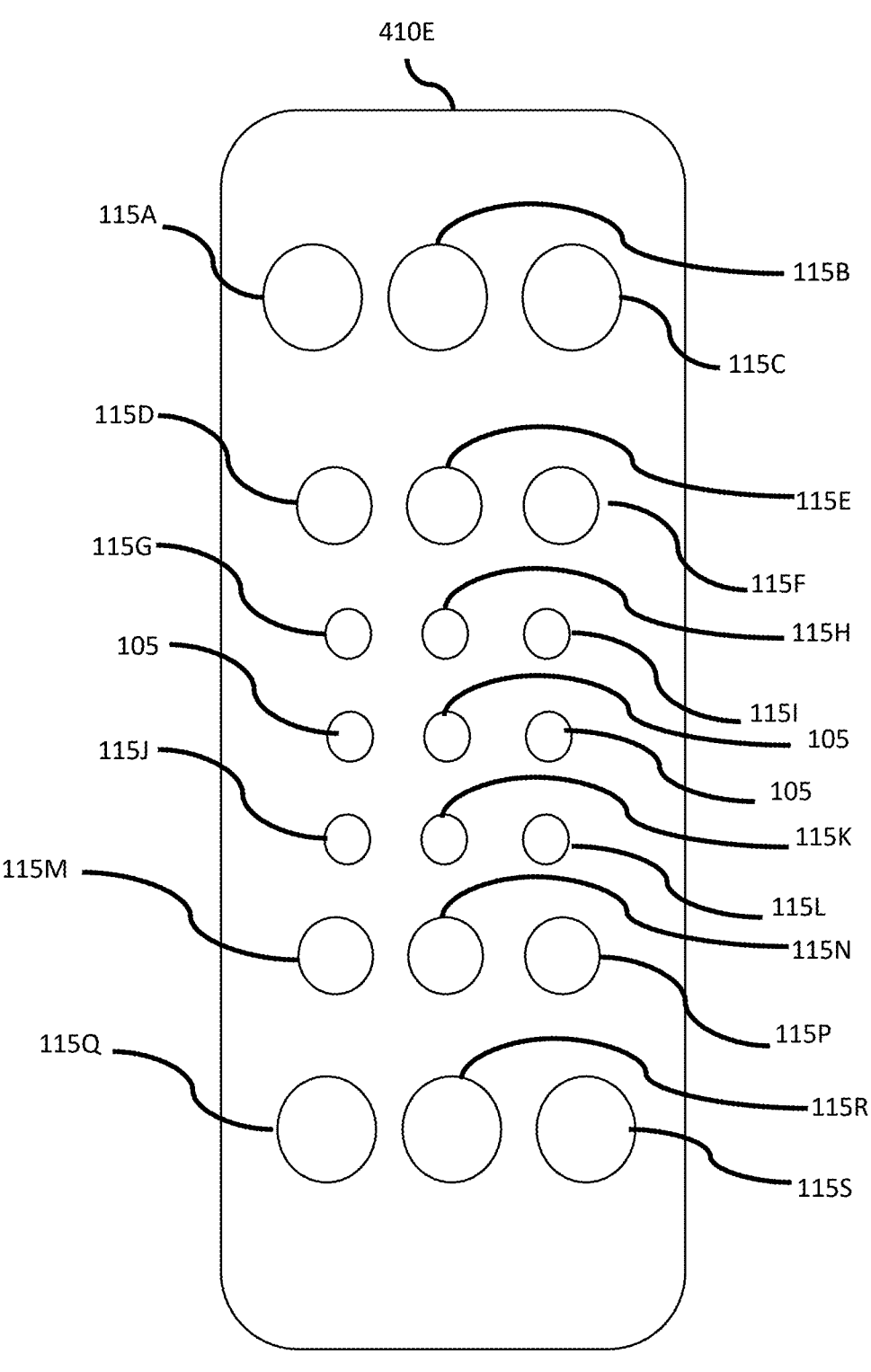
FIG. 4E illustrates an exemplary fetal hemoglobin probe that includes a plurality of light sources and detectors, in accordance with some embodiments of the present invention.
Figure 4F:
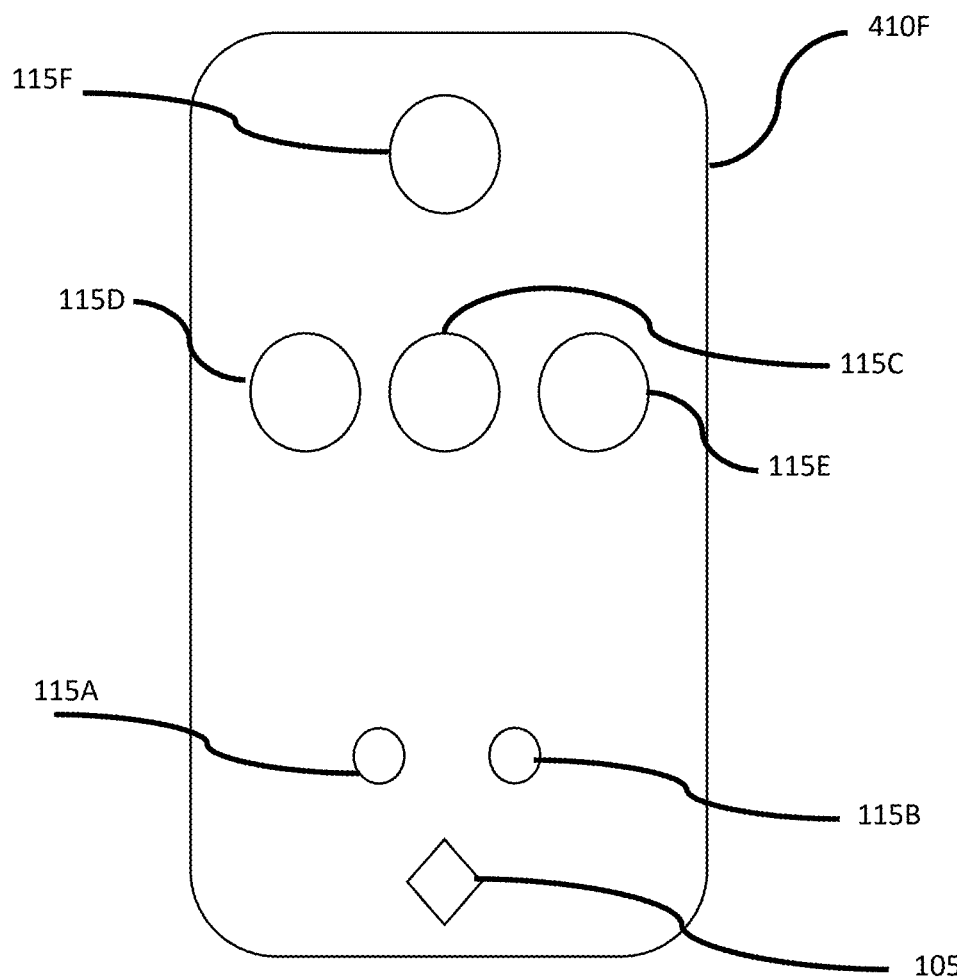
FIG. 4F illustrates an exemplary fetal hemoglobin probe that includes a plurality of light sources and detectors, in accordance with some embodiments of the present invention.

Fetal hemoglobin probes 400D, 400E, and 400F of FIGS. 4D, 4E, and 4F, respectively, provide other examples of fetal hemoglobin probes that include detectors of varying size. More specifically, fetal hemoglobin probe 400D provides two rows of detectors that are similar to the row of detectors provided by fetal hemoglobin probe 400C in that detectors 115A and 115D, which are positioned closest to the light sources 105, are the smallest/lowest gain detectors and detectors 115C and 115F, which are positioned the furthest from light sources 105 are the largest/highest gain detectors. Detectors 115B and 115E, which are positioned between detectors 115A and 115D; and 115C and 115F, respectively, may have a size and/or gain that is similar to, or larger than detectors 115A and 115D and/or may have a size and/or gain that is similar to, or smaller than detectors 115C and 115F.

Fetal hemoglobin probe 400E includes a row of three light sources 105 substantially aligned with one another along the X-axis with nine detectors 115 positioned above the light sources 105 in three rows with three columns and nine detectors 115A-115S positioned above and below the light sources 105 in three rows with three columns each. As with fetal hemoglobin probes 400C, and 400D, detectors 115 (e.g., 115J-115C and 115Q-115S) positioned closer to light sources 105 are smaller/have a lower gain and detectors (e.g., 115A-115L and 115G-115I) positioned further away from light sources 105 are larger/have a larger gain.

FIG. 4F provides an illustration of an exemplary fetal hemoglobin probe 400F that includes one light source 105 and a plurality of detectors 115A-115F positioned within a housing 410F. In some instances, fetal hemoglobin probe 400F may include multiple light sources 105. A first and second detector 115A and 115B, respectively, may be positioned approximately 1.5-4 cm (along the Y-axis) from the light source and there may be a distance of approximately 1-4 cm (along the Y-axis) between them. In most instances, the first and second detectors 115A and 115B will be the same distance from light source 105 (as shown in FIG. 4F) but this need not always be the case. For example, detector 115A may be 2 cm from light source 105 and detector 115B may be 4 cm from light source 105. Due to their relatively close proximity to light source 105, the signals detected by first and/or second detector(s) 115A and 115B may detect a signal primarily generated by light reflected by the pregnant mammal, with little contribution from light reflected from the fetus, and these signals may be used to, for example, determine motion artifacts of the pregnant mammal, photoplethysmogram information (e.g., photoplethysmogram variation), heartbeat information, and so on.

In some circumstances, first and/or second detector(s) 115A and 115B may be smaller and/or relatively less sensitive (e.g., lower gain) than other detectors resident in housing 410F. Even though first and/or second detector(s) 115A and 115B may be smaller and/or relatively less sensitive, it is expected that they will still detect a signal of adequate strength due, at least in part, on their respective relatively close proximity to the light source 105. Using detectors of smaller size/lower sensitivity for first and/or second detector(s) 115A and 115B may serve to, for example, reduce the cost of manufacturing fetal hemoglobin probe 410D and decrease the overall size of fetal hemoglobin probe 410D, which may make wearing fetal hemoglobin probe 410D more comfortable for the pregnant mammal.

A third detector 115C, a fourth detector 115D, and a fifth detector 115E may be positioned within housing 410F, for example, approximately 5-10 cm (along the Y-axis) from light source 105 and there may be a distance of, for example, approximately 1-8 cm (along the Y-axis) between them. In most instances, the third, fourth, and fifth detectors 115C, 115D, and/or 115E may be the same distance from light source 105 (as shown in FIG. 4F) but this need not always be the case. For example, detector 115C may be 2 cm from light source 105 and detector 115D may be 5 cm from light source 105.

In many instances, third, fourth, and fifth detectors 115C, 115D, and 115E may be larger in size (e.g., larger surface area over which to detect a reflected optical signal) and/or have a greater gain than detectors 115A and/or 115B. A signal reflected from the pregnant mammal's abdomen is expected to be weaker and more diffuse further away from the light source and the greater gain/size third, fourth, and fifth detectors 115C, 115D, and 115E may be useful in detecting this relatively fainter/more diffuse reflected optical signal.

Because third, fourth, and fifth detectors 115C, 115D, and 115E are positioned further away from light source 105, a greater portion of a signal detected by these detectors (when compared to the signals detected by detectors 115A and 115B) may be reflected from the fetus. Stated differently, because the light reflected from the pregnant mammal's abdomen is expected to be more diffuse further away from the light source, a detector positioned further away from the light source may be expected to detect light reflected from a more diffuse area of the pregnant mammal's abdomen, including the fetus contained therein. Thus, it is likely that a greater proportion of the signals detected by third, fourth, and fifth detectors 115C, 115D, and 115E may be incident upon the fetus. This may result in detected signal with a higher fetal/pregnant mammal ratio. The three signals detected by third, fourth, and fifth detectors 115C, 115D, and 115E may then be correlated with, for example, one another, a signal detected by first detector 115A, a signal detected by second detector 115B, and/or one or more secondary signals (e.g., fetal heartbeat, maternal heartbeat) in order to, for example, amplify or otherwise strengthen the portion of the signal reflected from the fetus (fetal signal) and/or isolate the fetal signal from the total signal.

A sixth detector 115F may be positioned within housing 410F, for example, approximately 4-13 cm (along the Y-axis) from light source 105. In some embodiments, sixth detector 115F may be of the same size and/or gain as third, fourth, and/or fifth detectors 115C, 115D, and/or 115E and, in other embodiments, may be larger in size and/or higher in gain so as to, for example, detect a signal of sufficient strength given its relative distance from light source 105.

A signal detected by sixth detector 115F may provide a signal with a fetal/pregnant mammal ratio when compared with the signals detected by first, second, third, fourth, and/or fifth detectors 115A, 115B, 115C, 115D, and/or 115E due, in part, on its proximity to light source 105.

One or more of the plurality of detectors described above with regard to fetal hemoglobin probes 400A-400E may be used in a manner similar to the manner(s) described above with regard to one or more of detectors 115A-115E.

Figure 5A:
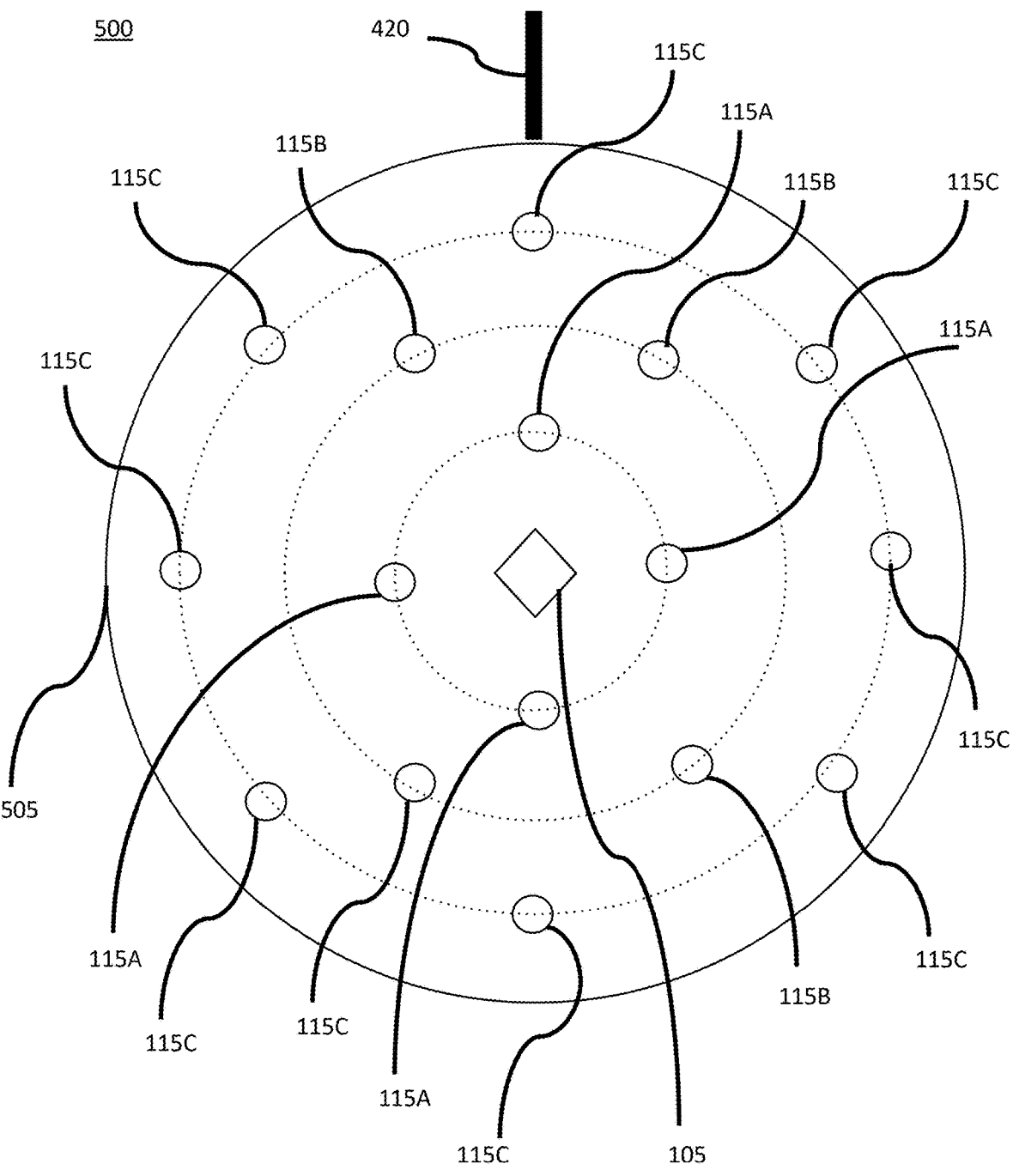
FIG. 5A illustrates a first exemplary disk-shaped fetal hemoglobin probe, in accordance with some embodiments of the present invention, in accordance with some embodiments of the present invention.

FIG. 5A provides a first exemplary circularly-shaped fetal hemoglobin probe 500, that includes a light source 105 positioned at the center of the circle and a plurality of detectors positioned in three concentric rings radiating outward from light source 105. More specifically, fetal hemoglobin probe 500 includes a first ring of four detectors 115A that is closest to light source 105, a third ring of eight detectors 115C farthest from light source 105, and a second ring of six detectors 115B located between the first and third rings. Light source 105 and detectors 115A, 115B, and/or 115C may be housed in a circularly-shaped housing 505. In some embodiments, housing 505 may include one or more mechanisms to facilitate attachment of fetal hemoglobin probe 500 to a pregnant mammal. Detectors 115A, 115B, and/or 115C may be of the same size or detector gain and/or have different sizes and different detector gain distributed throughout fetal hemoglobin probe 500.

Due to their relatively close proximity to light source 105, the signals detected by first detector(s) 115A may detect a signal primarily generated by light incident upon the fetus, whereas detectors 115B and 115C would detect incident upon the pregnant mammal and the fetus.

Figure 5B:
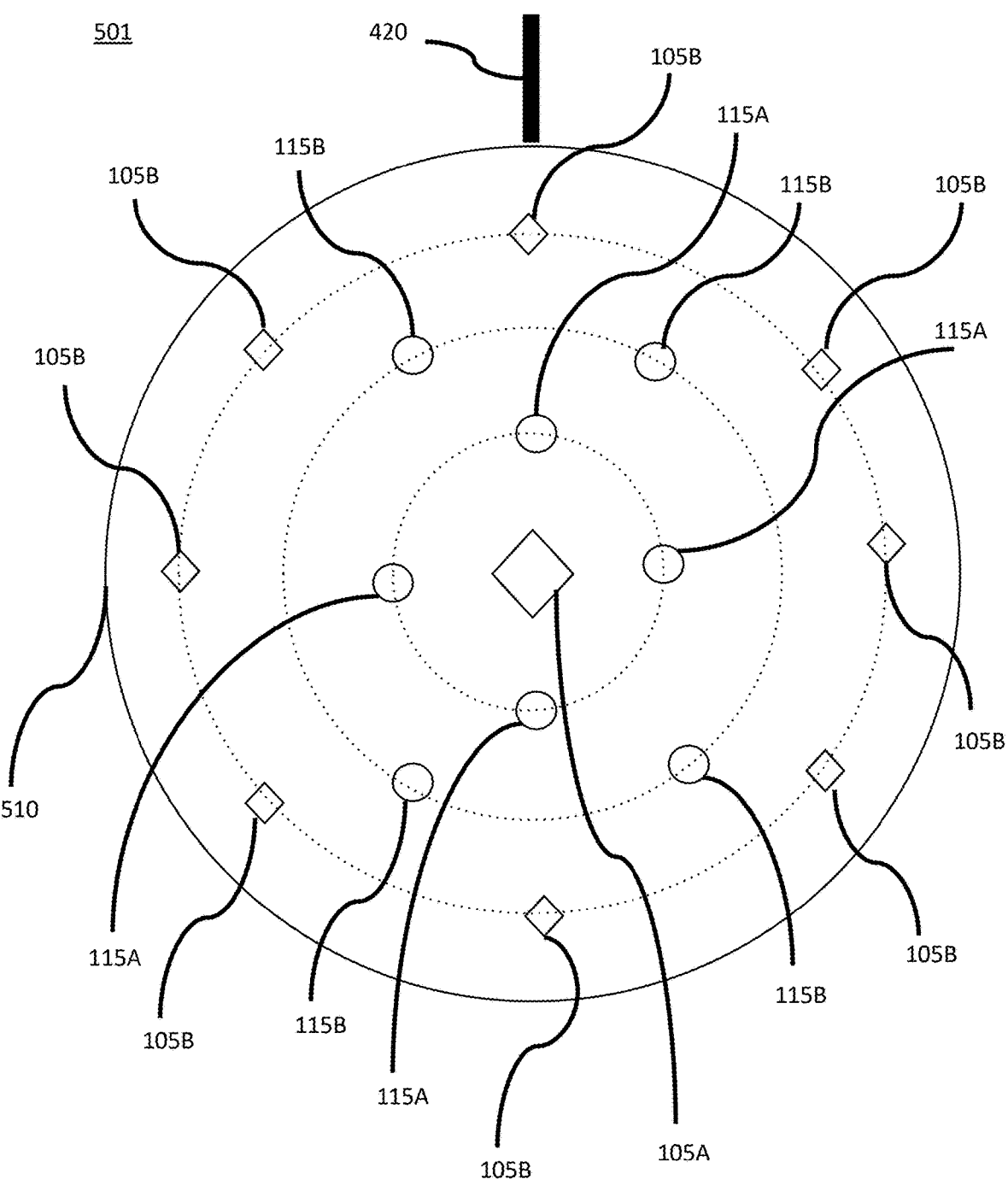
FIG. 5B illustrates a second exemplary disk-shaped fetal hemoglobin probe, in accordance with some embodiments of the present invention.

FIG. 5B provides a second exemplary circularly-shaped fetal hemoglobin probe 501, that includes a center light source 105A positioned at the center of the circle, a plurality of detectors positioned in three concentric rings radiating outward from light source 105A, and a plurality of second light sources 105B positioned in a concentric ring after the third ring of detectors. Fetal hemoglobin probe 115B is similar to fetal hemoglobin probe 115A except that it has the ring of second light sources 105B. More specifically, fetal hemoglobin probe 501 includes a first ring of four detectors 115A that is closest to light source 105, a third ring of eight detectors 115C farthest from light source 105, a second ring of six detectors 115B located between the first and third rings, and a ring second light sources 105B positioned furthest away from first light source 105A.

First light source 105A, detectors 115A, 115B, and/or 115C, and second light sources 105C may be housed in a circularly shaped housing 510. In some embodiments, housing 505 may include one or more mechanisms to facilitate attachment of fetal hemoglobin probe 501 to a pregnant mammal. Detectors 115A, 115B, and/or 115C may be of the same size or detector gain and/or have different sizes and different detector gain distributed throughout fetal hemoglobin probe 500.

Figure 6A:
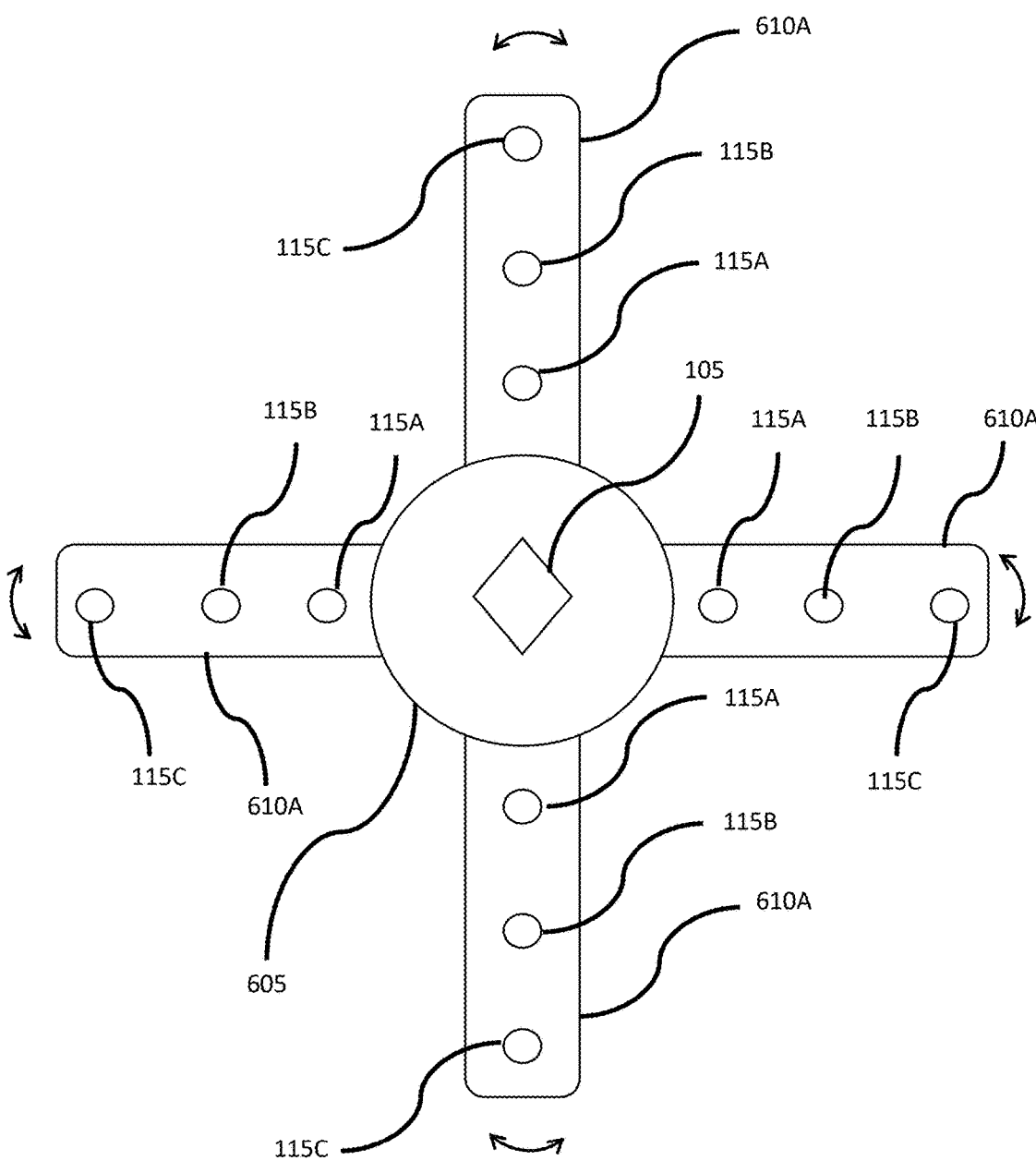
FIG. 6A illustrates a first exemplary fetal hemoglobin probe that includes a central hub and four movable arms extending therefrom, in accordance with some embodiments of the present invention.

FIG. 6A provides an illustration of a fetal hemoglobin probe 600, which includes a plurality of detectors 115 positioned on four movable arms 610A extending from a circularly-shaped center piece 605, which houses light source 105. More specifically, each arm 610A includes three detectors, 115A, 115B, and 115C with detector 115A being positioned closes to light source 105 and detector 115C being positioned furthest away from light source 105. These detectors may be of the same size or detector gain and/or have different sizes and different detector gain distributed throughout the detector. In some embodiments, centerpiece 605 may be similar to housing 125 in that it may house one or more components in addition to light source 105. Optional additional components included in housing 605 include, but are not limited to, ultrasound device and/or fetal heart rate monitor 180, motor 120, transceiver 122, fan 132, controller 137, power source 195, processor 185, display 190, and/or temperature probe 142 as shown in, for example, FIG. 1K and discussed above.

Due to their relatively close proximity to light source 105, the signals detected by first detector(s) 115A may detect a signal primarily generated by light that has been incident upon the fetus, whereas detectors 115B and 115C may detect light that has been incident upon the pregnant mammal and her fetus.

Figure 6B:
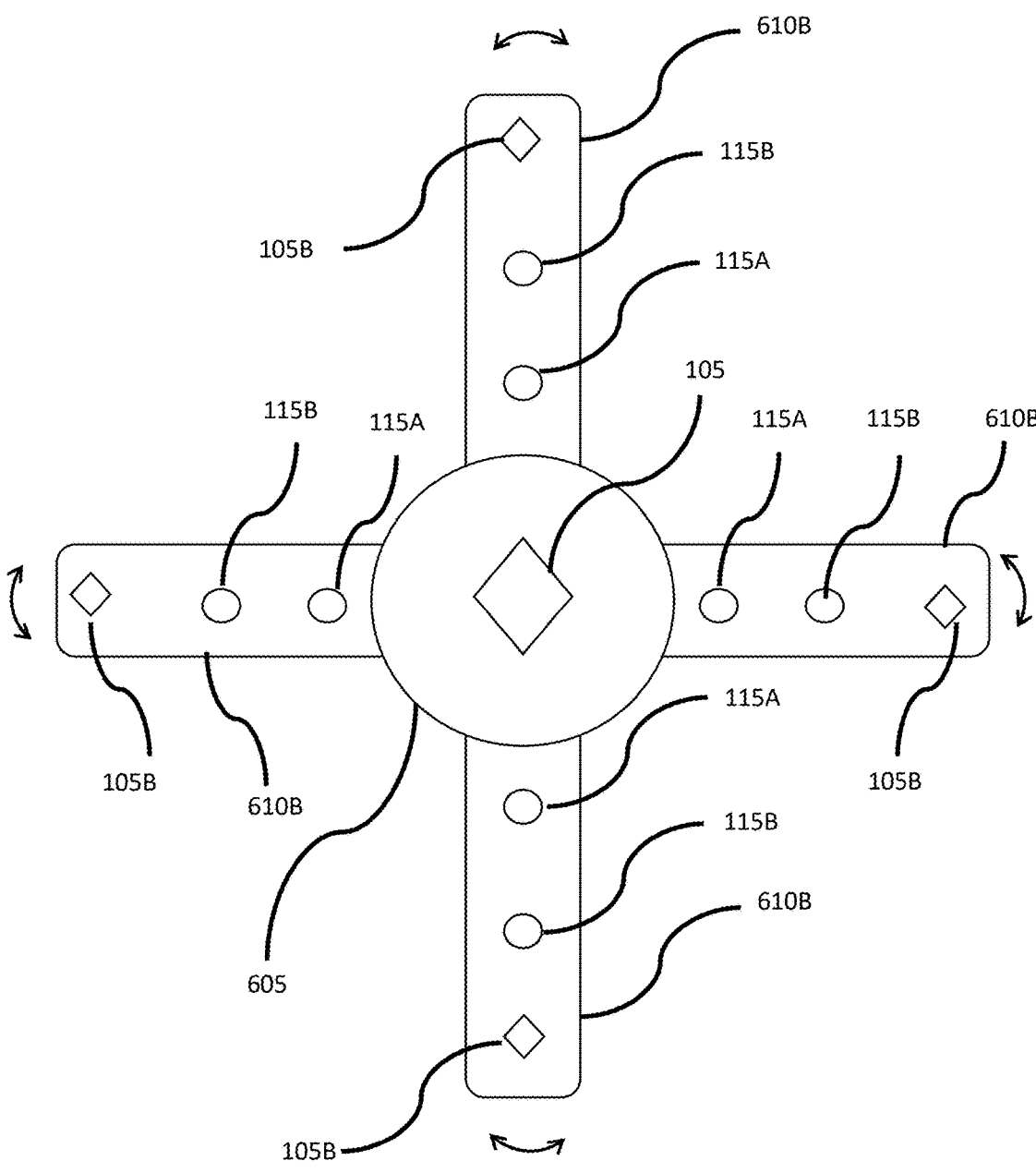
FIG. 6B illustrates a second exemplary fetal hemoglobin probe that includes a central hub and four movable arms extending therefrom, showing additional light sources, in accordance with some embodiments of the present invention.

FIG. 6B provides an illustration of a fetal hemoglobin probe 601, which includes a plurality of detectors 115 and a plurality of second light sources positioned on four movable arms 610B extending from a circularly-shaped center 605, which houses a first light source 105A. More specifically, each arm 610B includes two detectors, 115A and 115B with detector 115A being positioned closes to light source 105 and detector 115B being positioned further away from first light source 105A. Each arm also includes a second light source 105B positioned at the end of each arm 610B. These detectors may be of the same size or detector gain and/or have different sizes and different detector gain distributed throughout the detector.

Figure 7A:
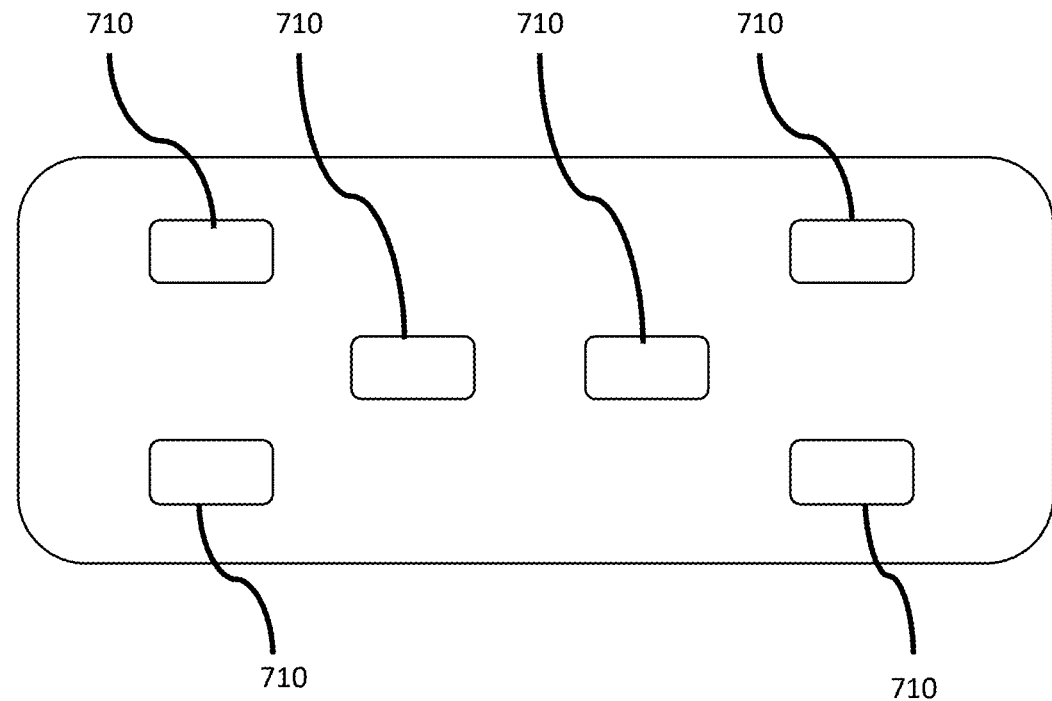
FIG. 7A illustrates an exemplary cover that may cover a portion of housing shown in FIG. 4A, in accordance with some embodiments of the present invention.
Figure 7B:
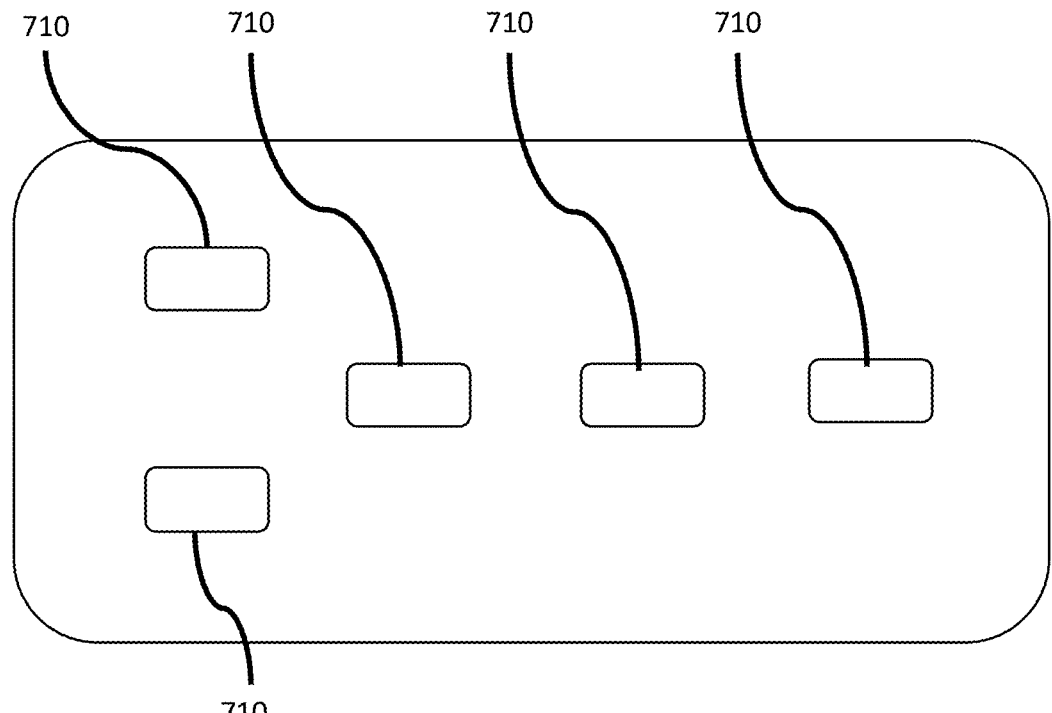
FIG. 7B illustrates an exemplary cover that may cover a portion of housing shown in FIG. 4B, in accordance with some embodiments of the present invention.
Figure 7C:
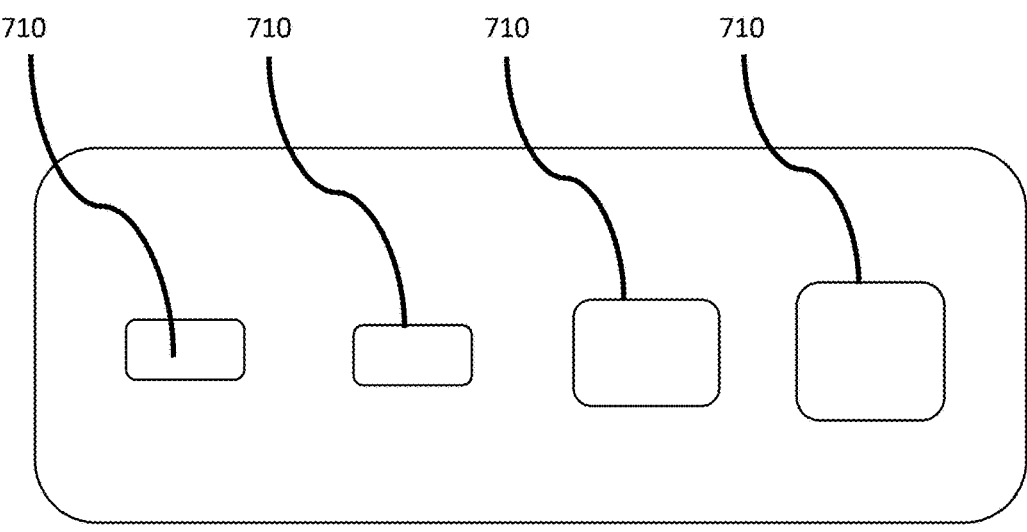
FIG. 7C illustrates an exemplary cover that may cover a portion of housing shown in FIG. 4C, in accordance with some embodiments of the present invention.
Figure 7D:
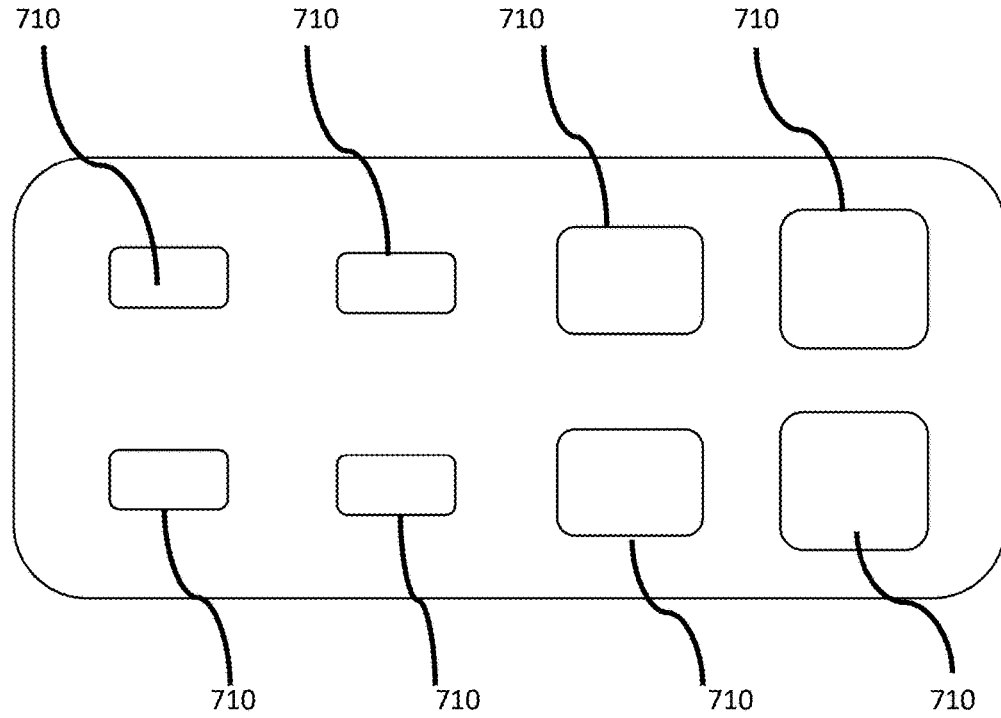
FIG. 7D illustrates an exemplary cover that may cover a portion of housing shown in FIG. 4D, in accordance with some embodiments of the present invention.
Figure 7E:
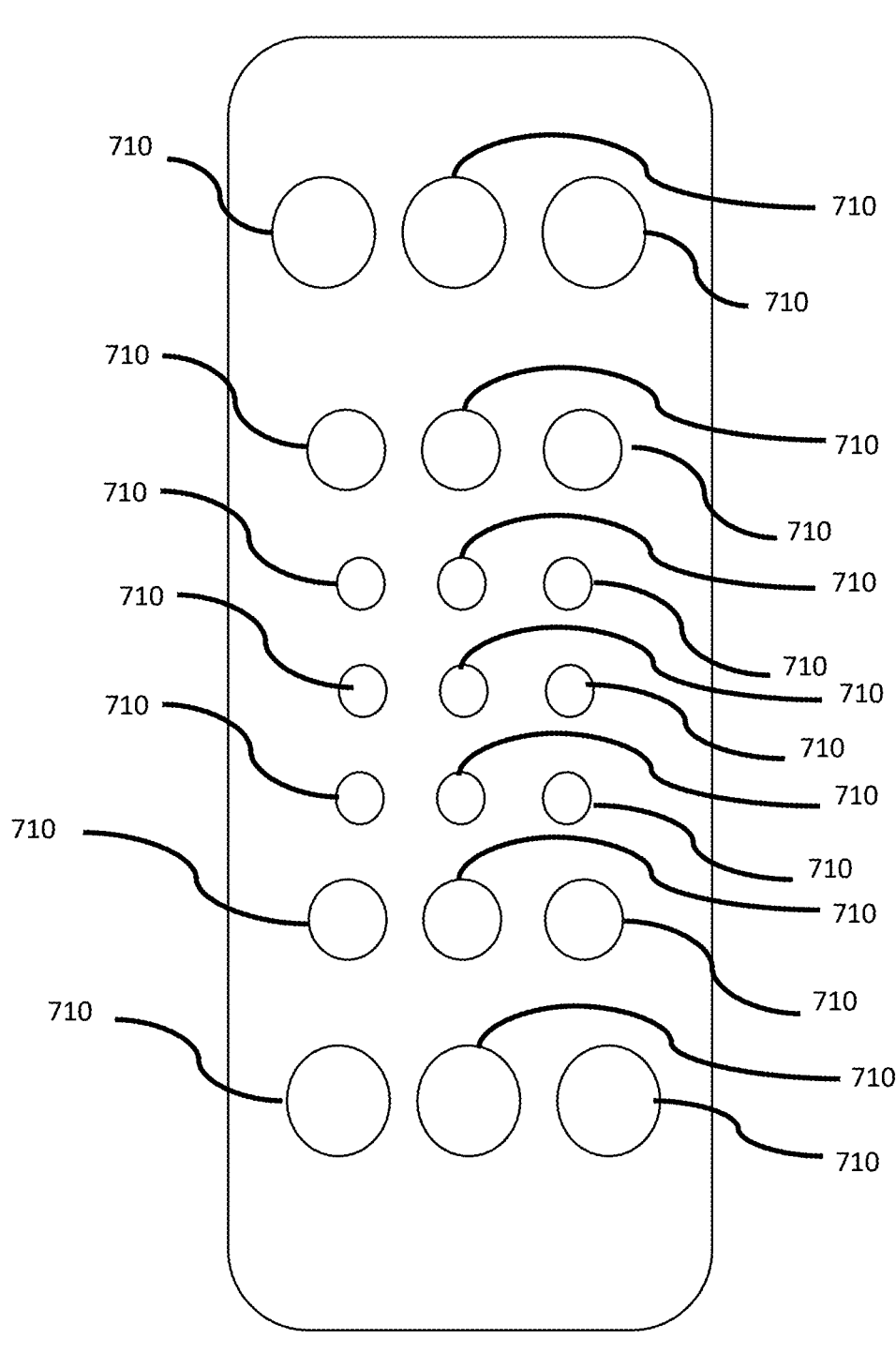
FIG. 7E illustrates an exemplary cover that may cover a portion of housing shown in FIG. 4E, in accordance with some embodiments of the present invention.
Figure 7F:
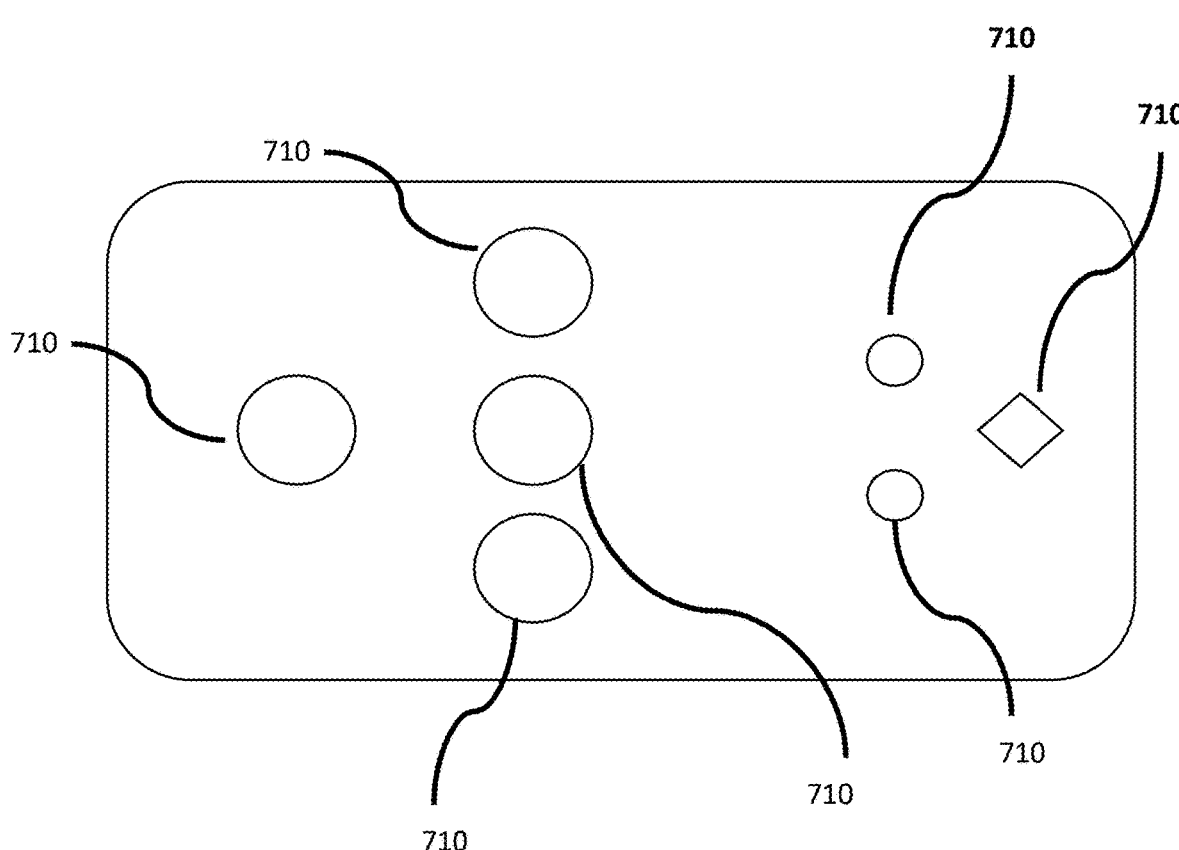
FIG. 7F illustrates an exemplary cover that may cover a portion of housing shown in FIG. 4F, in accordance with some embodiments of the present invention.

FIGS. 7A-7F provide exemplary covers, or sleeves, 700A-700F that may cover a portion (i.e., a surface configured to be in contact with the skin of the pregnant mammal) of housings 410A-410F, respectively. When embodied as a cover, cover/sleeve 700A-700F may be a single sheet or sticker that is applied to the surface of housings 410A-410F, respectively. When embodied as a sleeve, cover/sleeve include may be a first side, as shown in FIGS. 7A-7F and a second side as shown in FIG. 7F with a slit therebetween into which a respective one housings 410A-410F may be inserted. Each cover/sleeve 700A-700E is configured to accommodate the light sources and detectors of a particular housing configuration and includes a plurality of openings 710. Openings 710 may be transparent portions of a cover and/or may be portions of a cover that do not include any material (e.g., a hole in the cover). The openings 710 may be arranged to be coincident with the detectors and/or light sources of a particular housing 410A-410F so that light may pass from a light source and reflections of that light be detected be detected by one or more of the detectors. For example, cover 700A of FIG. 7A has a plurality of openings 710 arranged to be coincident with the arrangement of light sources 105 and detectors 115 of housing 410A. Likewise, cover 700B of FIG. 7B has a plurality of openings 710 arranged to be coincident with the arrangement of light sources 105 and detectors 115 of housing 410B, cover 700C of FIG. 7C has a plurality of openings 710 arranged to be coincident with the arrangement of light sources 105 and detectors 115 of housing 410C, cover 700D of FIG. 7D has a plurality of openings 710 arranged to be coincident with the arrangement of light sources 105 and detectors 115 of housing 410D, and cover 700E of FIG. 7E has a plurality of openings 710 arranged to be coincident with the arrangement of light sources 105 and detectors 115 of housing 410E.

In some cases, a cover 700A-700F may include an adhesive that facilitates adhesion of a housing to a pregnant mammal's skin. Additionally, or alternatively, a portion of cover 700A-700E may be fully opaque or partially opaque (e.g., to a certain intensity or wavelength of light). The opacity of cover 700A-700E may serve to limit, or block, ambient light from entering the pregnant mammal's abdomen and/or being detected by a detector 115.

FIGS. 8A, 8B, 8C, and 8D provide examples of emission-side views of exemplary light sources 801, 802, 803, and 804, respectively. Light sources 801, 802, 803, and 804 include a plurality of light producing elements 815 configured to emit light of the same and/or different wavelengths. More particularly, exemplary light source 801 shown in FIG. 8A includes a housing 805 and two light emitting elements 815A and 815B. Housing 805 may be a housing configured to house light emitting elements 815A and 815B and provide power thereto via, for example, an on-board battery and/or external power source (e.g., electrical main). Often, light emitting element 815A will emit light of a wavelength that is different from the wavelength of light emitted by light emitting element 815B. For example, light emitting element 815A may emit red light and light emitting element 815A may emit infrared light. Analysis of light detected at both of these wavelengths may enable pulse oximetry calculations and/or hemoglobin oxygen saturation levels.

Figure 8A:
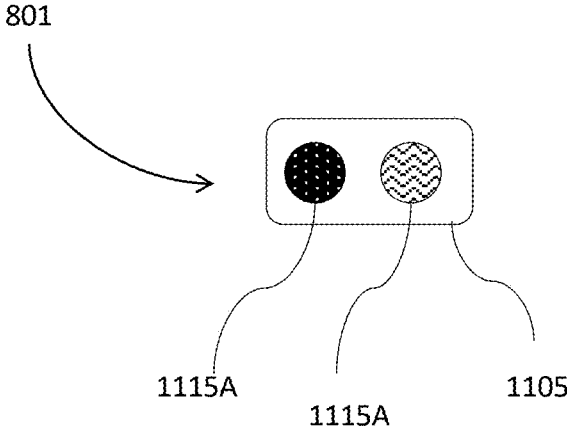
FIG. 8A is a block diagram showing an emission-side view of an exemplary light source, consistent with some embodiments of the present invention.
Figure 8B:
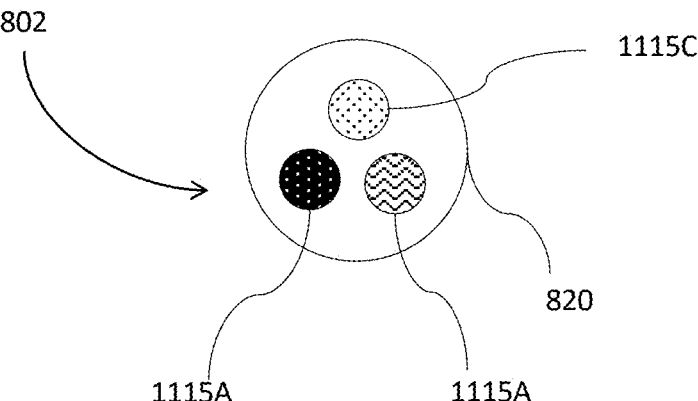
FIG. 8B is a block diagram showing an emission-side view of an exemplary light source, consistent with some embodiments of the present invention.

Exemplary light source 802 shown in FIG. 8B includes a housing 820 and three light emitting elements, 815A, 815B, and 815C. Often, each light emitting element 815A, 815B, and 815C will emit light of a different wavelength.

Figure 8C:
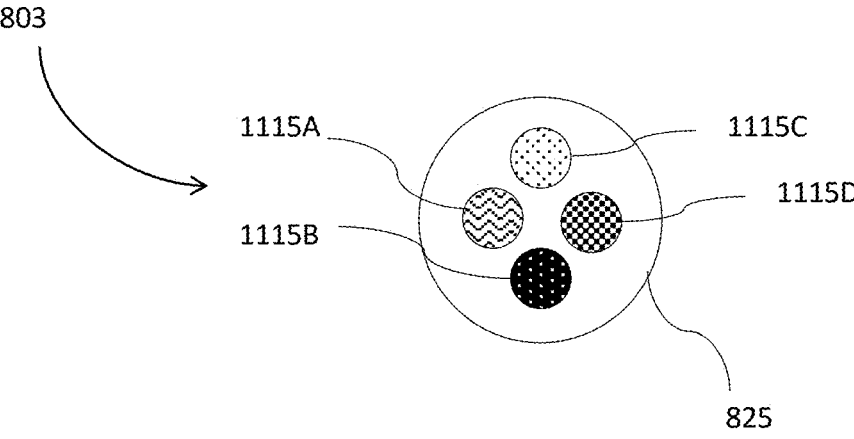
FIG. 8C is a block diagram showing an emission-side view of an exemplary light source, consistent with some embodiments of the present invention.

Exemplary light source 803 shown in FIG. 8C includes a housing 825 and four light emitting elements, 815A, 815B, 815C, and 815D. Each light emitting element 815A, 815B, 815C, and 815D may emit light of a different wavelength. This may serve to provide a broad spectrum of light wavelengths that may be directed into the pregnant mammal's abdomen.

Figure 8D:
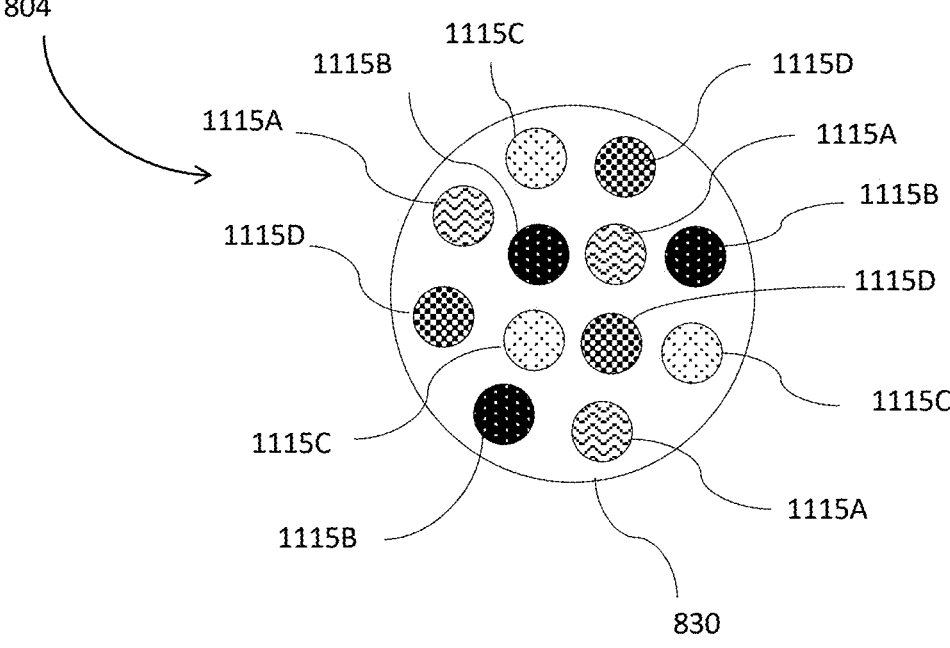
FIG. 8D is a block diagram showing an emission-side view of an exemplary light source, consistent with some embodiments of the present invention.

Exemplary light source 804 shown in FIG. 8D includes a housing 830 and three sets of light emitting elements, 815A, 815B, 815, and 815D (twelve in all) arranged in a pattern. Light emitting elements, 815A, 815B, 815, and 815D may be arranged within housing 830 so that a distance between light sources of the same frequency is maximized. This may cause the projection of light of a particular wavelength to be spread out over a larger surface are of the epidermis.

Exemplary light emitting elements 815A, 815B, 815, and 815D include, but are not limited to, light emitting diodes (LEDs), lasers, vertical-cavity surface-emitting lasers (VCSEL), and light bulbs. Light sources 801, 802, 803, and/or 804 and/or emitting elements, 815A, 815B, 815, and 815D may be configured to deliver light of a power and/or intensity that is sufficient to penetrate the epidermis of, for example, a pregnant mammal's abdomen while not causing damage to the epidermis or any underlying tissue (e.g., fetal ocular tissue or soft tissue). This intensity/power may be established, or recommended, by, for example, one or more regulatory or standard making or enforcement bodies (e.g., American National Standards Institute (ANSI), the Food and Drug Administration (FDA), etc.). One exemplary standard is the ANSI Z136 Standard for Laser Safety, or more particularly, the ANSI Z136.3 standard for Save Use of Lasers in Health Care, which provides a limit of how much power (typically measured in Watts) should be delivered to an area (e.g., cm2) of epidermis.

Additionally, or alternatively, light emitting elements 815A, 815B, 815, and/or 815D, light sources 105, 801, 802, 803, and/or 804, and/or light emitting system 901, 902, 903, and/or 904 discussed below may be configured and/or housed to provide light without exceeding a heat or temperature (e.g., 90° F. 100° F., etc.) threshold in order to, for example, prevent excess delivery of heat to a patient and/or user of one of the systems, light sources, and/or light emitting elements disclosed herein. Maintenance of a preferred temperature range and/or reduction of a temperature for a light source, light emitting element, and/or light emitting system may be accomplished via, for example, use of a temperature sensitive switch that modifies operation of the light source, light emitting, and/or light emitting system and/or a heat sink (not shown) that may be coupled to one or more of the light sources, light emitting elements, and/or light emitting systems disclosed herein. Additionally, or alternatively, one or more of light source, light emitting, and/or light emitting system disclosed herein may include a thermometer designed to measure the temperature of the respective light source, light emitting, and/or light emitting system and/or skin or tissue of a user in contact with the light source, light emitting, and/or light emitting system. For example, if the temperature exceeds a threshold, as indicated by the thermometer or temperature probe like temperature probe 142, a controller such as controller 137 may turn light source 115 off or otherwise adjust the operation of light source 115 to reduce the heat it is producing. In some embodiments, a determination of whether a temperature exceeds a temperature threshold may be made by a processor, like processor 185 and/or a computer like computer 1450 as will be discussed below with regard to FIG. 14 Upon making a determination that the temperature exceeds a threshold, processor 185 and/or computer 1450 may communicate directly with the light source, light emitting, and/or light emitting system to adjust its operation and/or may instruct controller 137 to do so.

Light emitting elements 815A, 815B, 815, and/or 815D may be positioned within light sources 801, 802, 803, and/or 804 to spread out the light and power being delivered to the epidermis of a user in order to, for example, keep within safety limits for power delivery and/or temperature thresholds. For example, if light emitting element 815A emits light of 735 nm with a power of 270 mW/cm2 and light emitting element 815B emits light of 860 nm with a power of and 400 mW/cm2, then light emitting element 815B is emitting light of a higher power than light emitting element 815A and the relative positions of light emitting element 815A and 815B within light sources 801, 802, 803, and/or 804 may be set to keep the power delivered to the epidermis for a given surface area below the limit.

Using light of at least two different wavelengths, as with light emitting elements 815A and 815B, may enable oximetry and/or pulse oximetry calculations and/or determination of hemoglobin oxygen saturation levels via, for example, analysis of ratios of detected light. Using three different wavelengths of light (as with light emitting elements 815A, 815B, and 815C of light source 802) and/or four different wavelengths of light (as with light emitting elements 815A, 815B, and 815C of light source 802) or more different wavelengths may make these calculations easier and/or more accurate because using multiple optical signals/channels (in the form of different wavelengths of light) allows for, among other things, separate analysis of each wavelength, validation of oxygen saturation concentration levels for hemoglobin (e.g., by comparing determinations of different wavelengths) and better attenuation of the received signal. In some embodiments, light sources 801, 802, 803, and/or 804 and/or light emitting elements 815A, 815B, 815, and/or 815D may be configured to work with system 100 as, for example, light source 105 and, in some instances, one or more of housings 805, 815, 820, and 825 and the light emitting elements housed therein may be configured to fit within a housing for light source 105.

In some embodiments, light sources 801, 802, 803, and/or 804 and/or light emitting elements 815A, 815B, 815, and/or 815D may be configured to work with system 100 as, for example, light source 105 and, in some instances, one or more of housings 805, 815, 820, and 825 and the light emitting elements housed therein may be configured to fit within a housing for light source 105.

Additionally, or alternatively, light sources 801, 802, 803, and/or 804 and/or light emitting elements 815A, 815B, 815, and/or 815D may be housed within a light emitting system like light emitting systems 901, 902, 903, and/or 904 as will be discussed below with regard to FIGS. 9A, 9B, 9C, and 9D, respectively.

Figure 9A:
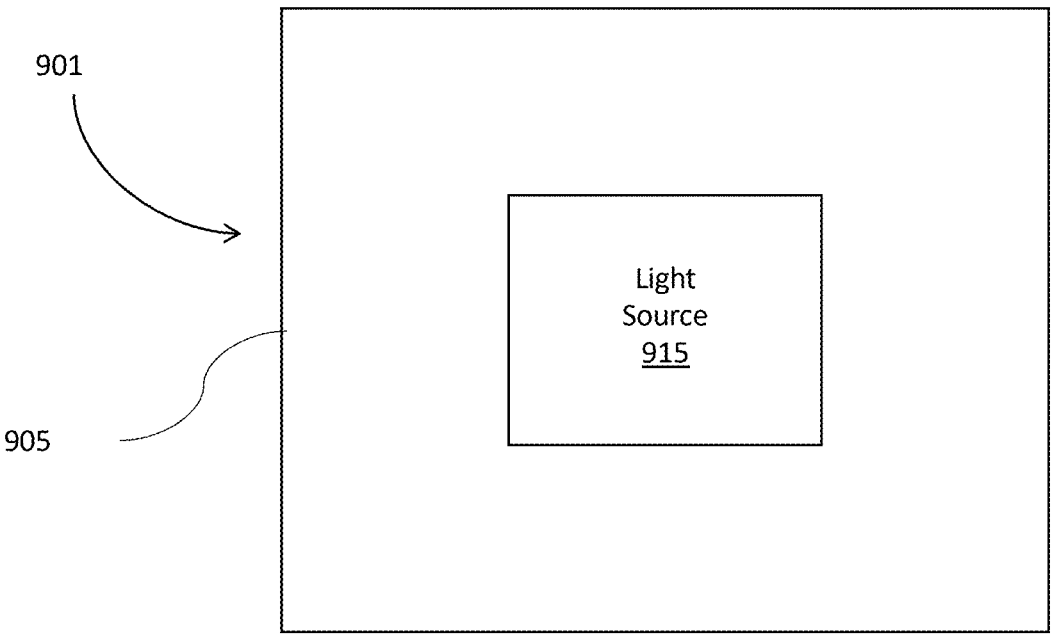
FIG. 9A is a block diagram showing an exemplary light emitting system, consistent with some embodiments of the present invention.
Figure 9B:
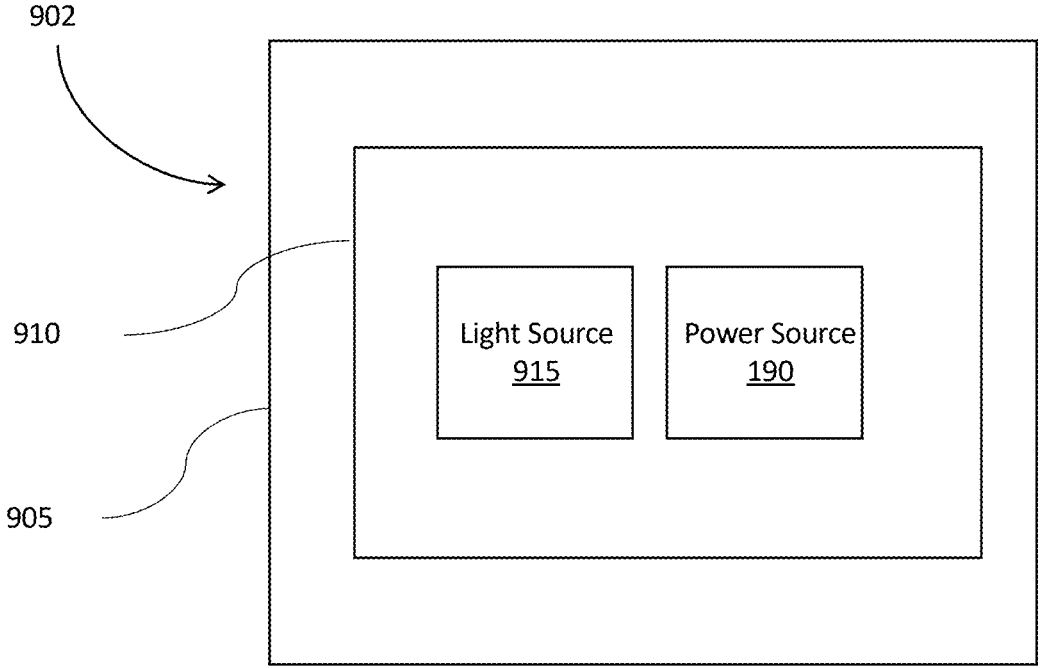
FIG. 9B is a block diagram showing an exemplary light emitting system, consistent with some embodiments of the present invention.
Figure 9C:
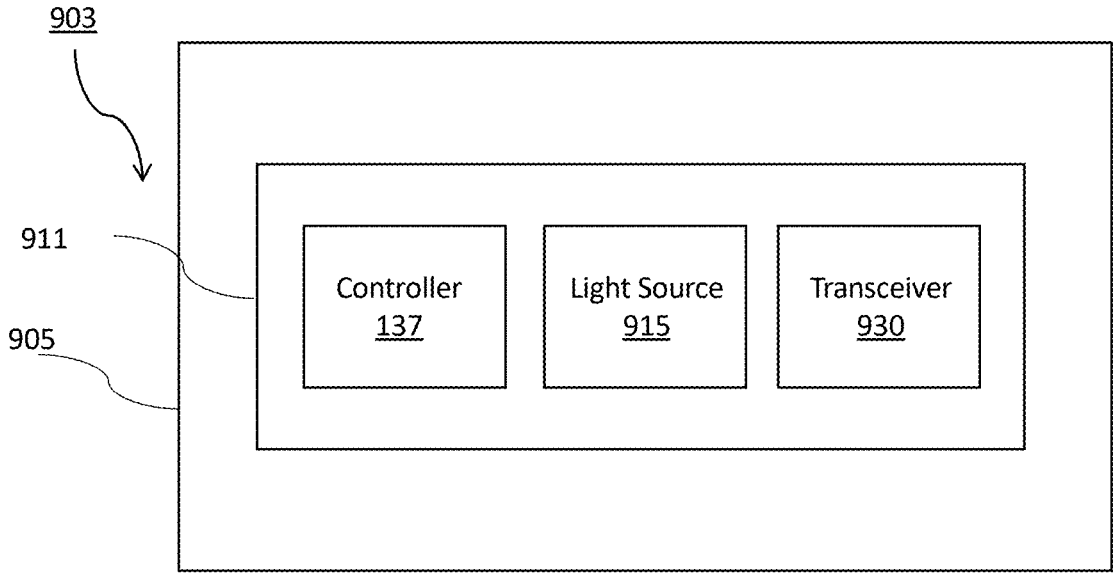
FIG. 9C is a block diagram showing an exemplary light emitting system, consistent with some embodiments of the present invention.
Figure 9D:
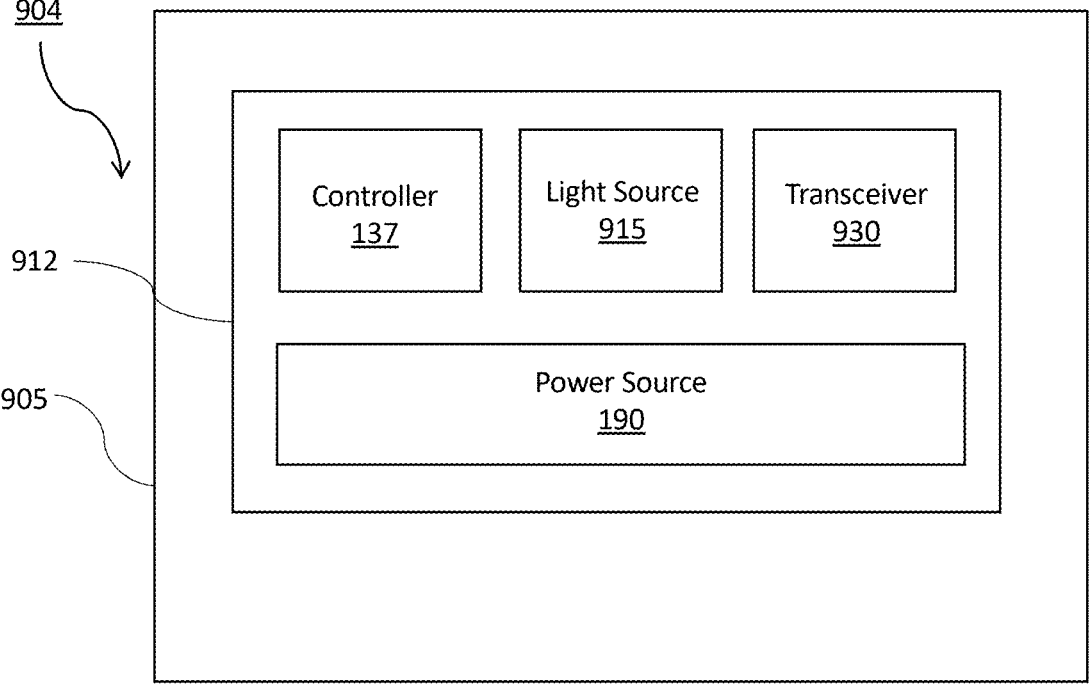
FIG. 9D is a block diagram showing an exemplary light emitting system, consistent with some embodiments of the present invention.

Light emitting system 901 of FIG. 9A includes a housing 905 and a light source, 915. Light emitting system 902 of FIG. 9B includes housing 905, a platform 910 for light source 915, light source 915, and a power source 920. Light emitting system 903 of FIG. 9C includes housing 905, a platform 911, light source 915, a controller 137, and a transceiver 930. Light emitting system 904 of FIG. 1D includes housing 905, a platform 912, light source 915, controller 137, transceiver 930, and power source 920. Light emitting systems 901 and 903, which do not have an on-board power source, may receive power from an external power source like a wire connected to an electrical main or a battery electrically coupled to Light emitting systems 901 and/or 903.

Platform 910 may be configured to hold and electrically couple light source 915 and power source 920. Platform 911 may be configured to hold and electrically and/or communicatively couple light source 915, controller 137, and transceiver 930. Platform 912 may be configured to hold and electrically and/or communicatively couple light source 915, power source 920, controller 137, and transceiver 930.

Controller 137 may be configured to control the operation of light source 915, transceiver 930, and/or power source 920. For example, controller 137 may be configured to turn light source 915 on and off and, in some instances, adjust a wavelength and/or intensity of light emitted by light source 915. For the embodiment of FIG. 1A, light source 915 may be activated via, for example, a switch or other mechanism (not shown). In some embodiments, controller 137 may be configured to communicate with a processor that may be on-board (not shown) or otherwise communicatively coupled to controller 137 via a wired and/or wireless connection. Controller 137 may be configured to receive instructions and/or communicate information to/from the processor directly and/or via communication with transceiver 930.

Controller may also control the operation of power source 920 and/or transceiver 930. Transceiver 930 may be configured to receive and/or send information to/from an external device (e.g., computer or processor). Exemplary received information includes instructions for controller 137 which, when executed by controller 137 cause light source 915 to, for example, turn on or off and/or change a wavelength or intensity (e.g., power) of projected light. Exemplary information transmitted by transceiver 930 includes, but is not limited to, information regarding the operation of system 903 and/or 904 (e.g., power source 920 status, whether light source 915 is functioning properly, etc.) and temperature information.

Housing 905 may be configured to house platform 910, 911, and/or 912 and facilitate attachment of light emitting system 901, 902, 903, and/or 904 to the epidermis of a user. Attachment of housing 905 to the user may be facilitated by, for example, an adhesive (e.g., glue or tape) and/or an external device (e.g., a strap or harness).

In some embodiments, dimensions (e.g., length and/or width) of housing 905 may be configured to provide an optimum distance between two or more light emitting systems 901, 902, 903, and/or 904 positioned proximate to one another so that light may be projected into a particular surface area of the epidermis. Stated differently, the dimensions of housing 905 may be configured so that only a threshold amount of light and/or heat is delivered to the epidermis of the user. For example, housing 905 may have a width and length of 1 cm so that it is a square. The light source 915 of this embodiment may be configured to emit light below a threshold that may cause damage to the epidermis of the user when that light is spread out over a 1 cm2 area. When a plurality of light emitting systems 901, 902, 903, and/or 904 are used, housing 905 may be configured to have dimensions that allow for an arrangement of proximately placed light emitting systems 901, 902, 903, and/or 904 that maximizes the delivery of light to the epidermis while not exceeding a set threshold of light intensity/energy delivered to a particular area of the epidermis.

Figures 10A, 10B:
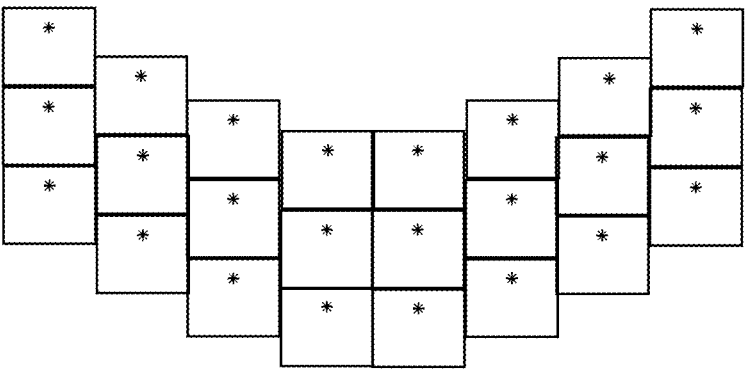
FIG. 10A is a block diagram showing an exemplary array of light emitting systems, consistent with some embodiments of the present invention.
FIG. 10B is a block diagram showing an exemplary array of light emitting systems, consistent with some embodiments of the present invention.

FIGS. 10A-10E provide a few different examples of how a plurality of light emitting systems 901, 902, 903, and/or 904 may be arranged in an array 1001, 1002, 1003, 1004, and 1005, respectively. To facilitate clarity, light emitting systems 901, 902, 903, and/or 904 are represented by an asterisk symbol "*" as shown in FIGS. 10A-10E. FIG. 10A provides a rectangularly shaped array 1001 that includes three rows and eight columns of light emitting systems 901, 902, 903, and/or 904 positioned so that they abut one another (i.e., a housing 905 of each light emitting system 901, 902, 903, and/or 904 touches, or abuts, an edge of at least one adjacent housing 905).

Array 1002 of FIG. 10B shows a plurality of eight columns of three light emitting systems 901, 902, 903, and/or 904 each. The columns are staggered so that the middle two columns form a rectangle and then each column to the left and right of the center two columns is positioned above the preceding column forming a U-like shape. The shape of array 1002 may be configured to direct light into a curved portion of the epidermis such as the underside of a pregnant mammal's abdomen wherein the center two columns may be arranged on the user to align with either side of the user's longitudinal (or sagittal) plane or midline.

Figure 10C:
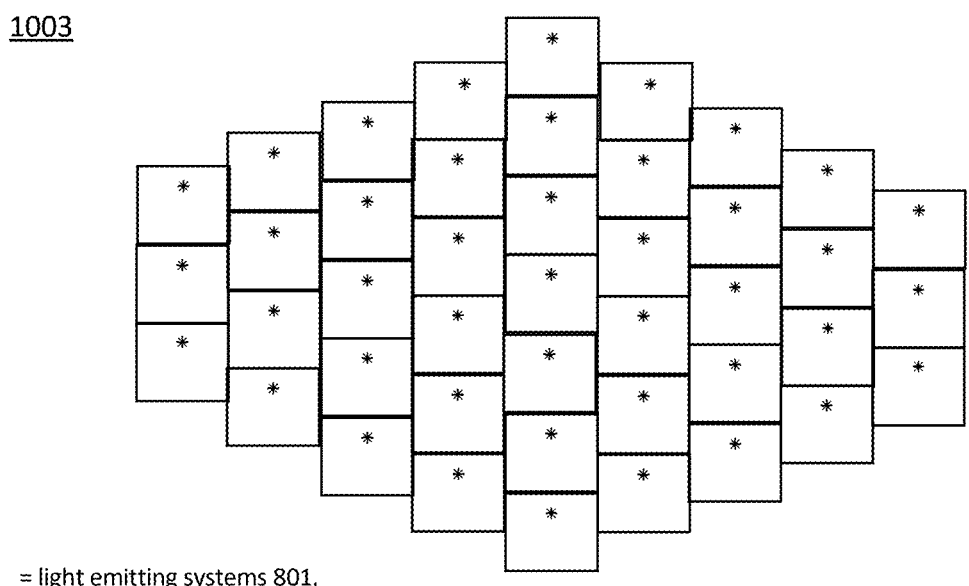
FIG. 10C is a block diagram showing an exemplary array of light emitting systems, consistent with some embodiments of the present invention.
Figure 10D:
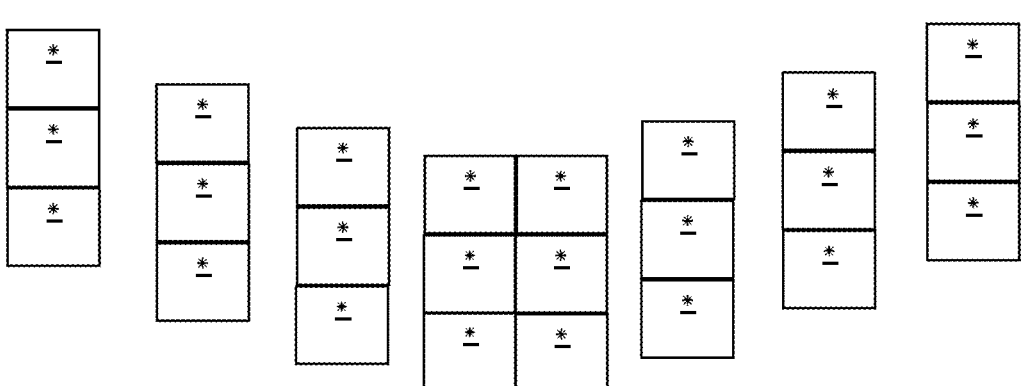
FIG. 10D is a block diagram showing an exemplary array of light emitting systems, consistent with some embodiments of the present invention.
Figure 10E:
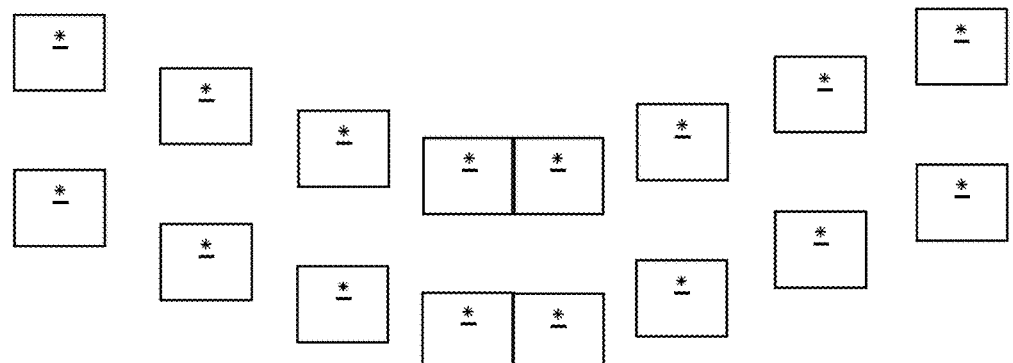
FIG. 10E is a block diagram showing an exemplary array of light emitting systems, consistent with some embodiments of the present invention.

Array 1003 of FIG. 10C shows a plurality of light emitting systems 901, 902, 903, and/or 904 arranged in a diamond-like formation where a first and a ninth column have three light emitting systems 901, 902, 903, and/or 904 that abut one another, a second and eighth column have four light emitting systems 901, 902, 903, and/or 904, a third and a seventh column have five light emitting systems 901, 902, 903, and/or 904, a fourth and a sixth column have six light emitting systems 901, 902, 903, and/or 904 and a central column includes seven light emitting systems 901, 902, 903, and/or 904, that abut one another. The columns of array 1003 are arranged so that they are next to one another.

Arrays 1001, 1002, and 1003 are arranged to form a continuous arrangement of light emitting systems 901, 902, 903, and/or 904 so that the area of the epidermis under the array is approximately uniformly lit and a maximum number of photons may be delivered to the epidermis and any underlying tissue and/or a fetus.

In some instances, an array of light emitting systems 901, 902, 903, and/or 904 that are contiguously arranged (e.g., arrays 1001, 1002, and/or 1003) may not be preferred and it may be advantageous to have some distance between individual light emitting systems 901, 902, 903, and/or 904 and/or columns or rows of light emitting systems 901, 902, 903, and/or 904. Reasons why a contiguous array may not be desired include, but are not limited to, conservation of resources and/or limiting the amount of light projected into the epidermis. Examples of these types of arrays are provided by FIGS. 10D and 10E, which show an array 1004 and 1005, respectively. Array 1004 includes eight columns of three light emitting systems 901, 902, 903, and/or 904 that abut one another with empty spaces between the first, second, third columns and empty spaces between fifth, sixth, seventh, and eighth columns. Array 1005 includes eight columns of light emitting systems 901, 902, 903, and/or 904 wherein the light emitting systems 901, 902, 903, and/or 904 of the first, second, third, sixth, seventh, and eighth columns do not abut one another and are surrounded by empty space.

In some embodiments, each of the light emitting systems 901, 902, 903, and/or 904 may be individually positioned within an array and/or individually placed on the epidermis of the user. Additionally, or alternatively, one or more of the light emitting systems 901, 902, 903, and/or 904 may be pre-positioned in an array like the arrays 1001-1005 and may be affixed to the user's epidermis as a complete or partial array (i.e., each light emitting systems 901, 902, 903, and/or 904 may not have to be individually placed on the epidermis).

Additionally, or alternatively, in some embodiments, a plurality of arrays 1001, 1002, 1003, 1004, and/or 1005 may be used. For example, an upper edge of array 1002 may be positioned on the epidermis of a user so that it is proximate to and/or fits together with a lower edge of array 1003. Additionally, or alternatively, array 1001 may be positioned on the left and/or right side of array 1002, 1003, 1004, and/or 1005.

In some embodiments, individual light emitting systems 901, 902, 903, and/or 904 and/or arrays of light emitting systems 901, 902, 903, and/or 904 may be placed on the epidermis in any configuration for a variety of reasons including, but not limited to, a shape or orientation of target tissue and a physiological characteristic of the user. In some circumstances, an array of light emitting systems 901, 902, 903, and/or 904 may be arranged so that it surrounds a particular body part (e.g., abdomen or limb) so that the body part may receive illumination from a variety of angles.

In some embodiments, an array and/or individual light emitting system 901, 902, 903, and/or 904 may be a modular array that may be configured, added to, and/or subtracted from in any useful arrangement according to, for example, body type, configuration, target of the illumination, etc.

In some embodiments, not all of the light emitting systems 901, 902, 903, and/or 904 of an array may be used at the same time. For example, if the target of illumination is a fetus inside a pregnant mammal's abdomen, an array of light emitting systems 901, 902, 903, and/or 904 may extend over a large portion (e.g., 80% or 90%) of the pregnant mammal's abdomen so that the entire abdomen may be illuminated. In some circumstances, it may be desired to illuminate only a portion of the abdomen responsively to, for example, fetal position and/or fetal movement so that, for example, only the fetus's head or back is illuminated and other portions of the fetus or uterus are not illuminated. Information regarding fetal position and/or movement may be received from, for example, an ultrasound or other imaging device.

Light source 915, light emitting systems 901, 902, 903, and/or 904 and/or an array of light emitting systems 901, 902, 903, and/or 904 may be configured to deliver the maximum number of photons to the epidermis of a user while staying below a threshold number of photons that may damage the epidermis and/or underlying tissue.

Figure 11A:
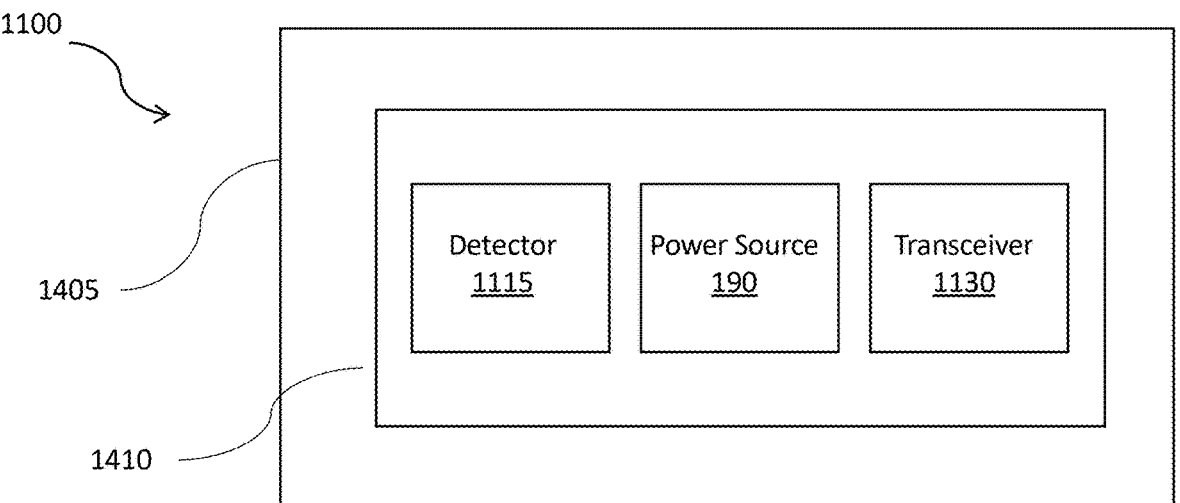
FIG. 11A provide a block diagram of an exemplary photo-detecting system, consistent with some embodiments of the present invention.
Figure 11B:
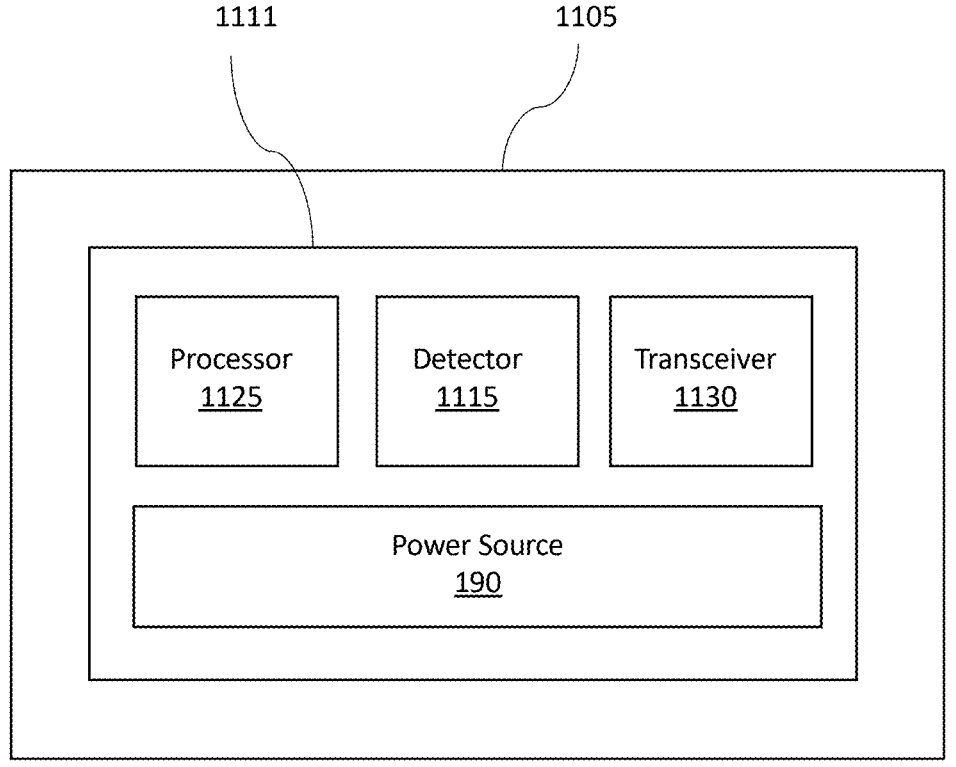
FIG. 11B provide a block diagram of an exemplary photo-detecting system, consistent with some embodiments of the present invention.

FIGS. 11A and 11B provide block diagrams of two exemplary photo-detecting systems 1100 and 1101, respectively. Photo-detecting systems 1100 includes a housing 1105, a platform 1110, a detector 1115, an optional power source 1120, and an optional transceiver 1130. System 1101 includes housing 1105, a platform 1111, detector 1115, optional power source 1120, optional transceiver 1130, and a processor 1125. Detector 1115 may be a photodetector configured to receive an optical signal from the epidermis of the user responsively to the light projected into the epidermis of the user by, for example, light source 105 and/or light emitting systems 901, 902, 903, and/or 904 and convert the received optical signal into a digital or analog electrical signal. Detector 1115 may be similar to detector 115, discussed above. A digital and/or analog signal detected by detector 1115 may then be communicated to an external device or processor via transceiver 1100. Processor 1125 may control one or more operations (e.g., powering on or off, application of filters, communication, etc.) of photo-detecting system 1101. In some embodiments, processor may receive a detected electronic signal that corresponds to optical signal(s) received by detector 1115 and may process, or filter, the detected electronic signal prior to communication of the detected electronic signal to an external processor (e.g., computer 1450.

Platform 1110 may be configured to hold detector 1115, transceiver 1100, and power source 1120 and platform 1111 may be configured to hold detector 1115, transceiver 1100, power source 1120, and processor 1125. Platforms 1110 and 1111 may facilitate communication the components they hold.

Housing 1105 may be configured to house platform 1110 or platform 1111, detector 1115, power source 1120, and processor 1125 and facilitate use of photo-detecting systems 1100 and/or 1101 with light emitting systems 901, 902, 903, and/or 904 and/or an array of light emitting systems 901, 902, 903, and/or 904. In some embodiments, housing 1105 may include an adhesive by which housing 1105 may be affixed to the epidermis of the user. Additionally, or alternatively, housing 1105 may be configured to affix to a secondary housing (e.g., a strap or harness) that may be configured to place the photo-detecting systems 1100 and 1101 in a preferred location and/or maintain their position there.

FIGS. 12A-12E illustrate different examples of how photo-detecting systems 1100 and/or 1101 may be used in conjunction with/positioned around an array of light emitting systems 901, 902, 903, and/or 904. Many other combinations are possible and the arrangements of FIGS. 9A-9E are exemplary only.

Figure 12A:
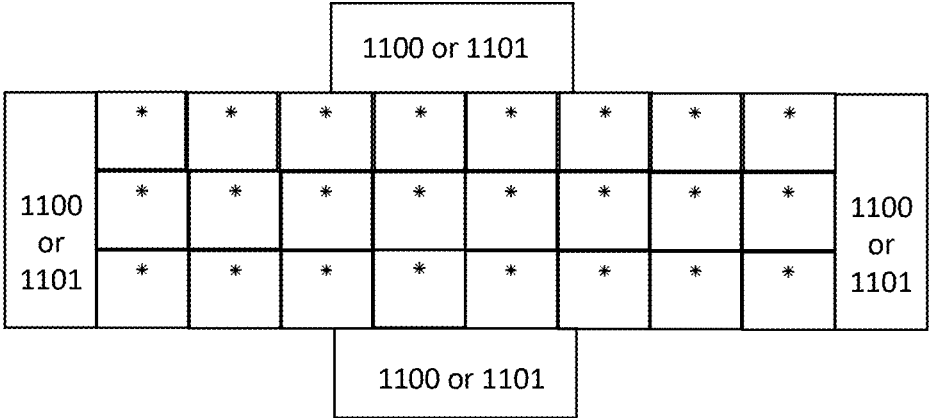
FIG. 12A is a block diagram showing a first exemplary array of light emitting systems and photo-detecting systems, consistent with some embodiments of the present invention.

FIG. 12A shows array 1201 with four photo-detecting systems 1100 and/or 1101 positioned on the perimeter of the array with a photo-detecting system 1100 or 1101 being positioned on the left and right sides of array 1001 and a photo-detecting system 1100 or 1101 positioned in the center of the upper and lower edges of array 1001.

Figure 12B:
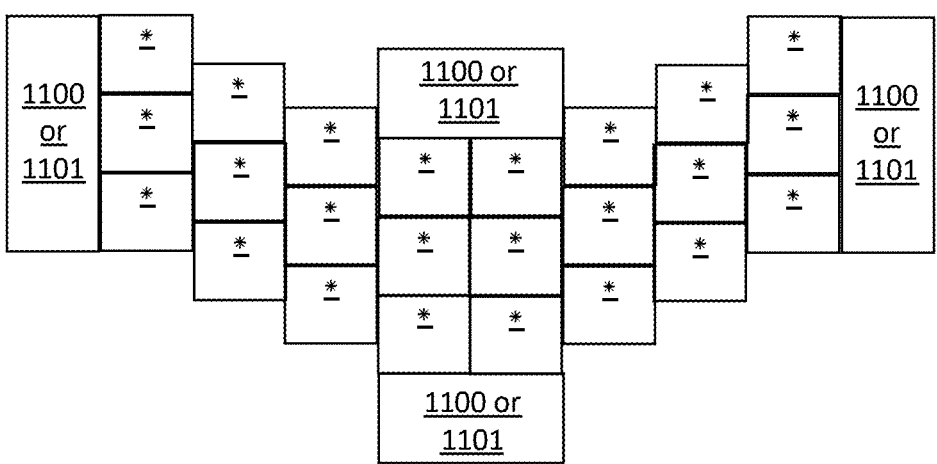
FIG. 12B is a block diagram showing a second exemplary array of light emitting systems and photo-detecting systems, consistent with some embodiments of the present invention.

FIG. 12B shows array 1202 with four photo-detecting systems 1100 and/or 1101 positioned on the exterior of the array with a photo-detecting system 1100 or 1101 being positioned on the left and right sides of array 1002 and a photo-detecting system 1100 or 1101 positioned in the center of the upper and lower edges of array 1202.

Figure 12C:
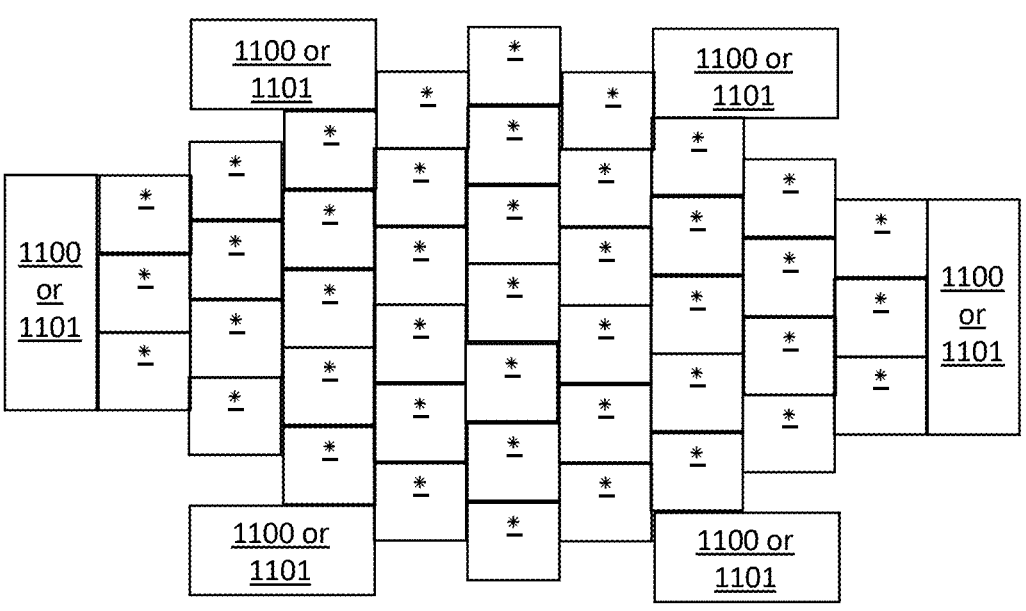
FIG. 12C is a block diagram showing a third exemplary array of light emitting systems and photo-detecting systems, consistent with some embodiments of the present invention.

FIG. 12C shows array 1203 with six photo-detecting systems 1100 and/or 1101 positioned on the perimeter of array 1203 with a photo-detecting system 1100 or 1101 being positioned on the left and right sides of array 1003, a photo-detecting system 1100 or 1101 positioned in the upper left and right of the center line and the lower left and right of the center line of array 1003.

Figure 12D:
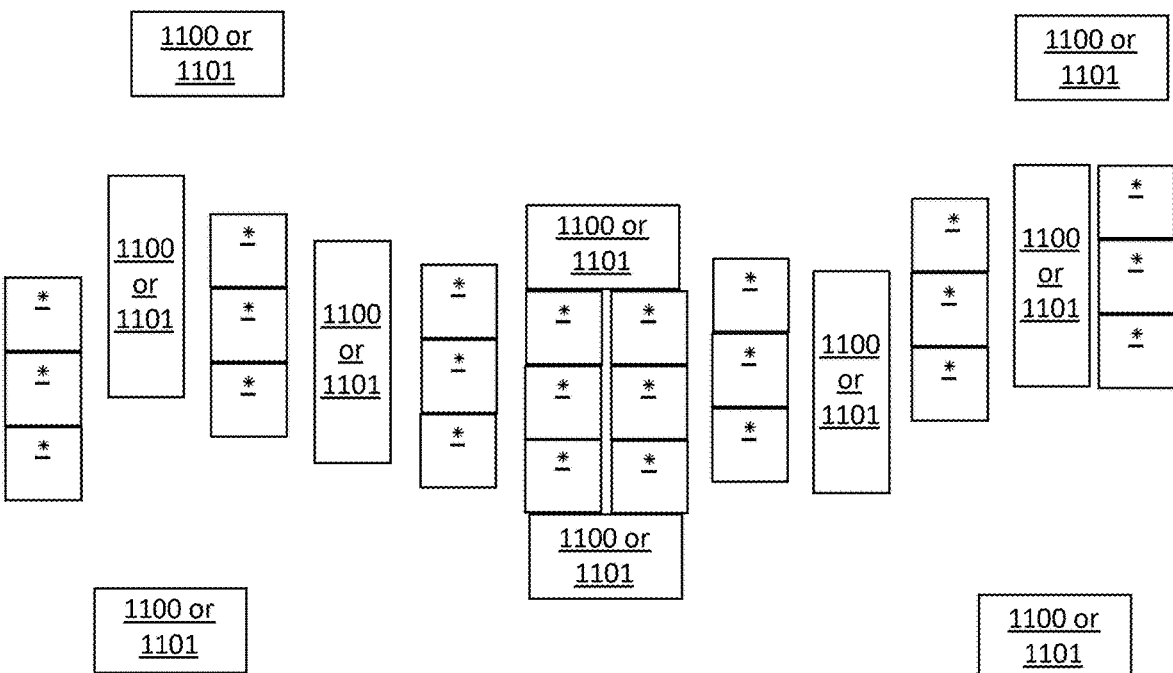
FIG. 12D is a block diagram showing a fourth exemplary array of light emitting systems and photo-detecting systems, consistent with some embodiments of the present invention.

FIG. 12D shows array 1204 with ten photo-detecting systems 1100 and/or 1101 positioned between the first and second; second and third; sixth and seventh; and seventh and eighth columns light emitting systems 901, 902, 903, and/or 904 of as well as above and below the two center columns and in the four corners above and below array 1004.

Figure 12E:
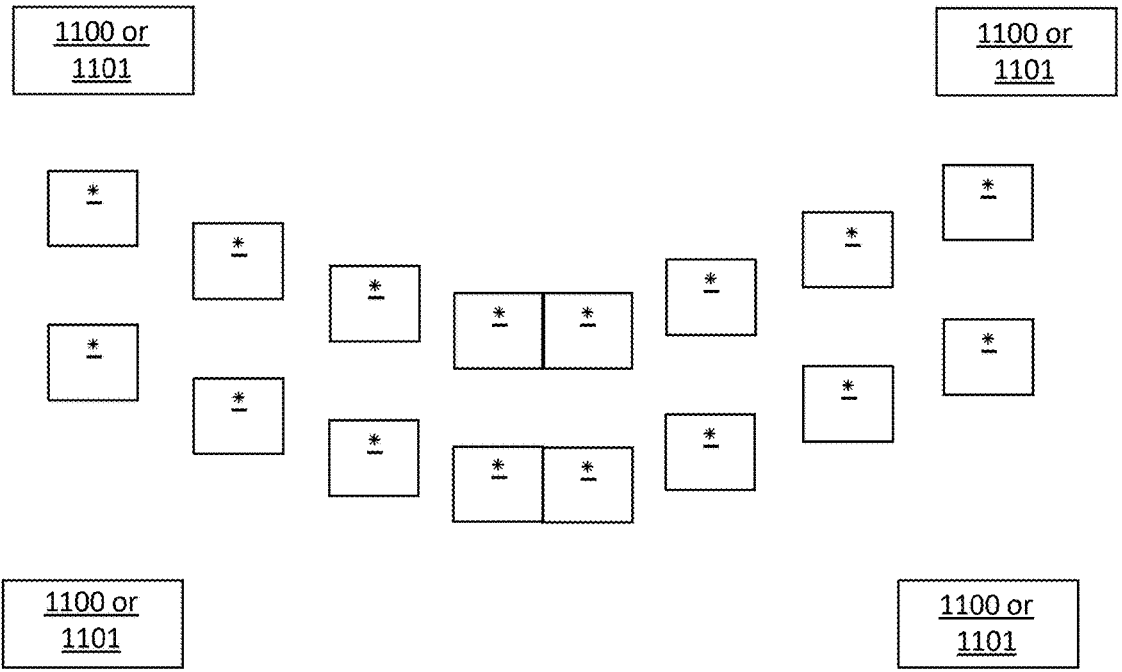
FIG. 12E is a block diagram showing a fifth exemplary array of light emitting systems and photo-detecting systems, consistent with some embodiments of the present invention.

FIG. 12E shows array 1205 with four photo-detecting systems 1100 and/or 1101 positioned at the four corners above and below array 1205.

Figure 13:
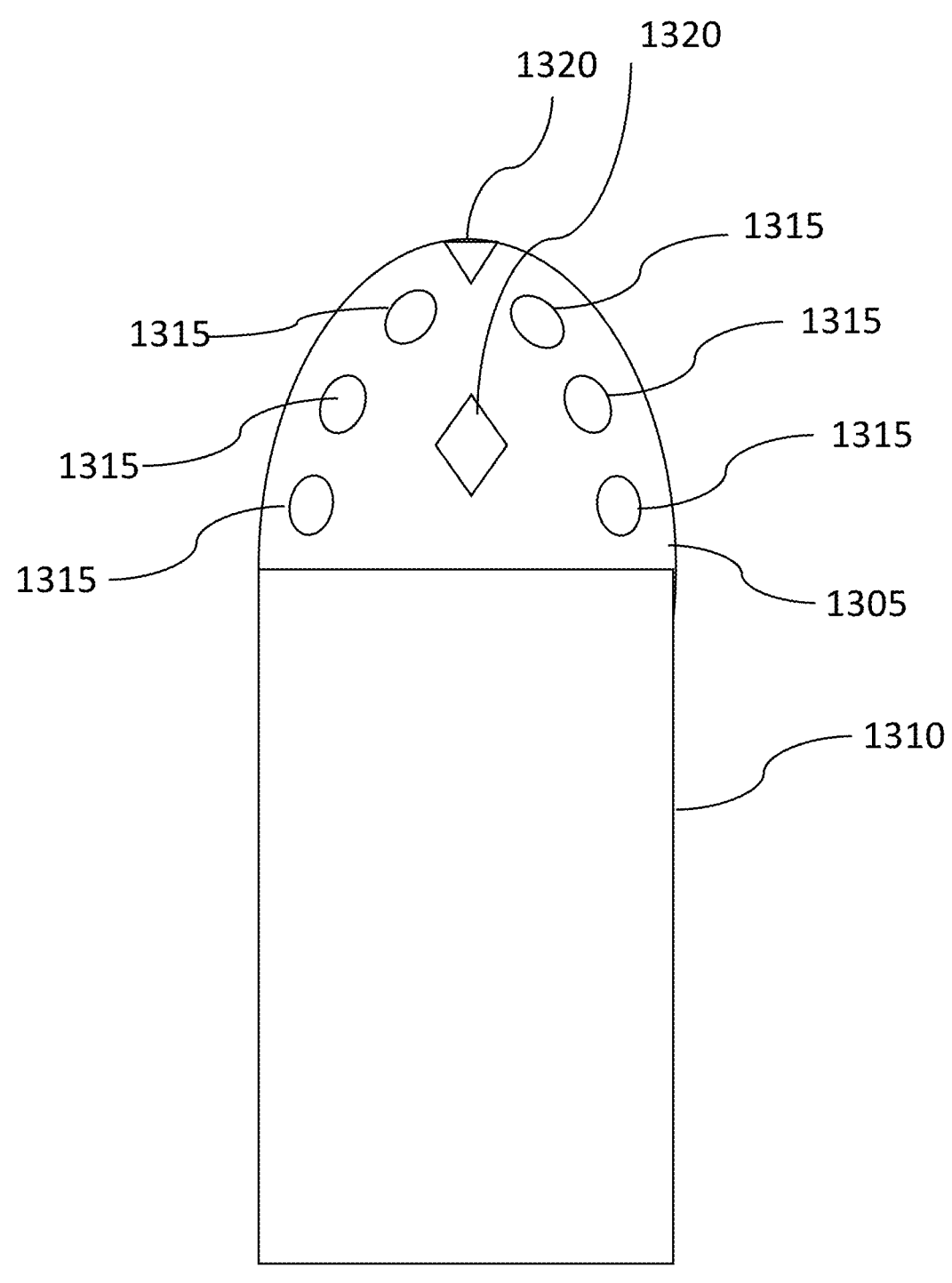
FIG. 13 provides a front plan view of an exemplary optical probe, consistent with some embodiments of the present invention.

FIG. 13 provides a front plan view of an exemplary optical probe 1300 to be inserted into an opening (e.g., vagina, rectum, or surgical incision) in a patient's body so that tissue inside the patient's body may be illuminated and/or light projected into the patient's body may be detected. This may be helpful in illuminating the fetus of a pregnant mammal because, for example, probe 1300 may be able to get closer to the fetus with fewer intervening layers of maternal tissue than when a trans-abdominal optical probe is used.

Probe 1300 includes a head 1305 and a wand body 1310. Head includes two light sources 1320 and a plurality of detectors 1315 arranged, in the exemplary embodiment of FIG. 13, in two lines of three detectors 1315 each. Exemplary light sources 1320 include any of the light sources and/or light emitting elements disclosed herein. Exemplary detectors 1315 include any of the detectors and/or detector systems disclosed herein.

In some embodiments, detectors 1315 may be arranged so that they detect light coming from a particular direction and may be arranged to pick up light over, for example, 60°, 90°, 180°, 270°, and/or 360°. In this way, light from a target direction may be detected. This may be helpful when trying to detect photons passing through a fetus because the detectors may be arranged so that they primarily detect photons coming from a direction that indicates they may have passed through the fetus and photons passing through the pregnant mammal's body that do not pass through the fetus may not be detected.

Probe 1300 also includes two light sources 1320 configured to emit light into the body of the patient. It will be understood by those of skill in the art that probe head 1305 may include any number of detectors 1315 and light sources 1320.

Probe wand body 1310 may be configured to provide a housing for probe head 1305 and may facilitate the insertion and/or positioning of probe 1300 within the patient's body. Probe wand body 1310 may also house one or more wires or optical fibers for the transmission and/or communication of electrical or optical information between light sources 1320 and/or detectors 1315 and a transceiver (not shown) and/or computer or processor. Additionally, or alternatively, probe wand body 1310 may house one or more wires for the provision of electrical power to light sources 1320 and/or detectors 1315. Additionally, or alternatively, probe wand body 1310 may act as a heat sink for one or more of the light sources 1320 and/or detectors 1315.

In some embodiments, optical probe 1300 may be used in combination with one or more light emitting systems 901, 902, 903, and/or 904, and/or detectors or photo-detecting systems like detectors 1115 and/or photo-detecting systems 1100 and 1101 positioned outside the body (e.g., on the epidermis of the patient) to, for example, deliver photons to tissue inside the patient and/or a fetus of a pregnant mammal for detection by the photo-detecting systems 1100 and 1101 and/or detectors 1115. Additionally, or alternatively, optical probe 1300 may be used in combination with one or more light emitting systems 901, 902, 903, and/or 904, positioned outside the body (e.g., on the epidermis of the patient) to, for example, detect photons projected into the body, or maternal abdomen, to detect photons passing through the patient's tissue and/or her fetus.

For some embodiments disclosed herein, light from different light emitting systems 901, 902, 903, and/or 904 and/or light source(s) 915 may be differentiated from one another in the time and/or frequency (frequency here being a periodic/time-based frequency, not a frequency of light or electro-magnetic radiation) domain. For example, a first light emitting system 901, 902, 903, and/or 904 and/or a first set of light emitting systems 901, 902, 903, and/or 904 may be scheduled to emit pulses of light with a first periodic frequency and a second light emitting system 901, 902, 903, and/or 904 and/or a second set of light emitting systems 901, 902, 903, and/or 904 may be scheduled to emit pulses of light with a second periodic frequency and/or at the first frequency but time shifted so pulses of light for the second light emitting system 901, 902, 903, and/or 904 and/or second set of light emitting system 901, 902, 903, and/or 904 are emitted at a different time than the pulses of light emitted by the first light emitting system 901, 902, 903, and/or 904 and/or a first set of light emitting system 901, 902, 903, and/or 904. This separation in the time domain may be useful in determining which light emitting system 901, 902, 903, and/or 904 and/or set of light emitting systems 901, 902, 903, and/or 904 detected light/photons originated from.

In some embodiments, one or more light emitting systems 901, 902, 903, and/or 904 and/or light source(s) 915 may be positioned on the maternal abdomen relative to photo-detecting systems 1100 and 1101 and/or detectors 1115 so that only a signal from the mother is detected/received (also referred to as a pure maternal signal). For example, a distance (e.g., 2-5 cm) between a light emitting system and a detector system may be established so that light that may be incident on the fetus is not detected and/or only light incident on the pregnant mammal is detected. Having a purely maternal signal may be helpful when isolating a portion of a detected signal that is contributed by the fetus so that that the fetal hemoglobin oxygen saturation level may be determined.

One or more of the systems and/or devices disclosed herein may be powered by an on-board (e.g., battery) and/or external (e.g., electrical main) power source. In some cases, a substance may be applied to the epidermis of the user and/or pregnant mammal to aid in the transfer of light thereto and/or the isolation of the epidermis from ambient light. Examples of such substances include, but are not limited to, alcohol, oil, gel, and lubricants.

Figure 14:
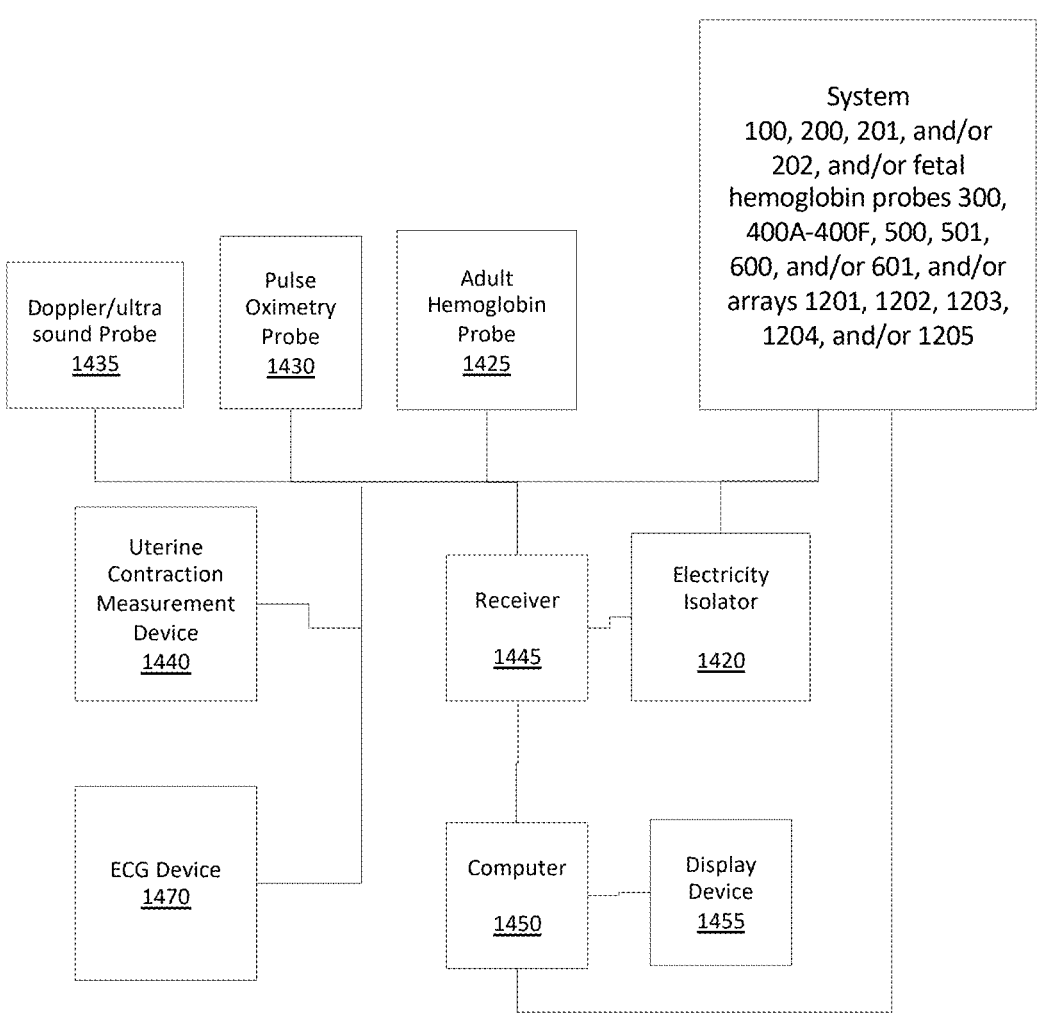
FIG. 14 provides a diagram of an exemplary system configured to perform some of the methods described herein, consistent with some embodiments of the present invention.

FIG. 14 provides a diagram of an exemplary system 1400 that includes system 100, 200, 201, and/or 202 and/or fetal hemoglobin probes 300, 400A-400F, 500, 501, 600, 601, and/or arrays 1201, 1202, 1203, 1204, and/or 1205 as described above along with one or more optional components including, but not limited to, an adult hemoglobin probe 1425, a pulse oximetry probe 1430, a uterine contraction measurement device 1440, a receiver 1445, a computer 1450, a Doppler/ultrasound probe 1435, an ECG device 1470, an electricity isolator 1420, and a display device 1455. A user (e.g., doctor, nurse, technician, or other care giver) may interact with (e.g., communicate instructions to and/or receive information from) systems 100, 200, 201, and/or 202 and/or fetal hemoglobin probes 300, and/or 400A-400F and/or components thereof via computer 1450 and/or receiver 1445. Exemplary interactions include, but are not limited to, communication of instructions (directly or indirectly) to and receipt of information from light source 105, detector 115, motor 120, transceiver 122, temperature probe 143, fan 132, controller 137, and fetal heart monitor 180. Exemplary electricity isolators 120 include transformers and non-conducting materials. A heartbeat signal for the pregnant mammal may be provided by ECG device 1470. Doppler/ultrasound probe may be configured to determine, for example, a fetal heartbeat signal and/or a fetal position or depth within the pregnant mammal's abdomen.

Receiver 1445 may be configured to receive signals and/or data from one or more components of system(s) 100, 200, 201, and/or 202 and/or fetal hemoglobin probes 300, and/or 400A-400F via wired or wireless communication that, in some instances, utilizes one or more communication ports. In some instances, receiver 1445 may be configured to process or pre-process received signals so as to, for example, make the signals compatible with computer 1450 (e.g., convert an optical signal to an electrical signal), improve SNR, filter a signal, amplify a received signal, etc. In some instances, receiver 1445 may be resident within and/or a component of computer 1450. Also, while receiver 1445 is depicted in FIG. 14 as a single receiver, that is not necessarily the case as any number of appropriate receivers (e.g., 2, 3, 4, 6) may be used to receive signals from system(s) 100, 200, 201, and/or 202 and/or fetal hemoglobin probes 300, and/or 400A-400F and/or components thereof and communicate them to computer 1450. In some embodiments, computer 1450 may amplify or otherwise condition the received reflected signal so as to, for example, improve the signal-to-noise ratio, isolate a portion of a received signal reflected from the pregnant mammal and/or isolate a portion of a received signal reflected by a fetus.

Receiver 1445 may communicate received, pre-processed, and/or processed signals to computer 1450. Computer 1450 may act to process the received signals to determine, for example, a fetal hemoglobin oxygen saturation, and facilitate provision of the results to a display device 1455. Exemplary computers 1450 include desktop and laptop computers, servers, tablet computers, personal electronic devices, mobile devices (e.g., smart phones), and so on. Exemplary display devices 1455 are computer monitors, tablet computer devices, and displays provided by one or more of the components of system 1400. In some instances, display device 1455 may be resident in receiver 1445 and/or computer 1450.

Pulse oximetry probe 1430 may be a conventional pulse oximetry probe placed on pregnant mammal's hand and/or finger to measure the pregnant mammal's oxygen saturation. Adult hemoglobin probe 1425 may be placed on, for example, the pregnant mammal's 2nd finger and may be configured to, for example, use near infrared spectroscopy to calculate the ratio of adult oxyhemoglobin to adult de-oxyhemoglobin, which may then be used to determine the pregnant mammal's oxygen saturation. Adult hemoglobin probe 1425 may also be used to determine the pregnant mammal's heart rate.

Uterine contraction measurement device 1440 may be configured to measure the strength and/or timing of the pregnant mammal's uterine contractions. In some embodiments, uterine contractions will be measured by uterine contraction measurement device 1440 as a function of pressure (measured in e.g., mmHg) over time. In some instances, the uterine contraction measurement device 1440 is and/or includes a to cotransducer, which is an instrument that includes a pressure-sensing area that detects changes in the abdominal contour to measure uterine activity and, in this way, monitors frequency and duration of contractions.

In another embodiment, uterine contraction measurement device 1440 may be configured to pass an electrical current through the pregnant mammal and measure changes in the electrical current as the uterus contracts. Additionally, or alternatively, uterine contractions may also be measured via near infrared spectroscopy because uterine contractions, which are muscle contractions, are oscillations of the uterine muscle between a contracted state and a relaxed state. Oxygen consumption of the uterine muscle during these states is different and these differences may be detectable using NIRS.

In some embodiments, uterine contraction measurement device 1440 may be used in conjunction with light (emitted by light source 105) reflected by the pregnant mammal's uterus and received by detector 115 to determine uterine tone and other related information. In some instances, uterine contraction measurement device 1440 may be used to verify a uterine tone determination based on light received by detector 115 and vice versa.

Measurements from adult hemoglobin probe 1425, pulse oximetry probe 1430, Doppler and/or ultrasound probe 1435, and/or uterine contraction measurement device 1440 may be communicated to receiver 1445 for communication to computer 1450 and display on display device 1455 and/or received directly to computer 1450. In some instances, one or more of adult hemoglobin probe 1425, pulse oximetry probe 1430, a Doppler and/or ultrasound probe 1435, uterine contraction measurement device 1440 may include a dedicated display that provides the measurements to, for example, an operator or medical treatment provider.

Measurements provided by adult hemoglobin probe 1425, pulse oximetry probe 1430, a Doppler and/or ultrasound probe 1435, uterine contraction measurement device 1440 may be used in conjunction with light received by detector to isolate a fetal pulse signal and/or fetal heart rate from a maternal pulse signal and/or maternal heart rate. The isolated fetal pulse signal and/or fetal heart rate may then be used to determine an oxygen level of the fetus.

The light detected by detector 115 may be analyzed to determine fetal hemoglobin oxygen saturation and/or uterine tone of the pregnant mammal. When determining uterine tone, light source 105 and detector 115 may act as an optoelectronic muscle contraction sensor. IN some instances, without the need for a separate uterine contraction measurement device 140. In these embodiments, the light reflected from the pregnant mammal's uterus might change in nature when the uterus is in a relaxed state (more scattering) as opposed to a contracted state (less scattering). These changes in the rate of scattering of the light may be detected by detector 115 and processed by, for example, computer 1450 to determine changes in the state of the uterine muscle. In some embodiments, one or more light source(s) 105 may direct light of a particular frequency/wavelength that may be different from the frequency/wavelength of light used to determine fetal hemoglobin oxygen saturation so that measurements of uterine contractions have a dedicated beam/frequency of light.

FIG. 15 provides a flowchart illustrating a process 1500 for determining a fetal hemoglobin oxygen saturation level. In step 1505, light emitted from the abdomen of a pregnant mammal may be received. Often times, the light received in step 1505 may be resultant from the plurality of photons projected into the pregnant mammal's abdomen by light emitting systems 901, 902, 903, and/or 904 and/or an array like array 1001, 1002, 1003, 1004, and/or 1005 via, for example, reflection and/or transmission through the maternal tissue. In step 1510, the received light may be converted into an electronic detected signal by a photo detector included in photo-detecting systems 300 and/or 301.

In some instances, electronic detected signal may be received by a processor or computer without performance of step(s) 1505 or 1510. The electronic detected signal may be analyzed to isolate a portion of the signal that has be incident upon/reflected from the fetus (step 1515). This portion of the signal may be referred to as a fetal signal. The fetal signal may then be analyzed to determine a hemoglobin saturation level of the fetus (step 1520) using, for example, the Beer-Lambert Law or the Modified Beer-Lambert Law and the fetal hemoglobin saturation level may be provided to an operator (e.g., doctor or treatment provider) (step 1525).

Figure 16A:
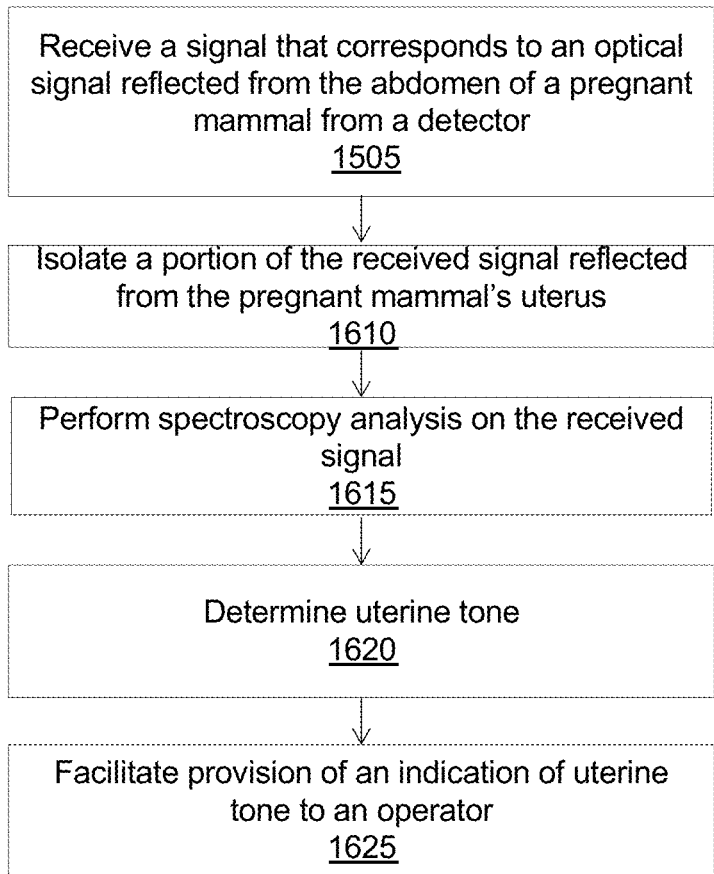
FIG. 16A provides a flowchart illustrating a process for determining a state of uterine muscle tone, consistent with some embodiments of the present invention.

FIGS. 16A and 16B provide flowcharts of processes for determining a state (e.g., contracted or relaxed) of uterine muscle tone (uterine tone) 1600 and 1601, respectively. Processes 1600 and 1601 may be executed by, for example, any of the systems and/or devices disclosed herein.

In step 1605, a signal that corresponds to an optical signal reflected from the abdomen of a pregnant mammal may be received from a detector, such as one or more of the detectors 115 described herein, that has converted the reflected optical signal into a corresponding electronic signal.

The optical signal received by the detector may correspond to an optical signal directed into the abdomen of the pregnant mammal from one or more light sources, like light source 15, that is then reflected from the abdomen of a pregnant mammal and received by the detector. Often times, the light directed into the pregnant mammal's abdomen and the fetus will be of at least two separate wavelengths and/or frequencies (e.g., red, infrared, near-infrared, etc.) so that the reflected signal includes light of a corresponding number of frequencies.

In some instances, the signal received in step 1605 may be received from a single detector (as opposed to a plurality of detectors). In embodiments where a fetal hemoglobin probe housing the detector from which the signal is received includes multiple detectors, the signal may be received from the detector that is closest to the light source as this signal may provide a clearer indication of light reflected from the pregnant mammal's uterus with less interference from other sources of light (e.g., light reflected from the fetus, ambient light, etc.).

Next, in step 1610, a portion of the received signal that is reflected from the pregnant mammal's uterus may be isolated from the received signal. In some embodiments, one or more light source(s) 15 may direct light of a particular frequency/wavelength of a particular strength so that it penetrates the pregnant mammal's abdomen to her uterus (but preferably no deeper). In these embodiments, execution of step 1610 may include extracting a portion of the received signal that corresponds to light of this particular frequency/wavelength.

Then, in step 1615, spectroscopy may be performed on the isolated signal of step 1610. In some embodiments, where a portion of the isolated signal corresponds to the NIR light, the spectroscopy performed on the received signal may be NIR spectroscopy. When a muscle, such as the pregnant mammal's uterus, is in a contracted state it consumes a first level of oxygen and, when a muscle is in a relaxed state, it consumes a second level of oxygen. These differences in oxygen consumption of the pregnant mammal's uterus may therefore be detectable by analyzing the results of the NIR spectroscopy performed in step 1610 and, in step 1615, this information may be used to determine oscillations of the uterine muscle between a contracted state and a relaxed state (i.e., uterine tone) over time so that contractions of the pregnant mammal's uterus may be monitored. Provision of uterine tone to an operator may then be facilitated (step 1620).

Additionally, or alternatively, to process 1600, process 1601 may also be executed. In step 1655, a signal that corresponds to an optical signal reflected from the abdomen of a pregnant mammal may be received from a detector, such as detector 115, that has converted the reflected optical signal into a corresponding electronic signal. Step 1655 may be similar to step 1605.

Next, in step 1660, a portion of the received signal that is reflected from the pregnant mammal's uterus may be isolated from the received signal. Execution of step 1660 may be similar to execution of step 1610. Then, a degree of scattering of the light corresponding to the received signal may be determined (step 1660). As indicated above, the light reflected from the pregnant mammal's uterus might change in nature when the uterus is in a relaxed state (more scattering) as opposed to a contracted state (less scattering). The received signal may be analyzed to determine a level of scattering of the light over time. Changes in the level of scattering of the light over time may then be used to detect changes in the state of the uterine muscle (i.e., contracted or relaxed) or uterine tone (step 1665).

Figure 17:
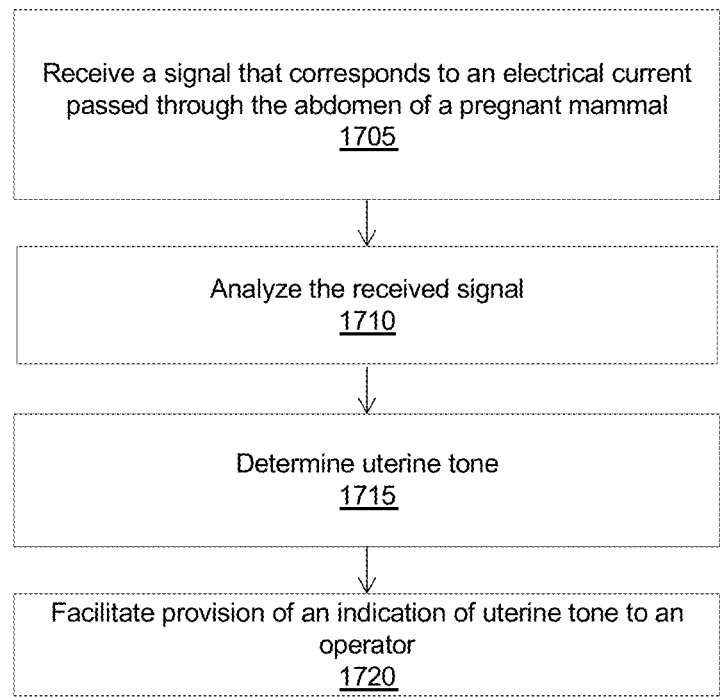
FIG. 17 provides a flowchart illustrating a process for determining a state of uterine muscle tone, consistent with some embodiments of the present invention.

Additionally, or alternatively to execution of processes 1600 and 1601, process 1700, as depicted in the flowchart of FIG. 17, for determining uterine tone may also be executed. Initially, in process 1700, a signal that corresponds to an electrical current that passes through the abdomen (e.g., skin and muscle) may be received over time (step 1705). The electrical current may be supplied to the pregnant mammal's abdomen via an electrode, such as electrode 170. The received signal may be analyzed to determine changes in the amount of electrical current that passes through the pregnant mammal's abdomen (step 1715). Because muscle in a contracted state will allow a different amount of electrical current to pass through it than a muscle in a relaxed state, these changes in the amount of electrical current that passes through the pregnant mammal's abdomen may indicate changes in the uterine tone of the pregnant mammal.

In another embodiment, uterine contraction measurement device 140 may be configured to pass an electrical current through the pregnant mammal and measure changes in the electrical current as the uterus contracts.

In some instances, two or more of processes 1600, 1601 and/or 1700 may be executed to, for example, validate a uterine tone determination. An advantage of both process 1600 and 1601 is that either, or both, may be executed without the need for a separate uterine tone monitor, as is the current state of the art. This greatly simplifies the equipment needed to monitor a pregnant mammal during, for example, the labor and delivery process and makes monitoring the pregnant mammal more efficient and cost effective.

FIG. 18 provides a flowchart illustrating a process 1800 for determining an optimum distance between a light source and a detector and/or determining a fetal hemoglobin oxygenation level. Process 1800 may be executed by, for example, any of the systems and/or devices disclosed herein.

Initially, in step 1805, an indication of fetus' position within an abdomen of pregnant mammal and/or a distance between an epidermis of pregnant mammal's abdomen and a fetus contained therein may be received by a processor like processor 185, processor 1904 and/or a processor included in computer 1450. The indication received in step 1805 may be one or more of, for example, an ultrasound reading, an ultrasound image, and a magnetic resonance imaging image. In some embodiments, execution of step 1805 may include determining the distance between the epidermis of the pregnant mammal's abdomen and the fetus contained therein using responsively to the received indication.

Optionally, an optimum distance between a light source and a detector for the transmission of light to the fetus and detecting light emanating from the pregnant mammal's abdomen that has been incident upon the fetus may be determined (step 1810). The determination of step 1810 may be responsive to the indication received in step 1805. In some embodiments, the determination of step 1810 may be based on a path length and/or time of flight for light or photons traveling through the pregnant mammal's abdomen. In some embodiments, the determination of the optimum distance may be responsive to a measured and/or expected signal strength of a portion of the detected electronic signal that is contributed by light incident upon the fetus.

Provision of an indication of the optimum distance between the light source and a detector responsively to the determination to a user may then be facilitated by, for example, communicating the indication to a display device like display 1912.

Optionally, a movement of at least one of the light source and the detector may be initiated responsively to the optimum distance (step 1820). Initiation of the movement may be performed by sending an instruction to a motor like motor 120 communicatively coupled to the processor and mechanically coupled to the light source and/or detector and/or an arm that is mechanically coupled to the respective light source and/or detector such as arms 130 and 135, respectively. Additionally, or alternatively, initiation of the movement may be performed by sending an instruction to a motor like motor 120 housed within a housing coupled to the source and detector like housing 125, the motor being communicatively coupled to the processor and mechanically coupled to the light source and/or detector and/or an arm that is mechanically coupled to the respective light source and/or detector such as arms 130 and 135, respectively. Additionally, or alternatively, initiation of the movement may be performed by sending an instruction to a motor like motor 120 housed within a housing coupled to the source and detector like centerpiece 605, the motor being communicatively coupled to the processor and mechanically coupled to one or more of arms 610A and/or 610B so that one or more detectors 115A, 115B, and/or 115C (in the instance of system 600) and/or light source 105C (in the instance of system 601) may move to, for example, optimize the delivery of light to the fetus and/or the detection of light incident upon/emanating from, the fetus.

Additionally, or alternatively, in step 1825, a plurality of detected electronic signals may be received. The received detected electronic signals may correspond to a detected optical signal emanating from a pregnant mammal's abdomen and a fetus contained therein, wherein each detected optical signal has been converted, by the respective detector, into one of the plurality of the detected electronic signals. The optical signal may be responsive to light projected into the pregnant mammal's abdomen from one or more light sources like light source 105. Each of the plurality of detected electronic signals may be received from a separate detector communicatively coupled to the processor. Exemplary systems of detectors that may be detecting the detected electronic signals are circularly-shaped fetal hemoglobin probe 500 and/or 501, fetal hemoglobin probe 600 and/or 60, and/or an array of light sources and detectors described herein such as array 1201, 1202, 1203, 1204, and 1205.

In step 1830, one or more detected electronic signal(s) may be selected from the plurality of detected electronic signals. In some embodiments, the selection of step 1830 may be responsive to a received position for each of the detectors providing a detected electronic signal. Additionally, or alternatively, the selection of step 1830 may be responsive to a determination of which detected electronic signals of the plurality detected electronic signals have a signal to noise ratio (SNR) above a threshold amount (e.g., an SNR of 1:1).

Next, the selected signal(s) may be analyzed to determine a fetal hemoglobin oxygen saturation level (step 1835). In some embodiments, execution of step 1835 may include determining a ratio of a first wavelength of light (e.g., red light) included in the selected signal and a second wavelength of light included in the selected signal (e.g., near-infrared (NIR) light) and this ratio may be used to determine the fetal hemoglobin oxygen saturation level via known correlations between this ratio and the oxygen saturation of fetal hemoglobin via, for example, use of the Beer-Lambert Law and/or the Modified Beer-Lambert Law. Provision of the determined fetal hemoglobin oxygen saturation level to a user (e.g., doctor or nurse) may then be facilitated via, for example, communication of the fetal hemoglobin oxygen saturation level to a display device (e.g., display screen of a computer) like display device 155 (step 1840). In some embodiments, step 1840 may be performed by providing the user with a numerical value and/or graph showing the fetal hemoglobin oxygen saturation level and/or changes to fetal hemoglobin oxygen saturation level. Additionally, or alternatively, the fetal hemoglobin oxygen saturation level may be provided as a time weighted average over, for example, 30 seconds, 1, 2, 5, 10, 30, etc. minutes. Optionally, in some embodiments, step 1810 may be performed prior to execution of step 1830.

In some embodiments, the selection of step 1835 includes isolating a portion of the detected electronic signal that corresponds to light incident upon the fetus. This isolation may be done by, for example, filtering out a portion of the signal contributed by light incident on the pregnant mammal but not the fetus (as may be determined by, for example, determining a portion of the selected detected electronic signal that corresponds to a maternal heartbeat or pulse signal), amplifying a portion of the detected electronic signal that corresponds to a fetal heartrate or pulse signal, application of digital filtering/amplification techniques (e.g., lock-in amplifiers, wavelet filters, etc.), and/or noise reduction (e.g., filtering out ambient light).

FIG. 19 provide an example of a processor-based system 1900 that may store and/or execute instructions for the processes described herein. Processor-based system 1900 may be representative of, for example, computing device 1450 and/or the components of housing 125 and/or 605. Note, not all of the various processor-based systems which may be employed in accordance with embodiments of the present invention have all of the features of system 1900. For example, certain processor-based systems may not include a display inasmuch as the display function may be provided by a client computer communicatively coupled to the processor-based system or a display function may be unnecessary. Such details are not critical to the present invention.

System 1900 includes a bus 1902 or other communication mechanism for communicating information, and a processor 1904 coupled with the bus 1902 for processing information. System 1900 also includes a main memory 1906, such as a random access memory (RAM) or other dynamic storage device, coupled to the bus 1902 for storing information and instructions to be executed by processor 1904. Main memory 1906 also may be used for storing temporary variables or other intermediate information during execution of instructions to be executed by processor 1904. System 1900 further includes a read only memory (ROM) 1908 or other static storage device coupled to the bus 1902 for storing static information and instructions for the processor 1904. A storage device 1910, which may be one or more of a floppy disk, a flexible disk, a hard disk, flash memory-based storage medium, magnetic tape or other magnetic storage medium, a compact disk (CD)-ROM, a digital versatile disk (DVD)-ROM, or other optical storage medium, or any other storage medium from which processor 1904 can read, is provided and coupled to the bus 1902 for storing information and instructions (e.g., operating systems, applications programs and the like).

System 1900 may be coupled via the bus 1902 to a display 1912, such as a flat panel display, for displaying information to a user. An input device 1914, such as a keyboard including alphanumeric and other keys, may be coupled to the bus 1902 for communicating information and command selections to the processor 1904. Another type of user input device is cursor control device 1916, such as a mouse, a trackball, or cursor direction keys for communicating direction information and command selections to processor 1904 and for controlling cursor movement on the display 1912. Other user interface devices, such as microphones, speakers, etc. are not shown in detail but may be involved with the receipt of user input and/or presentation of output.

The processes referred to herein may be implemented by processor 1904 executing appropriate sequences of processor-readable instructions stored in main memory 1906. Such instructions may be read into main memory 1906 from another processor-readable medium, such as storage device 1910, and execution of the sequences of instructions contained in the main memory 1906 causes the processor 1904 to perform the associated actions. In alternative embodiments, hard-wired circuitry or firmware-controlled processing units (e.g., field programmable gate arrays) may be used in place of or in combination with processor 1904 and its associated computer software instructions to implement the invention. The processor-readable instructions may be rendered in any computer language.

System 1900 may also include a communication interface 1918 coupled to the bus 1902. Communication interface 1918 may provide a two-way data communication channel with a computer network, which provides connectivity to the plasma processing systems discussed above. For example, communication interface 1918 may be a local area network (LAN) card to provide a data communication connection to a compatible LAN, which itself is communicatively coupled to other computer systems. The precise details of such communication paths are not critical to the present invention. What is important is that system 1900 can send and receive messages and data through the communication interface 1918 and in that way communicate with other controllers, etc.

For the embodiments herein described, the light directed into the pregnant mammal's abdomen and the fetus may be of at least two separate wavelengths and/or frequencies (e.g., red, infrared, near-infrared, etc.) and the received detected electronic signals may correspond to light of these different wavelengths.

Hence, systems, devices, and methods for determining fetal oxygen level have been herein disclosed. In some embodiments, use of the systems, devices, and methods described herein may be particularly useful during the labor and delivery of the fetus (e.g., during the first and/or second stage of labor) because it is difficult to assess fetal health during the labor and delivery process.

We claim:

1. A method comprising:
   receiving, by a processor, a first detected electronic signal that corresponds to light that penetrates the maternal abdomen to a first depth, the first depth being less than a distance between an epidermis of a pregnant mammal's abdomen and a fetus contained therein;

receiving, by the processor, a second detected electronic signal that corresponds to light that penetrates the maternal abdomen to a second depth, the second depth being more than the distance between the epidermis of the pregnant mammal's abdomen and the fetus contained therein;

filtering, by the processor, the second detected signal using the first detected signal, thereby isolating a portion of the second detected signal that is contributed by the fetus, thereby generating a fetal signal;

determining, by the processor, a fetal hemoglobin oxygen saturation level using the fetal signal; and providing, by the processor, the fetal hemoglobin oxygen saturation level to a display device.

2. The method of claim 1, further comprising:
   analyzing, by the processor, the first detected signal;
   determining, by the processor, an indication of uterine tone for the pregnant mammal responsively to the analysis; and
   communicating, by the processor, the indication of uterine tone to a display device.

3. The method of claim 1, further comprising:
   analyzing, by the processor, the first detected signal;
   determining, by the processor, a level of scattering of the first detected signal responsively to the analysis;
   determining, by the processor, an indication of uterine tone for the pregnant mammal responsively to the analysis; and
   communicating, by the processor, the indication of uterine tone to a display device.

4. The method of claim 1, further comprising:
   analyzing, by the processor, the first detected signal;
   determining, by the processor, a rate of change between a level of scattering of a first increment of the first detected signal and a level of scattering of a second increment of the first detected signal responsively to the analysis;
   determining, by the processor, an indication of uterine tone for the pregnant mammal responsively to the rate of change; and
   communicating, by the processor, the indication of uterine tone to a display device.

5. The method of claim 1, wherein the first detected signal is detected by a first detector and the second detected signal is detected by a second detector.

6. The method of claim 1, wherein the determination is performed using pulse oximetry calculations.

7. A non-transitory computer-readable medium storing a set of instructions, wherein execution of the set of instructions by a processor cause the processor to:
   receive an indication of a distance between an epidermis of a pregnant mammal's abdomen and a fetus contained therein;
   determine an optimum distance between one or more detectors of a plurality of detectors configured to be located at a position on the pregnant mammal's abdomen and a light source;
   send an instruction to a motor to move the one or more detectors of the plurality of detectors or the light source responsively to the determined optimum distance, wherein the motor is housed within a housing coupled to the light source and the plurality of detectors, the motor being mechanically coupled to arms with each arm mechanically coupled to the light source or respective detector of the plurality of detectors so that one or more detectors of the plurality of detectors or the light source are configured to move to optimize a delivery of light to the fetus or a detection of light incident upon or emanating from the fetus;

receive a plurality of detected electronic signals, each of the plurality of detected electronic signals being received from a separate detector of the plurality of detectors communicatively coupled to the processor and corresponding to a detected optical signal emanating from the pregnant mammal's abdomen and the fetus contained therein, wherein each detected optical signal has been converted, by the respective detector, into one of the plurality of the detected electronic signals;

receive a position for each of the plurality of detectors;

select a detected electronic signal from the plurality of detected electronic signals responsively to the position of the detector corresponding to the selected detected signal and the indication of the distance between the epidermis of the pregnant mammal's abdomen and the fetus contained therein;

analyze the selected detected signal to determine a fetal hemoglobin oxygen saturation level of the fetus; and facilitate provision of an indication of the fetal hemoglobin oxygen saturation level to a user.

8. The non-transitory computer-readable medium method of claim 7, wherein the analysis includes isolating a portion of the detected electronic signal that corresponds to light incident upon the fetus.

9. The non-transitory computer-readable medium method of claim 7, wherein the determining of the optimum distance between the one or more detectors of the plurality of detectors and the light source for transmission of light to the fetus and detecting light emanating from the pregnant mammal's abdomen that has been incident upon the fetus is performed prior to the selecting and responsive to the distance between the epidermis of the pregnant mammal's abdomen and the fetus contained therein, wherein the selecting of the detected electronic signal is responsive to the optimum distance.

10. A method comprising:

receiving, by a processor, a plurality of detected electronic signals, each detected electronic signal of the plurality corresponding to an optical signal emanating from the abdomen of a pregnant mammal;

receiving, by a processor, an indication of a distance between an epidermis of the pregnant mammal's abdomen and a fetus contained therein;

selecting, by the processor, a first detected electronic signal from the plurality that corresponds to light that penetrates the maternal abdomen to a first depth responsively to the indication of the distance between the epidermis of the pregnant mammal's abdomen and the fetus contained therein, the first depth being less than a distance between an epidermis of a pregnant mammal's abdomen and a fetus contained therein;

selecting, by the processor, a second detected electronic signal from the plurality that corresponds to light that penetrates the maternal abdomen to a second depth responsively to the indication of the distance between the epidermis of the pregnant mammal's abdomen and the fetus contained therein the second depth being more than a distance between an epidermis of a pregnant mammal's abdomen and a fetus contained therein;

filtering, by the processor, the second detected signal using the first detected signal, thereby isolating a portion of a second detected signal that is contributed by the fetus, thereby generating a fetal signal;

determining, by the processor, a fetal hemoglobin oxygen saturation level using the fetal signal; and providing the fetal hemoglobin oxygen saturation level to a display device.

* * * * *